(12) United States Patent
Zhang

(10) Patent No.: US 12,558,258 B2
(45) Date of Patent: Feb. 24, 2026

(54) SYSTEMS AND METHODS FOR ADMINISTERING FLUID COMPOSITIONS

(71) Applicant: Aurora Tears Technology, Inc., Santa Clara, CA (US)

(72) Inventor: Ping Cerina Zhang, Santa Clara, CA (US)

(73) Assignee: Aurora Tears Technology, Inc., Santa Clara, CA (US)

( * ) Notice: Subject to any disclaimer, the term of this patent is extended or adjusted under 35 U.S.C. 154(b) by 393 days.

(21) Appl. No.: 18/221,362

(22) Filed: Jul. 12, 2023

(65) Prior Publication Data

US 2023/0355434 A1    Nov. 9, 2023

Related U.S. Application Data

(63) Continuation-in-part of application No. 17/673,672, filed on Feb. 16, 2022, now Pat. No. 11,801,162, (Continued)

(51) Int. Cl.
*A61M 11/00*     (2006.01)
*A61F 9/00*     (2006.01)
(Continued)

(52) U.S. Cl.
CPC .......... *A61F 9/0026* (2013.01); *A61K 9/0048* (2013.01); *A61K 47/14* (2013.01); (Continued)

(58) Field of Classification Search
CPC .. A61M 11/001; A61M 11/005; A61M 11/02; A61M 15/0003; A61M 15/0066; (Continued)

(56) References Cited

U.S. PATENT DOCUMENTS 4,914,088 A     4/1990 Glonek et al.
5,201,726 A *  4/1993 Kirkham ............. B05B 11/0005
604/297
(Continued)

FOREIGN PATENT DOCUMENTS

WO     WO2013/089835 A1     6/2013

OTHER PUBLICATIONS

Aurora Tears Technology, Inc., International Search Report and Written Opinion, PCT/US2019/034008, Oct. 1, 2019, 11 pgs.
(Continued)

*Primary Examiner* — Kai H Weng
(74) *Attorney, Agent, or Firm* — Morgan, Lewis & Bockius LLP

(57) ABSTRACT

A device for administering fluid compositions includes a housing having a first end with an opening. The housing includes a compartment, proximate to the first end, that is capable of holding a liquid reservoir that is at least partially filled with a fluid. The device includes an air pump positioned within the housing, at a second end. The device includes an actuator positioned between the compartment and the air pump. The actuator includes an extendible piston that is configured to extend laterally toward the compartment. During device operation, the actuator causes the piston to extend towards the liquid reservoir and exert a force on the liquid reservoir. The force causes the fluid to be expelled from the liquid reservoir at the first end. The air pump is configured to atomize the fluid at the first end as it is expelled from the liquid reservoir.

19 Claims, 19 Drawing Sheets

Related U.S. Application Data which is a continuation of application No. 16/933,874, filed on Jul. 20, 2020, now Pat. No. 11,253,395, which is a continuation-in-part of application No. 16/464,631, filed as application No. PCT/US2019/034008 on May 24, 2019, now Pat. No. 11,464,672.

(60) Provisional application No. 63/389,309, filed on Jul. 14, 2022, provisional application No. 62/679,154, filed on Jun. 1, 2018.

(51) Int. Cl.

| | | |
|---|---|---|
| *A61K 9/00* | (2006.01) | |
| *A61K 47/14* | (2017.01) | |
| *A61K 47/44* | (2017.01) | |

(52) U.S. Cl.
CPC .......... *A61K 47/44* (2013.01); *A61M 11/001* (2014.02); *A61M 11/006* (2014.02); *A61M 2210/0612* (2013.01)

(58) Field of Classification Search
CPC ...... A61M 2205/07; A61M 2205/3334; A61M 2205/3365; A61M 2205/3553; A61M 2205/3592; A61M 2205/502; A61M 2205/505; A61M 2205/583; A61M 2205/6018; A61M 2205/8206; A61M 2210/0612; A61K 38/1735; A61K 9/0024; A61K 9/0048; A61F 9/0008
See application file for complete search history.

(56) References Cited

U.S. PATENT DOCUMENTS

| | | | |
|---|---|---|---|
| 5,371,108 A | 12/1994 | Korb et al. | |
| 8,012,136 B2 * | 9/2011 | Collins, Jr. | ........... A61F 9/0008 604/294 |
| 8,936,021 B2 | 1/2015 | Collins, Jr. | |
| 2003/0108626 A1 | 6/2003 | Benita et al. | |
| 2004/0142038 A1 | 7/2004 | Echols et al. | |
| 2005/0202097 A1 | 9/2005 | Maskin | |
| 2006/0097074 A1 | 5/2006 | Wang | |
| 2007/0082017 A1 | 4/2007 | Tseng | |
| 2010/0222752 A1 | 9/2010 | Collins | |
| 2010/0226963 A1 | 9/2010 | Cooper | |
| 2012/0130322 A1 | 5/2012 | Kleyne | |
| 2016/0177298 A1 | 6/2016 | Green | |
| 2022/0168143 A1 | 6/2022 | Zhang | |

OTHER PUBLICATIONS

Aurora Tears Technology, Inc., International Preliminary Report on Patentability, Application No. PCT/US2019/034008, Dec. 1, 2020, 7 pgs.

Zhang, Non-Final Office Action, U.S. Appl. No. 16/933,874, Feb. 22, 2021, 8 pgs.

Zhang, Non-Final Office Action, U.S. Appl. No. 16/933,874, Feb. 25, 2021, 14 pgs.

Zhang, Final Office Action, U.S. Appl. No. 16/933,874, May 28, 2021, 17 pgs.

Zhang, Notice of Allowance, U.S. Appl. No. 16/933,874, Dec. 1, 2021, 10 pgs.

Zhang, Notice of Allowance, U.S. Appl. No. 16/464,631, Apr. 13, 2022 , 9 pgs.

Zhang, Notice of Allowance, U.S. Appl. No. 16/464,631, May 24, 2022 , 8 pgs.

Zhang, Office Action, U.S. Appl. No. 17/673,672, Mar. 20, 2023, 9 pgs.

Zhang, Notice of Allowance, U.S. Appl. No. 17/673,672, Jun. 15, 2023, 9 pgs.

Aurora Tears Technology, Inc., CN201980041886, First Office Action, Feb. 26, 2024, 19 pgs.

* cited by examiner

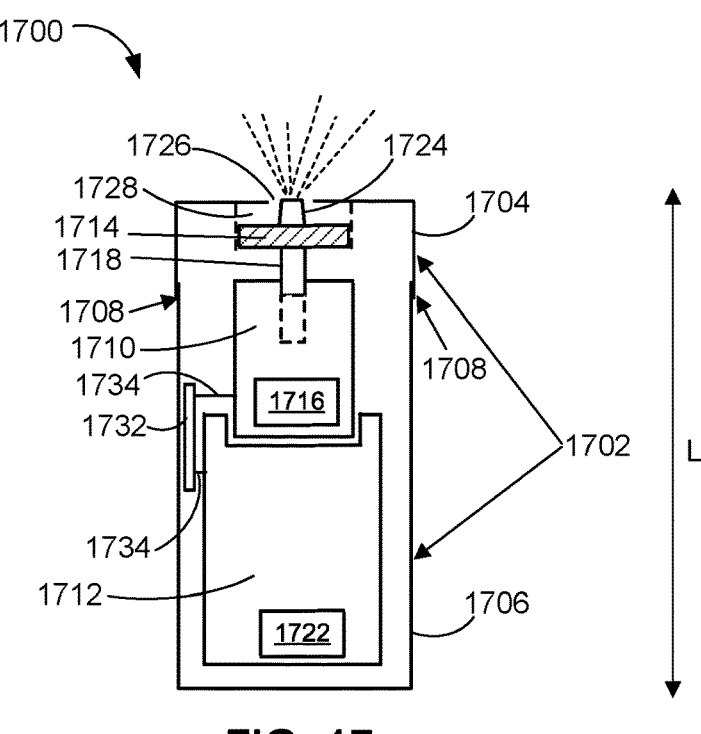
FIG. 17
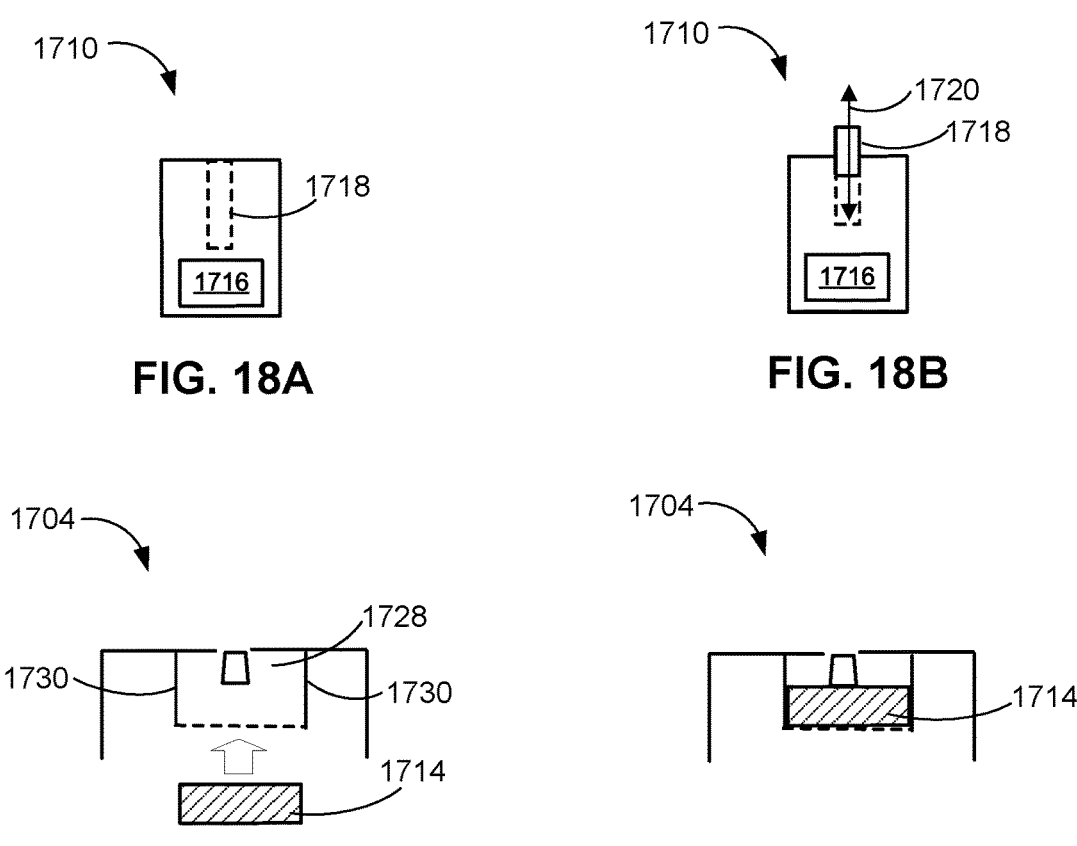
FIG. 18A
FIG. 18B
FIG. 19A
FIG. 19B

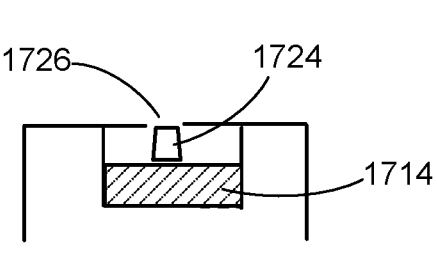
FIG. 20A
FIG. 20B
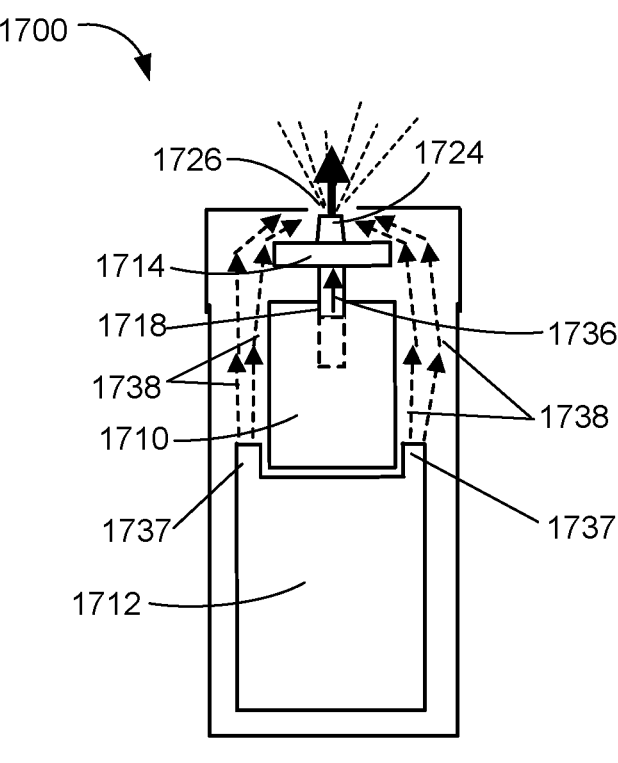
FIG. 21

2200

2205
2204
2207
2206
1714
2202-a
2202
1718
1710
1712
2202-a

2200

2204
1714
1718
1710
2202
1712

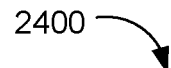

2400

2402 Operate the actuator such that the piston extends towards a compartment of the device and exerts a force on a liquid reservoir positioned in the compartment such that the force causes the fluid to be expelled from the liquid reservoir, at a first end of the device.

2404 Operate the air pump to atomize the fluid at the first end as it is expelled from the liquid reservoir.

FIG. 24

SYSTEMS AND METHODS FOR ADMINISTERING FLUID COMPOSITIONS

PRIORITY CLAIMS AND RELATED APPLICATIONS

This application is a continuation-in-part of U.S. application Ser. No. 17/673,672, filed Feb. 16, 2022, entitled "Systems and Methods for Generating and Applying Biomimicry Tear Films," which is a continuation of U.S. application Ser. No. 16/933,874, filed Jul. 20, 2020, entitled "Systems and Methods for Generating and Applying Biomimicry Tear Films," now U.S. Pat. No. 11,253,395, issued on Feb. 22, 2022, which is a continuation-in-part of U.S. application Ser. No. 16/464,631, filed May 28, 2019, entitled "Systems and Methods for Generating and Applying Biomimicry Tear Films," now U.S. Pat. No. 11,464,672, issued on Oct. 11, 2022, which is a national phase application of PCT Application No. PCT/US2019/034008 filed May 24, 2019, entitled "Systems and Methods for Generating and Applying Biomimicry Tear Films," which claims the benefit of U.S. Provisional Application No. 62/679,154, filed Jun. 1, 2018, entitled "Systems and Methods for Generating and Applying Biomimicry Tear Films," all of which are incorporated herein by reference in their entireties.

This application also claims the benefit of U.S. Provisional Application No. 63/389,309, filed Jul. 14, 2022, entitled "Systems and Methods for Administering Fluid Compositions," which is incorporated by reference herein in its entirety.

TECHNICAL FIELD

The present description relates generally to systems and methods for administering fluid compositions.

BACKGROUND

A healthy tear film is integral to the overall health of eyes and vision. The tear film covers an ocular surface of the eye including the cornea in a thin fluid layer approximately 3 μm thick and approximately 3 μL in volume. The tear film thus functions as an interface between the ocular surface and an outside environment, functioning to polish the corneal surface, mechanically trap and flush out foreign bodies and chemicals, inhibit growth of microorganisms, and reduce surface friction associated with eyelid blinking and eye movement.

Dry eye syndrome (DES) is a condition characterized by eyes, which do not produce enough tears, or produce low-quality tears (that is, tears which fail to form a stable tear film or which evaporate too fast). Symptoms of DES include eye redness, irritation, itchiness, pain, swollen eyelids, blurred vision, and eye discomfort from contact lenses. DES is highly prevalent, and constitutes a primary reason for eye doctor visits. Nearly half of Americans aged 18 and older experience symptoms of DES. Further, DES is typically chronic, often requiring long-term management.

There is thus great needs for treatment methods and associated apparatus to improve the condition and comfort of the eyes.

SUMMARY

The majority of DES diagnoses are characterized as either evaporative dry eye, in which lipid deficiencies cause the tear film to evaporate at a faster than normal rate, or aqueous tear deficiency, where insufficient tear volume is produced. Treatments typically target one of these two types of DES. One example treatment includes adding artificial tear drops (e.g., omega-3 or mineral oil enriched artificial tear drops or emulsions) to increase the tear volume. A second example involves blocking tear ducts temporarily using small silicone, or gel-like, plugs to retain tears in the eye. A third example instead blocks tear ducts permanently by a surgical procedure to retain tears in the eye. A fourth example includes adding eye drops or ointments to decrease inflammation on or around the eye. In a fifth example, DES caused by a blockage of the Meibomian gland (MG) has been treated using a device which simultaneously delivers a vectored thermal pulse, or a combination of heating and massaging, to an interior of the eyelid, and a therapeutic motion to an exterior of the eyelid. As a sixth example, neurostimulation may be utilized to increase tear production in the aqueous layer of the tear film.

However, it is herein recognized that there are numerous shortcomings to the aforementioned treatments. For instance, the small silicone plugs may be uncomfortable and may cause inflammation. As another example, surgical procedures may be expensive and may result in complications. Treatments based on eye drops and ointments may be messy and inconvenient, as excessive liquids or ointments may result in temporarily blurred vision, stained clothing, and/or ruined makeup. Omega-3 or mineral oil enriched artificial tear drops or emulsions may have difficulty forming a stable tear film on the cornea of the eye, due to an inability of such drops or emulsions to adhere to the surface of the cornea in an even manner. The device-based treatment described above only treats clogged MGs, is costly (e.g., up to $1500 per treatment), does not offer much in the way of improvement for individuals with significant loss of the MG, and relief is typically of a limited duration (e.g., from one week to 3-6 months). Neurostimulation as mentioned above may increase tear production, but suffers from a failure to stimulate lipid or mucin production, thereby limiting the utility thereof.

The inventors have identified the above problems and herein provide systems and methods to at least partially address them.

Various embodiments of systems and methods for treating DES are provided. More particularly, Systems and methods for generating and applying biomimicry tear films that mimic the natural tear film layers are provided herein.

Tear film is made up of three layers secreted by various glands and tissues. Furthest removed from the cornea is a lipid layer, or oil layer. The lipid layer functions to seal and stabilize the tear film, thereby helping to reduce tear evaporation. A middle aqueous layer functions to lubricate the eye, wash away debris, and prevent infection. Another layer closest or adjacent to the cornea, is a mucin layer. The mucin layer allows the aqueous layer to spread evenly over the surface of the cornea, helps the eye to remain moist and lubricated, provides the cornea with nourishment, and helps tears adhere to the surface of the cornea.

In various embodiments, the generated and applied biomimicry tear films include multiple layers, which can be optically transparent, ultrathin, biomechanically stable, evenly and smoothly conformal to the cornea surface. In one example, the biomimicry tear films include an outer biomimicry lipid layer, a middle biomimicry aqueous layer, and an inner biomimicry adhesive layer. The layer thickness of these one or more layers generated and applied can range from a few molecular to a few microns o even up to 250 microns.

In various embodiments, the biomimicry lipid layer that mimics the natural lipid layer of natural tear film, which can comprises one or more lipophilic compositions and functions as a lipophilic barrier to prevent tear evaporation. In various embodiments, the biomimicry lipid layer comprising one or more biomimicry tear components selected from a group comprising phospholipids (e.g., sphingomyelin, phosphatidylcholine), cholesterols, cholesterol esters, triglycerides, castor oil, mineral oil, fish oil, flaxseed oil, other naturally or synthetic oil, unsaturated lipids, hyaluronic acid, soy oil, petrolatum, waxes, anhydrous lanolin, lanolin, oleaginous ingredients, liposomes, ophthalmic emollients, demulcents, and synthetic materials which may be used to substitute/replace the natural human lipid layer. Further, the lipid composition may include one or more lipid-soluble vitamins (e.g., vitamin E, vitamin A).

In various embodiments, the biomimicry aqueous layer that mimics the natural aqueous layer of natural tear film, which functions to lubricate the eye, wash away particles, provide nutrition and prevent infection. In various embodiments, the biomimicry aqueous layer comprises an aqueous solution. In various embodiments, the biomimicry aqueous layer comprises an isotonic aqueous solution and may include one or more biomimicry tear components including but not limited to water and one or more electrolytes (e.g., sodium, potassium, chloride, bicarbonate, magnesium, and calcium). In various embodiments, the aqueous layer may comprise antibacterial substances such as water-soluble antibiotics such as lincomycin, neomycin, spectromycin and penicillin, and water-soluble proteins such as lysozyme, betalysin and lactoferrin, that have antibacterial properties In various embodiments, the biomimicry adhesive layer that mimics the natural adhesive layer, which functions to adhere to or interact with the lipophilic cornea surface as a thin and smoother layer that for layering on the hydrophilic biomimicry aqueous layer. In various embodiments, the biomimicry adhesive layer comprising bipolar molecules that are lipophilic on one end for adhering to the cornea surface and hydrophilic on the other end for receiving or layering on the biomimicry aqueous layer. In various embodiments, the adhesive layer comprising amphipathic molecule that has both a hydrophilic and hydrophobic component, such as a phospholipid and membrane protein. In various embodiments, the adhesive layer comprising composition that may include one or more biomimicry tear components comprising membrane-spanning mucins (e.g., MUC5AC) and/or mucin-like proteins or molecules. The mucins or mucin-like proteins or molecules may contain a cytoplasmic domain (e.g., a hydrophilic domain which may reach inside a corneal epithelial cell), a membrane-spanning domain (e.g., a hydrophobic domain which may span a membrane of the corneal epithelial cell), and an extracellular domain (e.g., a hydrophilic domain which may remain outside of the cornea).

Various systems and methods can be used to generate and apply biomimicry tear films.

In some embodiments, a method and a device for treating DES involves generating small droplets of artificial tears or components of artificial tear and applying the produced small droplets of artificial tears or artificial tear components to form a conformal layer on the surface of eyes to serve as artificial tears or biomimicry tears. In various embodiments generating small droplets of artificial tears or artificial tear components comprising vaporizing a liquid, solid or semi-solid material (e.g., at the time of applying the artificial tear to the cornea), such that there is no premixing of the respective compositions of the different tear film layers prior to application of the artificial tear to the eye.

In various embodiments, the device includes an atomizer or nebulizer. In various embodiments, the small droplets of tears or tear components are micrometer sized droplets. In various embodiments, the method includes the steps of generating and depositing multiple layers of materials on the surface of the eyes, layer by layer (e.g., within a threshold amount of time of each other (e.g., after the previous layer is formed and before it disintegrates due to other disruptions (e.g., due to blinking, evaporation, or draining away into the tear duct))). In various embodiments, the method includes the steps of: (1) Using the device to nebulize a first composition to form a first vapor containing small particles (e.g., micro-sized particles) of the first composition, delivering the first vapor to the eyes to form a first conformal layer of material on the surface of the eyes. In various embodiments, the first composition comprises one or more compounds that adhere to cornea surfaces ("Adhesive Material"). In various embodiments, the first composition comprises a compound selected from the group consisting of hydrophilic compound, amphiphilic compound, amphoteric compound. In various embodiments, the first composition may additionally comprise one or more compounds, materials or cells that help to the nourish, heal the cornea, or treat the cornea or the entire eye, such as stem cells, minerals, antioxidants (e.g., vitamin E), vitamins (e.g., vitamin A), anti-inflammatory compounds (e.g., steroid, NSAID), antibodies or anti-microbial. (2) Using the device to nebulize a second composition to form a second vapor containing small particles (e.g., micro-sized particles) of the second composition, delivering the second vapor to the eyes to form a second conformal layer of material on the surface of the eyes over the first conformal layer. In various embodiments, the second composition comprises an aqueous solution such as isotonic buffer solution and over the counter artificial tear. (3) Using the device to nebulize a third composition to form a third vapor containing small particles (e.g., micro-sized particles) of the third composition, delivering the third vapor to the eyes to form a third conformal layer of material on the surface of the eyes over the second conformal layer. In various embodiments, the third composition comprises hydrophobic materials. In various embodiments, the third composition may comprise flaxseed oil, DHA, omega-3 fatty acid, or materials derived from flaxseed oil, DHA, and omega-3 fatty acid.

Comparing with traditional eye drops or ointment, the new method provides a more uniform, much thinner and more stable tear film that is similar to real tear. In addition, it can be more enriched with electrolytes and proteins like in real tear do or utilize high viscosity materials that currently not used in eye drops. The optical transparency is still fairly good with a very thin layer thickness, for example from a molecule to submicron.

In some embodiments, a device can generate vapors and form coatings being utilized for biomimicry tears. The device includes: an atomization module which can turn materials from liquid to vapor; a reservoir module that contains the liquid materials; a vapor emit/spray module, like nozzle, that direct vapors to from coating on the target objects; a power module and some electronics to switch the device on and off, etc. In some embodiments, the atomization function can utilize ultrasonic, piezoelectric, or Micro-Electro-Mechanical-Systems (MEMS), other mechanism. In some embodiments, the device can work with liquid materials with various viscosities, from 1 cp (e.g., water) to 200 cp (e.g., oil-like fluid). In some embodiments, the droplet size can be from sub-micron, 1 micron to 100 um.

In some embodiments, biomimicry tears consist of one or more layers of materials, which can form a conformal coating on the surface of the eye. Like real human tears, the materials of layers can include: an Adhesive layer: It can be a high molecular weight material, a single cell layer, or stem cell, a protein layer that provides adhesion for biomimicry tears on corneal epithetical surface. This layer is hydrophilic; an Aqueous layer: It can be a watery layer that provides moisture, nourishment and protection to the cornea; and an Oil layer: A layer on top of the aqueous layer to hold the shape of the tear film stably (by provide enough surface tension) and protection to prevent aqueous layer evaporate too quickly. In some embodiments, each material will be packaged individually with multiple of such packages in the reservoir module. Because the new applying method, a coating of thin layers, the biomimicry tears can a mixture liquid that offers the functions of all those three layers, adhesion, nourishment, lubrication and protection. In some embodiments, each layer thickness can be from a single molecule layer to a few microns. In some embodiments, ingredients in the film materials can include but not limited to Carboxymethylcellulose sodium, dextran, glycerin, hypromellose, polyethylene glycol 400 (PEG 400), polysorbate, povidone, or propylene glycol, etc.

In some embodiments, package of the materials includes the following features: (a) the liquid materials can be packaged into disposable capsules that placed in the reservoir module. Once the liquids are used, the capsules will be replaced; and (b) The reservoir module can be designed for multiple usages as well. It can contain one or a few cavities for various liquid materials which can be refilled. In some embodiments, one or more replaceable and disposable capsules includes additional ingredients, such as medication, nourishments, lubricants, that are added to or premixed with a respective composition from another capsule inside a processing chamber of the dispensing apparatus (e.g., an atomizer), before the composition is dispensed onto the surface of the cornea or a previously applied tear film layer.

In some embodiments, a camera module can be added on the device to capture the image of the eye before and after coating biomimicry tears to monitor the syndromes of dry eye disease. In some embodiments, the camera monitors the application of each artificial tear film layer, to ensure that a previous layer is properly formed (e.g., with sufficient coverage and thickness) before the composition for the next layer of the artificial tear is dispensed onto the eye.

In some embodiments, a method of treating dry eye, includes: sequentially applying a plurality of distinct compositions to a surface that corresponds to a cornea of an eye (e.g., the convex surface of the cornea or a concave surface of a substrate (e.g., a coated MEMS device or contact lens) used to deliver the preformed multilayer artificial tear film on to the cornea), wherein the plurality of distinct compositions include at least a first composition, a second composition, and a third composition, and sequentially applying the plurality of distinct compositions to the surface includes: applying a first amount of the first composition to the surface that corresponds to the cornea of the eye, wherein the first amount of the first composition is distributed on the surface to form a first film layer of the first composition; applying a second amount of the second composition to the first film layer of the first composition that has been formed on the surface that corresponds to the cornea of the eye to form a second film layer of the second composition; and applying a third amount of the third composition to the second film layer of the second composition to form a third film layer of the third composition over the second film layer of the second composition, wherein the first film layer and the third film layer respectively correspond to a lipid layer and a mucin layer of a biomimicry tear film for the eye and the second film layer corresponds to an aqueous layer of the biomimicry tear film for the eye.

In some embodiments, sequentially applying the plurality of distinct compositions to the surface that corresponds to the cornea of the eye includes: generating a respective mist for each of the first composition, the second composition, and the third composition; and sequentially exposing the cornea of the eye to the respective mist for each of the first composition, the second composition, and the third composition.

In some embodiments, sequentially applying the plurality of distinct compositions to the surface that corresponds to the cornea of the eye includes: forming the mucin layer of the biomimicry tear film directly on the cornea using the first composition; forming the aqueous layer of the biomimicry tear film on the mucin layer of the biomimicry tear film using the second composition; and forming the lipid layer of the biomimicry tear on the aqueous layer of the biomimicry tear film using the third composition.

In some embodiments, the first composition includes mucin or mucin-like proteins or molecules; the second composition includes water and one or more electrolytes; and the third composition comprises one or more of phospholipids, cholesterols, cholesterol esters, triglycerides, castor oil, mineral oil, fish oil, flaxseed oil, unsaturated lipids, hyaluronic acid, soy oil, petrolatum, waxes, anhydrous lanolin, lanolin, oleaginous ingredients, liposomes, ophthalmic emollients, demulcents, and synthetic materials.

In some embodiments, prior to applying each of the first composition, the second composition, and the third composition, the method includes adjusting a respective dispensing parameter of an atomizer used to apply the first composition, the second composition, and the third composition in accordance with user input (e.g., through built-in input interface on the dispensing device, or an application on a mobile device, or according to instructions from a remote server).

In some embodiments, the respective dispensing parameter includes a parameter selected from a dispensing quantity (e.g., different quantities of different compositions are determined based on user input regarding the reason for the patient's dry eye and the conditions of the patient's natural tears), a dispensing duration (e.g., different durations are determined for different compositions based on their viscosities, and the quantities that need to be dispensed), a dispensing rate (e.g., based on user input regarding user tolerance and comfort, and the viscosities of the compositions), a dispensing energy level (e.g., based on characteristics of the compositions and patient comfort levels), a droplet size (e.g., based on characteristics of the compositions and film formation requirements for the different compositions), a spray speed (e.g., based on characteristics of the compositions (e.g., evaporation rate and film formation requirements)), a spray angle (e.g., based on characteristics of the cornea (e.g., presence of wound, shape, etc.)), a spray distance (e.g., based on characteristics of the compositions and the droplet sizes, etc.), a coverage area size (e.g., based on the receiving subject (e.g., coverage area may be smaller (e.g., with shorter spray distance and slower spray speed) when spraying the mucin layer directly on the cornea, and may be greater when spraying the lipid layer on the aqueous layer (e.g., with greater spray distance and greater spraying speed)) of the sprays), and equivalents thereof.

In some embodiments, the method includes: prior to applying a respective one of the first composition, the second composition, and the third composition, adding one or more additional ingredients to the respective one of the first composition, the second composition, and the third composition in accordance with one or more customization instructions (e.g., received from the user through an application or remote server). In some embodiments, the one or more additional ingredients include one or more medication (e.g., anti-inflammation medication, antibodies, etc.). In some embodiments, the one or more additional ingredients include one or more vitamins (e.g., supplements that nourishes, increases comforts, etc.).

In some embodiments, the method includes selecting the respective one of the first composition, the second composition, and the third composition to add the one or more additional ingredients based on one or more properties of the additional ingredients (e.g., depending on the solubility and interactivity between the additional ingredients and each of the compositions).

In some embodiments, the first composition, the second composition, and the third composition are applied using a single device containing respective composition chambers for each of the first, second, and third compositions, and a single dispensing apparatus, wherein the single dispensing apparatus is configured to adjust a dispensing parameter (e.g., dispensing speed, mixing time and speed, droplet size, etc.) based on which composition chamber of the single device is currently connected to the single dispensing apparatus. In some embodiments, the additional ingredients are included in additional chambers of the single device and may be exchanged depending on needs of the patients.

In some embodiments, wherein the first composition, the second composition, and the third composition are applied using a single device that dispenses the first, second, and third compositions using respective dispensing apparatus with distinct dispensing parameters corresponding to the first, second, and third compositions. For example, each composition has its own dispensing nozzle and optionally mixing chambers that is attached to the single device at the time of use.

In some embodiments, sequentially applying a plurality of distinct compositions to a surface that corresponds to a cornea of an eye includes: receiving, via a controller (e.g., implemented by one or more processors and memory (or another non-transitory computer-readable medium) storing instructions, the instructions, when executed by the one or more processors, cause the processors to perform the operations of the methods described herein) of an atomizer, instructions pertaining to atomizing one of the first composition into a first spray mist, the second composition into a second spray mist, and the third composition into a third spray mist; routing one of the first composition, the second composition and the third composition into a process chamber of the atomizer based on the instructions; commanding, based on the instructions, a speed of a motor of an air pump to route an air flow into the process chamber; and where air and one of the first composition, the second composition and the third composition exit the process chamber as one of the first spray mist, the second spray mist and the third spray mist, respectively, for application to the cornea of the eye (e.g., directly on the surface of the cornea or on a previously applied film layer on the surface of the cornea).

In some embodiments, the instructions pertaining to atomizing one of the first composition, the second composition and the third composition are received at the controller from a customization application communicatively coupled to the controller (e.g., through a wireless connection or a wired connection).

In some embodiments, air and one of the first composition, the second composition and the third composition exit the process chamber via a nozzle, where a radius of the nozzle is adjustable; and wherein the controller further receives instructions for adjusting the radius of the nozzle as a function of the first composition, the second composition and the third composition (e.g., in accordance with respective viscosities of the first, second, and third compositions).

In some embodiments, the set of instructions pertain to one or more of a desired amount of the composition to be applied, a desired sequence of application of compositions stored in the plurality of composition chambers, a desired droplet size of the spray mist, and a desired duration of application of the spray mist.

In some embodiments, various additional features and details are set forth with respect to the methods, systems, apparatuses disclosed herein and are combinable with the above method, and are not repeated in the interest of brevity. In some embodiments, systems, apparatuses, atomizers, and controllers are implemented to perform the methods described herein.

In various embodiments, generating and applying biomimicry tear films comprising generating mist of micro droplets using a micronizer/nebulizer/atomizer and applying to the cornea form the one or more layers or sublayers of biomimicry tear films. In various embodiments, microelectromechanical systems (MEMS) are used to print the one or more layers or sublayers of biomimicry tear films onto the cornea surface. In various embodiments, generating and applying biomimicry tear films comprising preforming the one or more layer of biomimicry tear films and applying the preformed biomimicry tear films to the cornea directly similar to wearing a contact lens.

In one example, a method for creating a biomimicry tear film on a cornea may comprise forming a multilayered tear film that may include forming a first smooth conformal biomimicry tear film layer on the cornea. In some examples, forming the multilayered tear film may further include forming a second smooth conformal biomimicry tear film layer on the first smooth conformal biomimicry tear film layer. In some examples, forming the multilayered tear film may further include forming a third smooth conformal biomimicry tear film layer on the second smooth conformal biomimicry tear film layer.

In another example, a system for creating a biomimicry tear film on a cornea may comprise a first composition for forming a first layer of the biomimicry tear film, a second composition for forming a second layer of the biomimicry tear film, a third composition for forming a third layer of the biomimicry tear film, and an atomizer for atomizing and spraying the first composition, the second composition, and the third composition to create the biomimicry tear film on the cornea.

In another example, an apparatus for creating a biomimicry tear film on a cornea may comprise an air pump operable via a motor, at least one composition chamber, and a controller that may store user-defined instructions for operating the air pump to atomize and spray a first composition to form a first layer on the cornea that may comprise an adhesive layer of the biomimicry tear film, a second composition to form a second layer on the first layer that may comprise an aqueous layer of the biomimicry tear film, and a third composition to form a third layer on the second layer that may comprise an oil layer of the biomimicry tear film.

In another example, a method for treating dry eye syndrome using an atomizer may comprise routing a composition stored in a composition chamber of the atomizer into a process chamber of the atomizer via a composition pathway, routing an air flow from an air pump that may include a motor into the process chamber via an air pathway, controlling a speed of a motor and in turn a rate of the air flow based on the composition stored in the composition chamber, establishing an exit pathway where a combination of the composition and the air flow may exit the atomizer as a spray mist, and applying the spray mist to a cornea of a user of the atomizer.

In another example, a method for treating dry eye syndrome may comprise receiving, via a controller of an atomizer, instructions pertaining to atomizing one of a first composition into a first spray mist, a second composition into a second spray mist and a third composition into a third spray mist, routing one of the first composition, the second composition and the third composition into a process chamber of the atomizer based on the instructions, commanding, based on the instructions, a speed of a motor of an air pump to route an air flow into the process chamber, and where air and one of the first composition, the second composition and the third composition may exit the process chamber as one of the first spray mist, the second spray mist and the third spray mist, respectively, for application to a cornea of a user of the atomizer.

In another example, an atomizer system for applying a spray mist to a cornea or skin may comprise a remote computing device implementing a customization application, an atomizer that includes a plurality of composition chambers, an air pump operable via a motor, a process chamber that may receive a composition from one of the plurality of composition chambers at a time and an air flow from the air pump, a nozzle that may receive a mixture of the composition and the air flow for generating the spray mist, and a controller of the atomizer that may receive a set of instructions for applying the spray mist from the customization application.

In another example, an atomizer for administering a spray mist to a cornea or skin may comprise a removable head module that includes a composition chamber and a process chamber, the process chamber fluidically coupled to the composition chamber via a composition passage, a body module that may include an air pump and a motor of the air pump for supplying air to the process chamber via an air passage, a needle valve assembly including a needle and a nozzle, the needle valve assembly included in the process chamber, and a controller included in the body module storing instructions for adjusting a speed of the motor as a function of a viscosity of a composition included in the composition chamber.

In another example, an atomizer for administering a spray mist to a cornea or skin may comprise a composition cavity included in a head module of the atomizer, wherein the composition cavity includes a first composition chamber having a first valve, a second composition chamber having a second valve, and a third composition chamber having a third valve, a process chamber included in the head module that may independently receive a first composition from the first composition compartment when the first valve is open, a second composition from the second composition compartment when the second valve is open, and a third composition from the third composition compartment when the third valve is open, a body module mechanically coupled to the head module, the body module including an air pump operable via a motor for supplying an air flow to the process chamber, and a nozzle fluidically coupled to the process chamber where one of the first composition, the second composition, and the third composition may respectively exit the atomizer as one of a first spray mist, a second spray mist, and a third spray mist.

In another example, an atomizer for administering a spray mist onto a cornea or skin may comprise a head module, a body module positioned below the head module with respect to a vertical axis of the atomizer, the body module removably coupled to the head module, a composition chamber included in the head module, a process chamber included in the head module, the process chamber positioned below the composition chamber with respect to the vertical axis, the process chamber fluidically coupled to the composition chamber via a composition passage, an air pump with a motor positioned in the body module, where the air pump may be fluidically coupled to the process chamber via an air passage of the process chamber that may extend along the vertical axis from the head module to the body module, a needle valve assembly included in the process chamber, the needle valve assembly including a needle and a nozzle with an orifice, the orifice positioned at a front frame of the head module and where the needle valve assembly may extend along a front-to-back axis of the atomizer perpendicular to the vertical axis, a needle valve cover mechanically coupled to the needle, and a first spring connected to the needle valve cover that may bias the needle to a fully seated position in the nozzle, an atomization actuator, a link rod extending along the vertical axis from the head module to the body module, the link rod selectively mechanically coupled to the atomization actuator, a hinged connector with a connecting element positioned along the front-to-back axis of the atomizer that may fit into a link rod groove of the link rod, where movement of the link rod in a downward direction with respect to the vertical axis may rotationally mechanically engage the hinged connector with the needle valve cover to compress the first spring and unseat the needle from the fully seated position in the nozzle, a printed circuit board included in the body module, wherein the downward direction of movement of the link rod may mechanically engage the link rod with the printed circuit board to activate the motor to produce an air flow to the process chamber, and wherein a composition stored in the composition chamber may flow through the process chamber and may exit the orifice as the spray mist when the needle is unseated from the fully seated position while the motor is activated.

To achieve the end of generating and applying biomimicry tear films that mimic the natural tear film layers, atomizer systems are herein provided which may atomize one or more compositions that include one or more biomimicry tear components into droplets. The droplets may then be applied to a cornea of an eye as a spray mist to deliver one or more film layers that mimic natural tear film layers, and which coat a surface of the cornea. The atomizer may include a head module and a body module, wherein the head module may be detachable from the body module in some examples. That is, the head module may be interchangeable with another head module in some examples. The head module may include one or more composition chambers which may be respectively provided with the one or more compositions. The body module may include an air pump in one example. A process chamber included in the head module may receive an air flow from the air pump and a composition from the one or more composition chambers. The process chamber may be fluidically coupled to a nozzle, whereby a resultant mixture of air and the composition in the process chamber may exit the atomizer for spraying onto the eye of a user of the atomizer. A flow rate of the air may be determined by a speed of a motor of the air pump. One or more of the speed of the motor of the air pump and a radius of the nozzle may be adjusted as a function of a viscosity of the composition. As such, the atomization of a selected composition may be controlled as a function of a viscosity of the particular composition selected for atomizing and spraying onto the cornea of the user of the atomizer.

The atomization as described above may have several advantages in addition to those already detailed (e.g., interchangeability of the head module, composition-based control of the atomization). First, the atomization and spraying process may be carried out without heating of the composition. It may be understood that the absence of heating may be advantageous as heating may compromise effectiveness and quality of a resultant spray mist, or may evaporate a given composition. Second, the atomization may be conducted such that a pressure of the spray mist is minimized for applying the spray mist to the eye, which may avoid irritation to the eye receiving the spray mist. Thus, the atomizers of the present disclosure may improve upon aerosol and pump-based sprays, such as those utilized for non-ophthalmic purposes (e.g., fragrance, skincare, cosmetic products), which lack control of both pressure and droplet quantity, as an operator's action of pressing or pumping may vary in force. Third, the atomizers of the present disclosure may apply multiple compositions in a sequential manner, where each of the multiple compositions may vary substantially in viscosity. Some sprays, such as ultrasonic-based sprays (e.g., facial or room humidifiers) may be limited to liquids of a small range of viscosity (e.g., water and other low viscosity liquids). The atomizer systems of the present disclosure increase such a viscosity range, which is particularly advantageous for an atomizer designed to atomize and spray compositions corresponding to the layers of natural tear film, where such layers range in viscosity from around 1 mPa to around 10000 mPa.

Some embodiments disclose a device (e.g., an apparatus) that can be used for delivery of ophthalmic fluids, nasal solutions, and/or fluid-based vaccines to a person's sensory organs, such as the eye, nose, and/or ear.

In accordance with some embodiments, a device for delivering ophthalmic fluids and/or fluid-based vaccines includes a housing. The housing includes a first end and a second end opposite to the first end. The first end includes an opening. In some embodiments, the device includes a compartment (e.g., a region, an area, etc.) positioned at (e.g., next to, adjacent to, proximate to) the first end. In some embodiments, the compartment is capable of holding a fluid (e.g., a liquid). For example, in some embodiments, the fluid is contained in a liquid reservoir that is positioned in the compartment. The device includes an air pump positioned within (e.g., inside) the housing, at (e.g., toward) the second end. The device includes an actuator (e.g., an electric actuator) positioned within the housing, between the compartment and the air pump. The actuator includes an extendible (and retractable) piston that is configured to execute a translational movement. During device operation, the actuator causes the piston to extend towards the liquid reservoir and exert a force on the liquid reservoir. The force causes the fluid to be expelled from the liquid reservoir at the first end. The air pump is configured to atomize the fluid at the first end as it is expelled from the liquid reservoir.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

FIG. 17 illustrates a device that can be used to deliver solutions and/or fluid-based vaccines, according to some embodiments.

FIGS. 18A and 18B illustrate an actuator, in accordance with some embodiments.

FIGS. 19A and 19B illustrate placement of a liquid reservoir into a device, in accordance with some embodiments.

FIGS. 20A and 20B illustrate exemplary designs of a nozzle according to some embodiments.

FIG. 21 illustrates operation of a device according to some embodiments.

FIG. 24 illustrates a flowchart for an exemplary method of administering a fluid in accordance with some embodiments.

DETAILED DESCRIPTION

The following description relates to systems and methods for generating and applying tear film layers which mimic biological tear film layers to a cornea of an eye, thereby forming a multilayered tear film. An atomizer is provided which atomizes and sprays a composition or compositions that can include biomimicry tear components to form one or more film layers on the cornea. The atomizer may be adapted to deliver compositions of varying viscosities. The atomizer disclosed herein may not be limited to atomizing and spraying compositions that mimic biological tear film layers, but may be adaptable to other applications including but not limited to the applying of lotions, essences, creams, etc., to a desired skin location without departing from the scope of this disclosure.

Figure 1A:
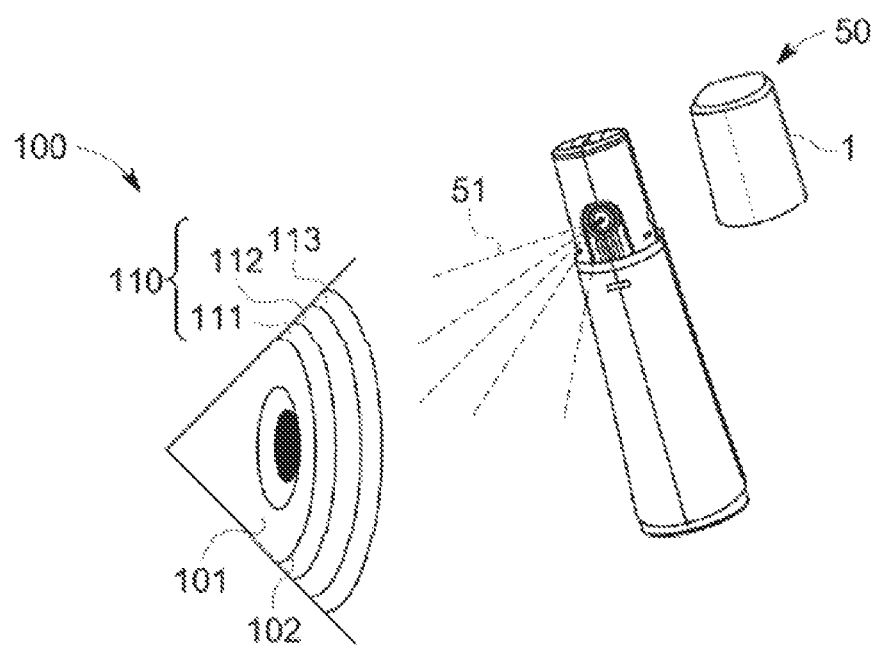
FIG. 1A shows an atomizer of the present disclosure delivering a film layer in a form of a spray mist to an eye.

Referring now to FIG. 1A, it depicts a film layer being delivered in a form of a spray mist 51 to an eye 100. As illustrated, a device such as an atomizer 50, also referred to herein as handheld atomization apparatus 50, still further also referred to herein as programmable atomizing device 50, generates the spray mist 51 by way of an atomization. Atomizer 50 may include a cap 1, in some examples. Details of atomizer 50 are discussed in greater detail below. In one example, the atomization may be via air (e.g., air spray) atomization. However, other forms of atomization including but not limited to ultrasonic atomization, pressure (e.g., airless, air-assisted airless) atomization, centrifugal (e.g., rotary) atomization, or electrostatic atomization may be used without departing from the scope of this disclosure. In some examples, the device may be of an alternative construction, such as a nebulizer or an aerosolizer, for generating the spray mist 51 via nebulization or aerosolization, respectively. In still further examples, the device for generating the spray mist may be a micronizer/nebulizer/atomizer, for generating the spray mist 51 via micronization. The eye 100 as depicted includes a cornea 101 and a tear film 110 interfacing with a surface 102 of the cornea 101. The tear film 110 includes a mucin layer 111, an aqueous layer 112, and a lipid or oil layer 113. Herein, "mucin" may refer to a family of relatively high molecular weight, heavily glycosylated proteins, or glycoconjugates, produced by epithelial tissues.

The atomizer 50 may atomize one or more compositions into small droplets, each of which may include one or more biomimicry tear components, and administer the atomized composition(s) as the spray mist 51 to deliver/form one or more ultrathin (e.g., 1 μm in thickness or less), uniform, smooth, and conformal film layers to coat the surface 102 of the cornea 101. Discussed herein, "uniform" and "smooth" may be interchangeably used to describe a coverage of any threshold area of the surface 102 of the cornea 101 (e.g., a total surface area, less than the total surface area) by a film layer of substantially similar thickness and smoothness, or in other words, unchanging in form or character. Discussed herein, "conformal" may be used to describe the coverage of the total surface area of the surface 102 of the cornea 101 by the film layer being complete and/or conforming to a shape of the surface 102 of the cornea. As such, a biomimicry tear film may be formed, which may include one or more stable layers that mimic and function like various film layers (e.g., the mucin layer 111, the aqueous layer 112, the lipid or oil layer 113) of the tear film 110.

The one or more compositions may be composed of a liquid, solid, or semisolid material. In some examples, the biomimicry tear film as formed may include an adhesive layer, or mucin layer, having a similar composition and function to the mucin layer 111. In some examples, the biomimicry tear film as formed may include an aqueous layer having a similar composition and function to the aqueous layer 112. In some examples, the biomimicry tear film as formed may include an oil layer, or lipid layer, having a similar composition and function to the lipid layer 113.

In a first example, a first composition (e.g., aqueous composition) may be atomized and sprayed to form an aqueous layer on the surface 102 of the cornea 101, which may mimic the aqueous layer 112 of the tear film 110. A second composition (e.g., lipid composition) may then be atomized and sprayed to form an oil layer on the surface 102 of the cornea 101, where the oil layer may mimic the lipid layer 113 of the tear film 110.

In a second example, a third composition (e.g., adhesive composition or mucin composition) may be atomized and sprayed to form an adhesive layer on the surface 102 of the cornea 101, which may mimic the mucin layer 111 of the tear film 110. The first composition (e.g., aqueous composition) may then be atomized and sprayed to form the aqueous layer on the surface 102 of the cornea 101, which as discussed may mimic the aqueous layer 112 of the tear film 110. The second composition (e.g., lipid composition) may then be atomized and sprayed to form the oil layer on the surface 102 of the cornea 101, which as discussed may mimic the lipid layer 113 of the tear film 110. In such an example, it may be understood that the aqueous layer may be disposed between the adhesive layer and the oil layer.

In a third example, the first composition (e.g., aqueous composition) may be atomized and sprayed to form the aqueous layer on the surface 102 of the cornea 101, which as discussed may mimic the aqueous layer 112 of the tear film 110.

In a fourth example, the second composition (e.g., lipid composition) may be atomized and sprayed to form the oil layer on the surface 102 of the cornea 101, which as discussed may mimic the lipid layer 113 of the tear film 110.

It will be appreciated that, in some embodiments, the first composition, the second composition, and the third composition may be atomized and sprayed to form respective film layers in any desired order. Further, in some examples, each of the first composition, the second composition, and the third composition may include any of the adhesive composition or mucin composition, the aqueous composition, or the lipid composition, without departing from the scope of the present disclosure. However, in some embodiments, the sequential order by which the first composition, the second composition, and the third composition are atomized and applied is predefined in accordance with the specific purpose of the application, such as treating DES and creating a multilayer biomimicry tear film on a cornea, and/or in accordance with the specific properties of the compositions (e.g., required quantities, viscosities, interactivity and reactivity, stability, etc. of the compositions) and is not randomly interchangeable. In some embodiments, the first, second, and third compositions are distinct compositions, that may have no overlap or only a small amount of overlap in ingredients. The first, second, and third compositions are not the same composition or a mixture of the first, second, and third compositions that is physically divided into different volumes.

Discussed herein, the lipid composition may include one or more biomimicry tear components selected from a group comprising phospholipids (e.g., sphingomyelin, phosphatidylcholine), cholesterols, cholesterol esters, triglycerides, castor oil, mineral oil, fish oil, flaxseed oil, unsaturated lipids, hyaluronic acid, soy oil, petrolatum, waxes, anhydrous lanolin, lanolin, oleaginous ingredients, liposomes, ophthalmic emollients, demulcents, and synthetic materials which may be used to substitute/replace the lipid layer 113. Further, the lipid composition may include one or more lipid-soluble vitamins (e.g., vitamin E, vitamin A).

Discussed herein, the aqueous composition may comprise an isotonic aqueous solution and may include one or more biomimicry tear components including but not limited to water and one or more electrolytes (e.g., sodium, potassium, chloride, bicarbonate, magnesium, and calcium).

Discussed herein, the adhesive composition may include one or more biomimicry tear components comprising membrane-spanning mucins (e.g., MUC5AC) and/or mucin-like proteins or molecules. The mucins or mucin-like proteins or molecules may contain a cytoplasmic domain (e.g., a hydrophilic domain which may reach inside a corneal epithelial cell), a membrane-spanning domain (e.g., a hydrophobic domain which may span a membrane of the corneal epithelial cell), and an extracellular domain (e.g., a hydrophilic domain which may remain outside of the cornea 101).

The biomimicry tear film may be applied to treat dry eye syndrome (DES). In contrast to current approaches involving artificial tear drops (deficiencies of which are exemplified below with reference to FIG. 1B), which primarily include applying a mixture of ingredients in a liquid or emulsion form to a cornea of an eye as a "water" or "oil-in-water" type eye drop, the biomimicry tear film may be formed by applying various materials layer by layer the surface 102 of the cornea 101, where each layer may respectively have similar ingredients and properties to the mucin layer 111, the aqueous layer 112, and the lipid layer 113. The layers of the biomimicry tear film may be ultrathin (e.g., from a molecule to a micron in thickness), may be optically transparent, and may offer adhesive, moisturizing, and/or lubricating properties, as well as thermal stability to prevent quick evaporation. Such properties may be naturally present in the tear film 110.

Figure 1B:
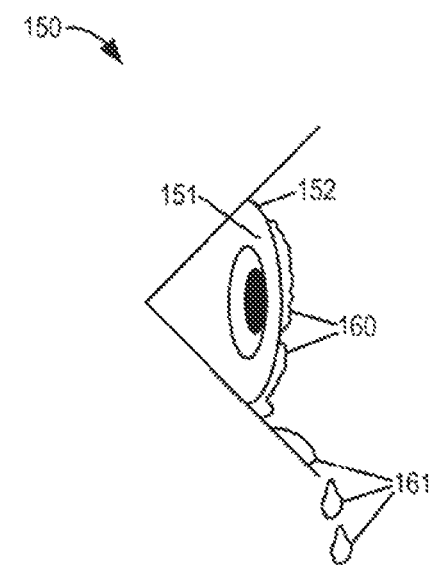
FIG. 1B shows applied artificial tears resulting from an application of conventional artificial tear drops.

Referring now to FIG. 1B, artificial tears 160 applied to an eye 150 are depicted, where the artificial tears 160 result from an application of conventional artificial tear drops. As shown, the artificial tears 160 may adhere to a surface 151 of the cornea 150. However, due to difficulties in controlling a liquid flow during the application of the conventional artificial tear drops, excess artificial tears 161 may result from liquid accumulation in a lower portion of the eye 150, and may drain onto a face of a user of the conventional artificial tear drops.

Returning to FIG. 1A, the biomimicry tear film may be formed via a variety of methods. In addition to the atomization/nebulization/micronization processes described hereinabove, a microelectromechanical systems (MEMS) module 120 may be embedded/implanted within or near the eye 100. The MEMS module 120 may be loaded with one or more biomimicry tear components which may be applied in a similar manner to that known in the art for drug delivery via MEMS. For example, the MEMS module 120 may store instructions executable via a controller thereon to deliver the one or more biomimicry tear components via a plurality of microneedles to form the biomimicry tear film.

As another example of an application of the biomimicry tear film, a preformed biomimicry tear film that include pre-stacked layers corresponding to one or more of layers of the biomimicry tear film. The preformed biomimicry tear film may be directly applied to the cornea 101 in a manner similar to an application of a contact lens, for example. In some examples, the preformed biomimicry tear film may be manufactured with the one or more layers of the biomimicry tear film formed thereon. In some examples, the one or more layers of the biomimicry tear film may be applied to the preformed biomimicry tear film via one of the atomization/nebulization/micronization processes described hereinabove.

Figure 2:
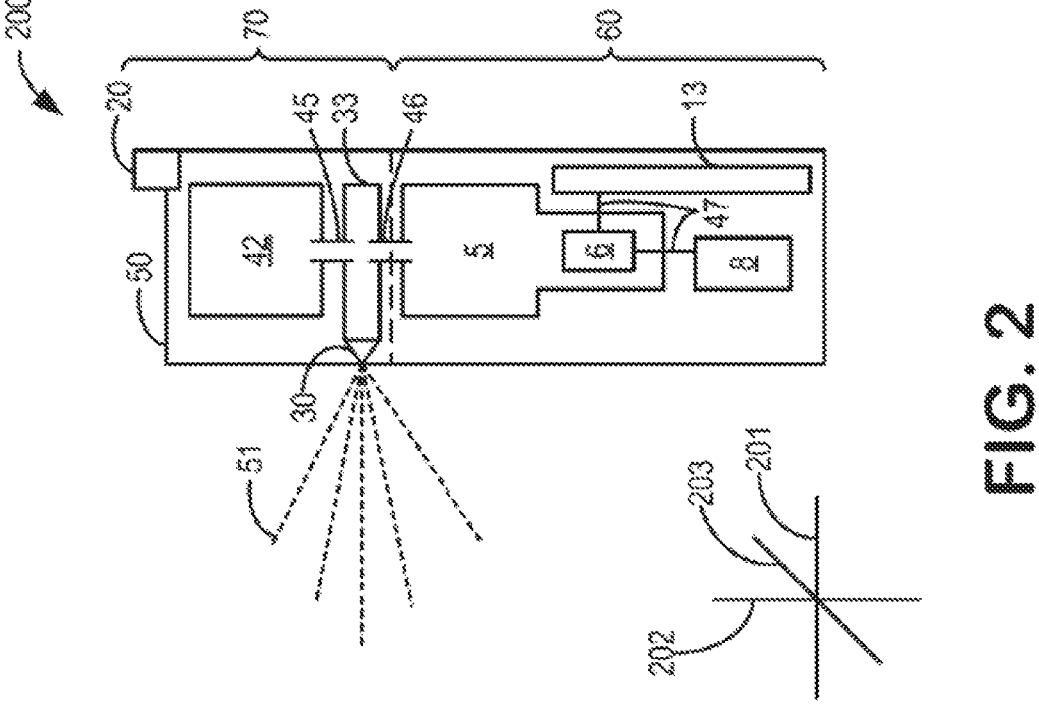
FIG. 2 shows a schematic diagram of the atomizer with a single composition chamber.

Referring now to FIG. 2, a schematic diagram 200 is shown, depicting atomizer 50 including a body module 60 and a head module 70. The atomizer 50 may include a composition chamber 42, or composition compartment 42. The atomizer 50 may atomize a composition (e.g., a liquid) stored in the composition chamber 42 by routing the composition to a process chamber 33 by way of a composition passage 45. An air pump 5 positioned within the body module 60 and operable via motor 6 may route an air flow to the process chamber 33 by way of an air passage 46. The process chamber 33 may be fluidically coupled to a nozzle 30, or micro nozzle 30, by which the composition upon interaction with the air flow is atomized into the spray mist 51. The spray mist 51 may be composed of the composition, and may deliver a biomimicry tear film, such as the biomimicry tear film described above with reference to FIG. 1A, to a cornea of an eye, such as the eye of a human or an animal. In some examples, the human or the animal may be diagnosed with DES. As such, the spray mist 51 may be applied to the cornea to alleviate one or more symptoms associated with DES. Via use of atomizer 50, the spray mist 51 may be applied to the cornea without heating the composition.

Atomizer 50 may further include a printed circuit board (PCB) 13. PCB 13 may be electronically coupled via one of a plurality of wired connections 47 to the motor 6 of the air pump 5 for controlling a speed of the motor. As will be described in greater detail below with reference to FIGS. 8-9C, in some examples PCB 13 may be communicatively coupled to a remote computing device via a network, wherefrom PCB 13 may receive customized instructions for controlling the motor 6 of the air pump 5 and/or other actuators of the atomizer. Head module 70 may include an atomization actuator 20 which may be depressed (or in other examples slid, rotated, or otherwise actuated) by a user for activating the air pump 5 to initiate atomization of the composition. The atomization actuator 20 may selectively mechanically couple to a link rod (not shown at FIG. 2 but see at least FIG. 14) when actuated (e.g., depressed), such that the atomization actuator 20 induces movement of the link rod, causing the link rod to mechanically interact with PCB 13 to activate motor 6 for producing the air flow from air pump 5. Details regarding the atomization actuator 20 and the link rod are discussed below with regard to FIGS. 13-16.

Mutually perpendicular axes define a three-dimensional space for the schematic diagram 200, where a front-to-back axis 201 and a vertical axis 202 define a plane of FIG. 2 and a horizontal axis 203 is normal to the plane of FIG. 2. It will be appreciated that FIGS. 3-4B, 13, 14, and 16 (described in more detail below) are depicted in the same plane as FIG. 2. It will further be appreciated that FIG. 15 (described in more detail below) is depicted in a plane which is perpendicular to the plane of FIG. 2.

The atomization process discussed herein may generate small droplets of liquid with minimal pressure (e.g., within a threshold of zero pressure) to be coated onto the eye. In this way, the eye, being sensitive to excessive pressure, may avoid damage or irritation when using the atomizer 50. A size of the droplets may be selected from a range of a few nanometers to 500 microns in diameter.

Air pump 5 may be operable to produce the flow of air by activation of motor 6. In some examples, motor 6 may be a digital motor. A battery 8 connected to motor 6 via one of the plurality of wired connections 47 may provide power to motor 6. In some examples, battery 8 may be rechargeable. Motor 6 may be operated with an air pump motor speed selected from a range of 100 revolutions per minute (RPM) to 110,000 RPM.

Air pump 5 may pump air into process chamber 33 by way of air passage 46. The speed or rate at which the air flows into process chamber 33 may linearly correlate with the speed of the motor 6 of air pump 5. A resultant mixture of air and the composition received by the process chamber 33 may be received by and routed through nozzle 30, exiting the atomizer as the spray mist 51. The spray mist 51 may then be coated on the eye as one layer of the biomimicry tear film. In some examples, nozzle 30 may have a set length and a set radius, such that nozzle 30 may be optimized for a viscosity of a single composition. However, in other examples, the radius of nozzle 30 may be adjustable so as to function with compositions of varying viscosities.

Accordingly, atomizer 50 may function with compositions with a wide range of viscosities. As an example, the viscosity of the composition may be greater than 1 mPa·s and less than 10000 mPa·s.

Atomizer 50 may use a fixed setting for a plurality of materials. In some examples, the fixed setting may be optimized for a certain viscosity range. In order to achieve optimized performance for each of the plurality of materials, one or more parameters of the atomizer 50 may be adjusted as a function of the viscosity of the composition. The one or more parameters may include the speed of motor 6 of air pump 5, and the radius of nozzle 30. Adjusting the one or more parameters may in some examples result in, or be selected for, adjusting one or more of the size of the droplets of the spray mist 51, an amount of the composition to be atomized, a duration of the atomization, and/or a pressure for delivering the film layer. As such, the size of the droplets of the spray mist 51, the amount of the composition to be atomized, the duration of the atomization, and the pressure for delivering the film layer may be adjusted as a function of the viscosity of the composition.

Achieving a desired level of the atomization may include maintaining a balance of the viscosity of the composition and the amount of the composition (or a flow rate of the composition) with an atomization energy. As such, once the desired level of the atomization has been achieved, a change in any one parameter (e.g., the viscosity of the composition, the amount of the composition, the atomization energy, etc.) may affect the atomization. Such a change may be balanced with an opposing change to return the atomization to the desired level. As an example, a change to the viscosity of the composition may require a corresponding change to the atomization energy (e.g., increased or decreased air flow rate). As another example, a change to a flow rate of the composition may require a corresponding change to the atomization energy (e.g., increased or decreased air flow rate).

While FIG. 2 depicts atomizer 50 with air pump 5, as mentioned above in other examples atomizing a composition may be via ultrasonic atomization, pressure (e.g., airless, air-assisted airless) atomization, centrifugal (e.g., rotary) atomization, or electrostatic atomization, without departing from the scope of this disclosure. The atomization energy for the atomization may be derived from various energy sources, depending on a type of the atomization. As an example, the energy source for air atomization may be an air spray, or an air pressure (e.g., from an air pump, such as the air pump 5). In another example, the energy source for pressure atomization may be from pressurizing the composition. As yet another example, an energy source for centrifugal atomization may be a centrifugal force (e.g., achieved via a motor).

In some examples, the atomizer 50 may be a handheld device. However, in other examples, the atomizer 50 may be stationary. In such examples, the atomizer 50 may be affixed to a horizontal surface, such as a desktop, or the atomizer 50 may be affixed to, or hang from, a vertical surface, such as a wall.

The composition chamber 42 may be sized to hold a particular volume of the composition. In some examples, the volume of the composition chamber 42 may be between 0.5 mL and 3 mL. In some examples, the volume of the composition chamber 42 may be between 0.5 mL and 1 mL. In some examples, the volume of the composition chamber 42 may be between 1 mL and 2 mL. In some examples, the volume of the composition chamber 42 may be between 2 mL and 3 mL.

In some examples, the composition chamber 42 may directly receive a composition from another external container. For example, a liquid composition may be poured or otherwise transferred directly into the composition chamber for storage therein. In other examples, the atomizer 50 may be refilled by removing and replacing one or more pre-filled vials, capsules, or cartridges into the composition chamber(s) designed to receive the vials/capsules/cartridges.

In some examples, the head module 70 may be detachable from the body module 60. That is, the head module 70 may be removably mechanically coupled to the body module 60. Thus, in some examples, the head module 70 may be removed and replaced entirely. As such, in some examples, the head module 70 may be interchangeable with another head module. Each head module may be specific for a particular composition, for example. In such an example, a radius of the nozzle 30 may be fixed and may be sized according to the particular composition specified to be included for the particular head module 70. In other examples wherein the radius of the nozzle 30 is adjustable as a function of the viscosity of a composition to be atomized, after emptying the composition chamber 42 of a first composition, a second, different composition may be filled into the composition chamber 42 to be atomized, where the radius of the nozzle 30 may be adjusted as a function of the viscosity of the composition added.

Figure 3:
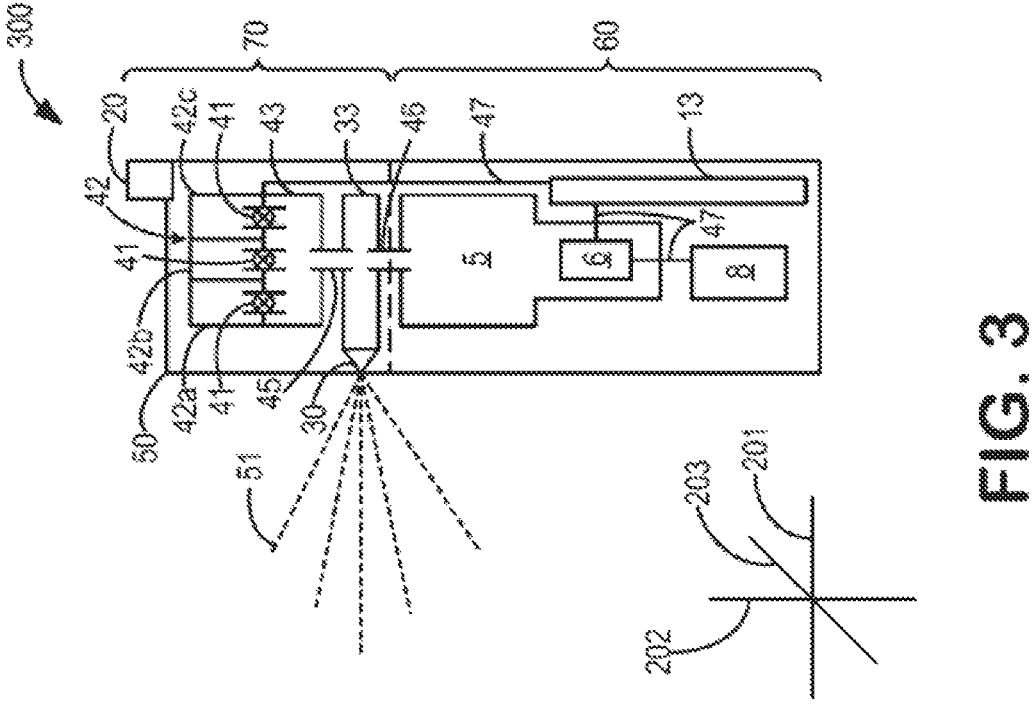
FIG. 3 shows a schematic diagram of the atomizer, where the atomizer includes a plurality of individual composition chambers.

Turning now to FIG. 3, a schematic diagram 300 depicts another example of atomizer 50 including the body module 60 and the head module 70. As illustrated, atomizer 50 as depicted at FIG. 3 may include an intermediary chamber 43 and the composition chamber 42, where the composition chamber 42 may be partitioned into a plurality of individual composition chambers (e.g., a first composition chamber 42a, a second composition chamber 42b, and a third composition chamber 42c) positioned within the head module 70. Each of the plurality of individual composition chambers may pass a composition into the intermediary chamber 43 by way of a valve 41 configured to fluidically couple an individual composition chamber with the intermediary chamber 43. While only one numeral may be used to specify valve 41, it may be understood that each composition chamber includes a valve (e.g., 41), and that the same numeral indicates that the valves are of the same type. In some examples, each composition respectively disposed in the plurality of individual composition chambers may be different from one another. In other examples, each composition respectively disposed in the plurality of individual composition chambers may be the same as one another. In some examples, only one of the plurality of individual composition chambers may be fluidically coupled to intermediary chamber 43 at any one time. In such an example, the process chamber 33 may independently receive, from each of the plurality of individual composition chambers, a respective flow of a single composition by way of the intermediary chamber 43 and the composition passage 45. As an example, in a situation where the first composition chamber (e.g., 42a) has provided its composition to the intermediary chamber 43, the intermediary chamber 43 may not accept another composition from the second composition chamber (e.g., 42b) or the third composition chamber (e.g., 42c) until after both the valve of the first composition chamber 42a has been closed off to the intermediary chamber 43, and the intermediary chamber 43 has been emptied of the first composition (that is, after the intermediary chamber 43 has passed all of the first composition to the process chamber 33 by way of the composition passage 45). However, in other examples it may be possible to fluidically couple more than one composition chamber at a time to the intermediary chamber, in a case where mixing of compositions stored in different composition chambers is desired. For example, depending on the application, it may be desirable to mix different compositions at selected or determined ratios, in order to atomize a composition that has properties that are different from the corresponding individual unmixed compositions. In such examples, more than one composition chamber may be fluidically coupled to the intermediary chamber 43 at any one time.

In some examples, the process of atomization may be controlled by way of the PCB 13. Thus, as discussed herein, the PCB 13 may in some examples be referred to as a controller 13. In some examples, the PCB 13 may be communicatively coupled via the plurality of wired connections 47 to each of the valves 41 and motor 6 of air pump 5. The PCB 13 may further be communicatively coupled to one or more actuators associated with the nozzle 30, for controlling a radius of the nozzle 30. As will be described in greater detail below with reference to FIGS. 8-9C, the PCB 13 may in some examples be electrically communicatively coupled to a remote computing device via a network, wherefrom the PCB 13 may receive customized instructions for controlling one or more of the valves 41, motor 6 of air pump 5, and the radius of the nozzle 30. In such an example, the network may comprise a wired or wireless network. In one such example, the PCB 13 may control the valves 41 in a sequential manner so as to apply a plurality of film layers to the cornea. In some examples, the plurality of film layers may include at least two layers of the biomimicry tear film described above with reference to FIG. 1A.

While FIG. 3 depicts three individual composition chambers, in other examples the plurality of individual composition chambers may include two composition chambers. In still other examples, the plurality of individual composition chambers may include four composition chambers. In still other examples, the plurality of individual composition chambers may include five or more composition chambers.

Similar to that discussed above, each of the plurality of individual composition chambers may be affixed within the head module 70 for receiving compositions directly added thereto from an external container. In other examples, atomizer 50 may be refilled by removing and replacing one or more vials/capsules/cartridges that contain the compositions, where the plurality of individual composition chambers are designed to receive the vials/capsules/cartridges. A composition cavity (not shown but refer to FIG. 6) may be disposed within the head module 70 which may house the plurality of individual composition chambers. In some examples, each of the plurality of the individual composition chambers may be refillable. That is, for example, when at least some of a first composition stored in a first composition chamber (e.g., 42a) has been atomized, more of the first composition may be added to the first composition chamber 42a. In some examples, each of the plurality of individual composition chambers may be refilled by respectively receiving a composition from an external container. In some examples, each of the plurality of individual composition chambers may be refilled by respectively receiving a disposable vial storing a composition, wherein each of the plurality of individual composition chambers may be designed to respectively receive the appropriate disposable vial and the disposable vial may securely fit into the appropriate composition chamber.

In some examples, the plurality of individual composition chambers may be used to store a set of compositions for a biomimicry tear film, an eye wash, and eye drops. In other examples, the plurality of individual composition chambers may be used to store a set of compositions for skin care products, where the skin care products may be one or more of lotions, essences, moistures, day creams, and night creams.

Further exemplary elements, and aspects thereof, shown in FIG. 3 may function substantially similarly to analogous exemplary elements described above with reference to FIG.

2. Also, while not explicitly depicted at FIG. 2, it may be understood that in some examples PCB 13 may be communicatively coupled to nozzle 30 via one of a plurality of wired connections 47, in an atomizer 50 such as that depicted at FIG. 2 that includes a single composition chamber 42 and a removable head module 70. Further, while not explicitly depicted at FIG. 2, it may be understood that in some examples a link rod may couple an atomization actuator 20 to a PCB 13 such that the PCB 13 may be activated upon actuation of the atomization actuator 20. In this way, it may be possible to use compositions of different viscosities in the single composition chamber 42, by adjusting nozzle parameters (e.g., the radius) under control of the controller (e.g., PCB 13), as will be elaborated in further detail below.

Figure 4B:
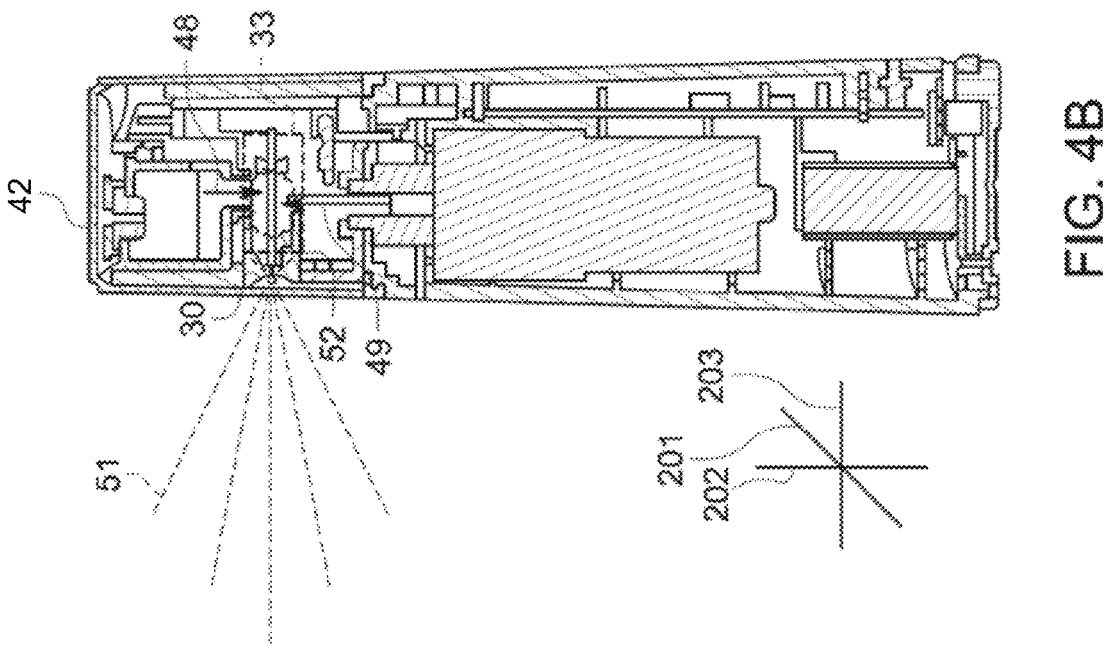
FIG. 4B shows a cross-sectional view of the atomizer performing the example air atomization process of FIG. 4A.
Figure 4A:
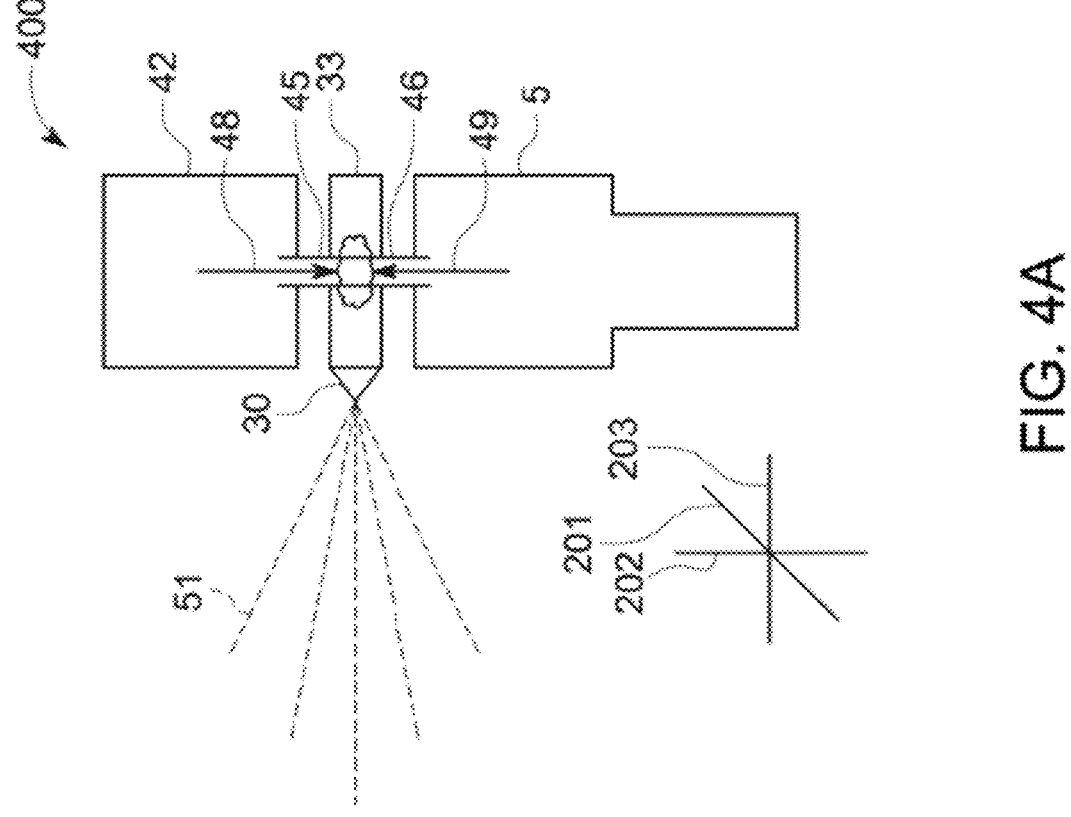
FIG. 4A shows a schematic diagram of an example air atomization process.

Referring now to FIG. 4A, a schematic diagram 400 depicts an example air atomization process, or air spray atomization process, performed by an atomizer, such as the atomizer 50 described above with reference to FIGS. 2-3. The composition chamber 42 may contain a composition 48 (e.g., liquid, fluid, etc.). The composition 48 may be passed into the process chamber 33 via the composition passage 45 in a low-speed stream. Further, the air pump 5 may contain air 49. Upon actuation of the motor (e.g., 6) of the air pump 5, the air 49 may pass into the process chamber 33 via the air passage 46 in a high-speed stream from a direction opposite that of the composition 48 entering the process chamber 33. As such, friction resulting from the interaction of the composition 48 and the air 49 may accelerate and disrupt the low-speed stream of the composition 48, resulting in an atomized mixture 52.

The atomized mixture 52 may be passed from the process chamber 33 through the nozzle 30 to leave the atomizer (e.g., 50) as the spray mist 51. The spray mist 51 may be applied to a cornea of an eye to deliver a film layer, such as a component film layer of the biomimicry tear film. In some examples, further modules/process may alter properties of the spray mist 51 (e.g., pressure, droplet size, pattern, etc.) by varying control of a pressure of the air 49.

Referring now to FIG. 4B, a cross-sectional view 450 depicts the atomizer 50 performing the example air atomization process of FIG. 4A. In some examples, the atomizer 50 depicted by the cross-section view 450 may constitute the specific embodiment described below with reference to FIGS. 12A-16. As shown, the composition 48 may interact with the air 49 in the process chamber 33 to form the atomized mixture 52. The atomized mixture 52 may then pass through the nozzle 30 to form the spray mist 51. The spray mist 51 may be applied to the cornea of the eye to deliver a film layer, such as a component film layer of the biomimicry tear film.

Figure 5B:
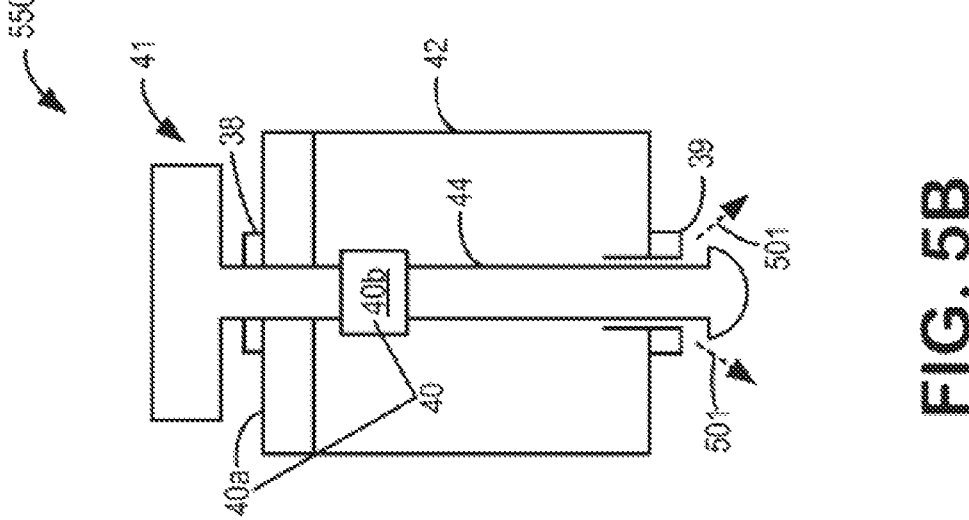
FIG. 5B shows an example schematic diagram of the composition chamber of FIG. 5A with the associated valve in an extended or open position.
Figure 5A:
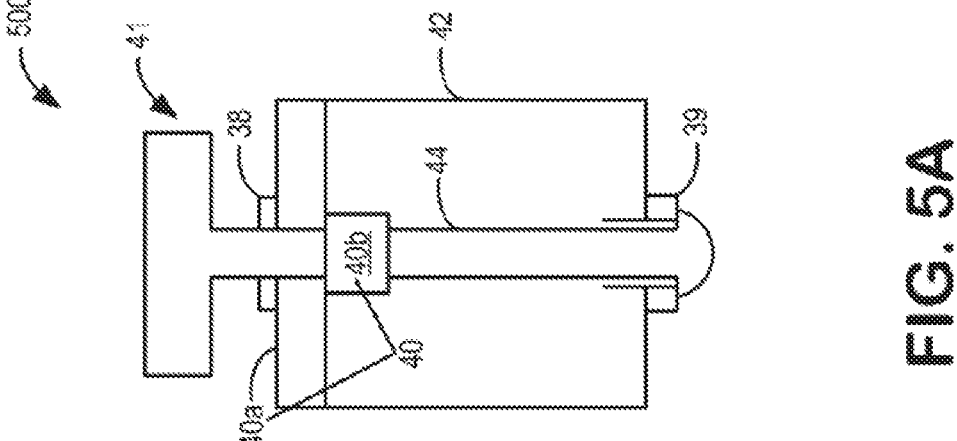
FIG. 5A shows an example schematic diagram of a composition chamber with an associated valve in a retracted or closed position.
Figure 7A:
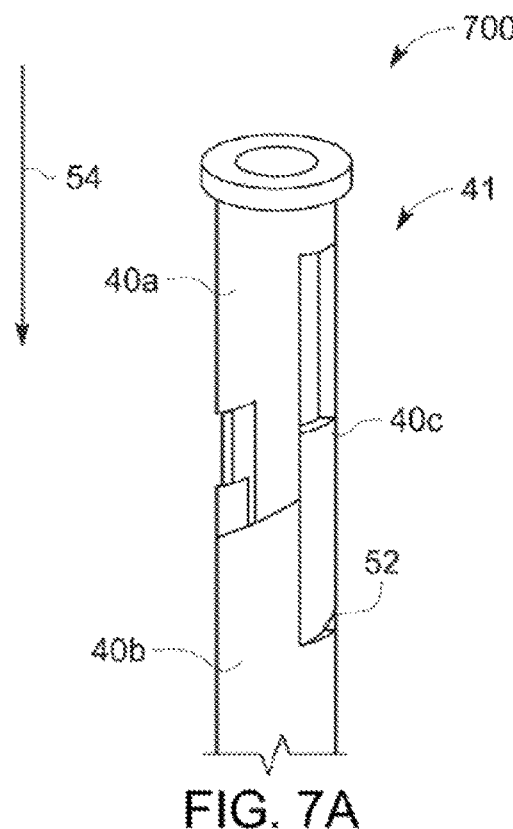
FIG. 7A shows an example illustration of a mechanism for how the valve of FIGS. 5A-5B can adopt the retracted position.
Figure 7B:
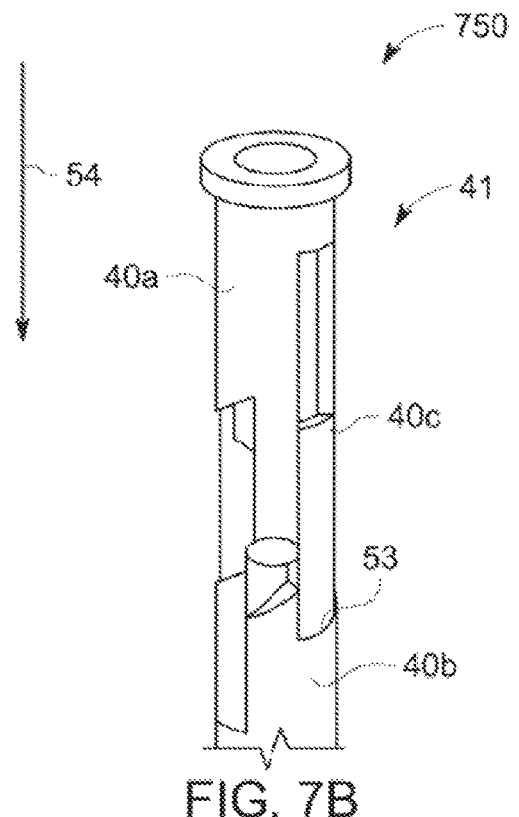
FIG. 7B shows an example illustration of a mechanism for how the valve of FIGS. 5A-5B can adopt the extended position.

Referring now to FIG. 5A, a schematic diagram 500 depicts one example embodiment of composition chamber 42 with valve 41 in a closed position. In the example embodiment depicted by the schematic diagram 500, valve 41 operates via a plunger-type mechanism, but in other examples the valve 41 may operate differently, for example the valve 41 may comprise a solenoid-actuatable valve in some examples without departing from the scope of this disclosure. Accordingly, for the example embodiment depicted by the schematic diagram 500, a plunger 44 comprises a component of valve 41. As discussed, the composition chamber 42 may be included in the head module (e.g., 70) of the atomizer (e.g., 50) described above with reference to FIG. 2, and a composition may be disposed within the composition chamber 42. In the example embodiment depicted by the schematic diagram 500, valve 41 may include mechanical lock 40, which may comprise a top portion 40a and a bottom portion 40b. Rotational and vertical movement of the top portion 40a of mechanical lock 40 with respect to the bottom portion 40b of mechanical lock 40 may allow for movement of valve 41 from a retracted position (depicted at FIG. 5A) to an extended position (refer to FIG. 5B), similar to a mechanism utilized via retractable ballpoint pens for extending and retracting an ink cartridge. FIG. 5A depicts a simplified view for illustrative purposes. Turning to FIG. 7A, a more detailed example illustration 700 of such a mechanism is shown. FIG. 7A depicts a portion of valve 41, including top portion 40a, bottom portion 40b, and stop member 40c (which is not depicted at FIG. 5A). When configured in the retracted position as shown at FIG. 7A, stop member 40c engages a first notch 52 of the bottom portion, causing the top portion 40a to seat against the bottom portion 40b, similar to that illustratively depicted at FIG. 5A. Alternatively, turning to FIG. 7B, example illustration 750 depicts stop member 40c engaged with a second notch 53 of the bottom portion 40b. When stop member 40c engages second notch 53, a physical separation between the top portion 40a and the bottom portion 40b occurs, resulting in the extended position as illustrated at FIG. 7B, similar to that illustratively depicted at FIG. 5B. As the mechanism for extending and retracting an ink cartridge of a ballpoint pen is well understood by those of ordinary skill in the art, detailed explanation is not included herein for brevity. However, it may be understood that application of a first force applied in a direction 54 may cause valve 41 to adopt and latch the retracted position, and application of a second force applied in the direction 54 may cause valve 41 to adopt and latch the extended position, in a similar mechanistic fashion as that utilized by ballpoint pens to retract and extend an ink cartridge. It may be understood that the first force and the second force may be substantially similar (e.g., within 5% of each other). Such a force may be applied by way of a finger depressing an atomization actuator (not shown) that mechanically couples to valve 41, for example. In other examples, such actuation may be electronically controllable.

Accordingly, returning to FIG. 5A, when configured in the retracted position, a composition housed in composition chamber 42 may be prevented from flowing into the process chamber (e.g., 33, not shown at FIG. 5A). In the example embodiment depicted by the schematic diagram 500, valve 41 includes a top ring spacer 38 and a bottom ring spacer 39, to reduce or avoid leaking of the composition from composition chamber 42.

Turning now to FIG. 5B, a schematic diagram 550 depicts the same composition chamber 42 and valve 41 as shown in FIG. 5A, with valve 41 in the extended position as discussed. When in the extended position, it may be understood that the composition chamber 42 may be fluidically coupled to the process chamber (e.g., 33, not shown at FIG. 5B), to allow the composition to flow into the process chamber as depicted by arrows 501.

Figure 6:
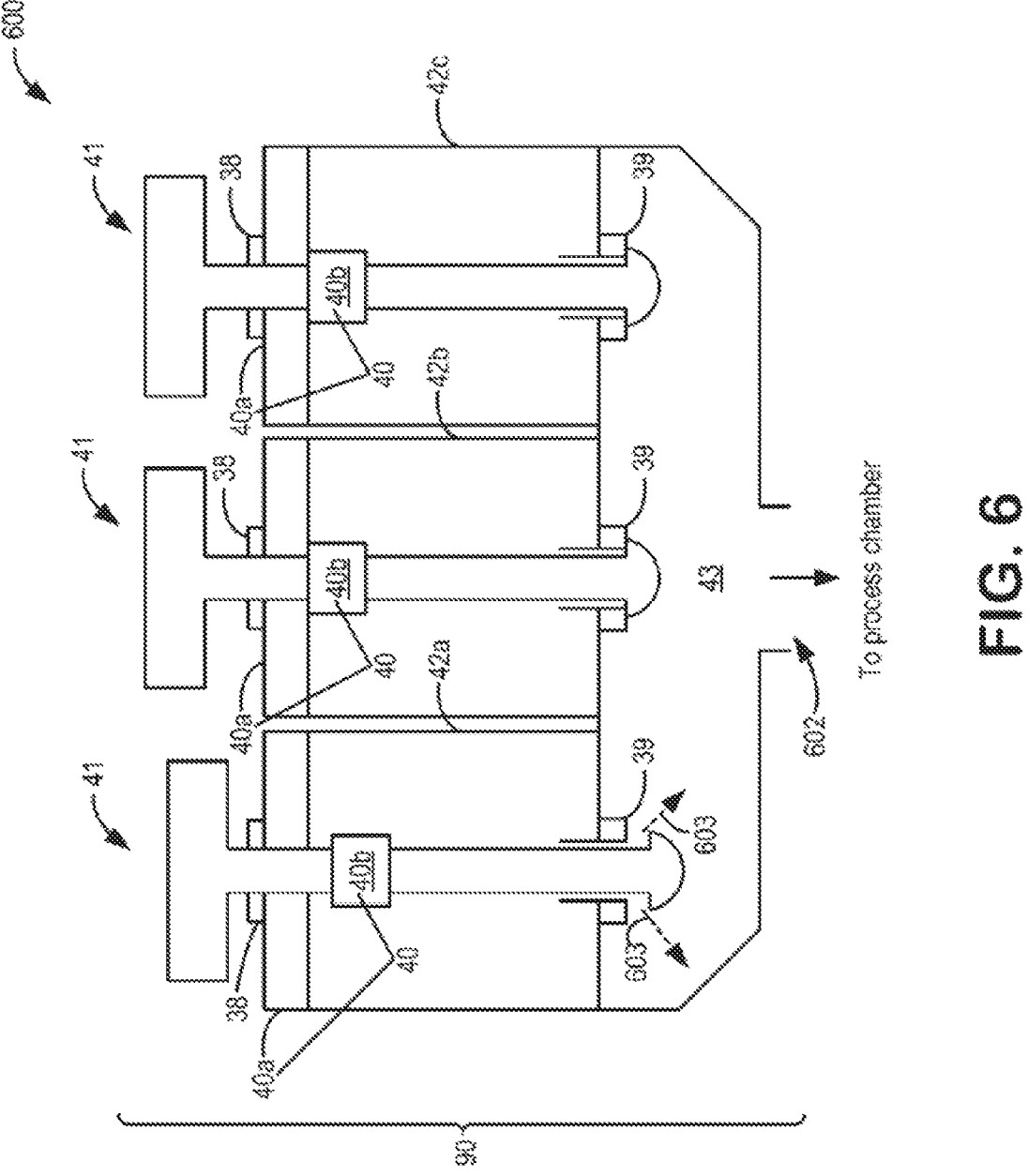
FIG. 6 shows a schematic diagram of a composition cavity including three individual composition chambers coupled to an intermediary chamber.

Turning now to FIG. 6, a schematic diagram 600 depicts an illustrative example of a composition cavity 90 included in the head module (e.g., 70), that includes three composition chambers. Specifically, composition cavity 90 includes first composition chamber 42a, second composition chamber 42b, and third composition chamber 42c. Each of the first composition chamber 42a, the second composition chamber 42b, and the third composition chamber 42c may be fluidically coupled to the intermediary chamber 43, the intermediary chamber 43 in turn being fluidically coupled to the process chamber (e.g., 33), by way of the composition passage (e.g., 45, not shown at FIG. 6). Each of the first composition chamber 42a, the second composition chamber 42b, and the third composition chamber 42c may be substantially similar to the composition chamber 42 described above with respect to FIGS. 5A and 5B. Thus, it may be understood that composition cavity 90 may include the plurality of individual composition chambers (e.g., the first composition chamber 42a, the second composition chamber 42b, and the third composition chamber 42c), the intermediary chamber 43, and the valves 41 described above with reference to FIG. 3 and FIGS. 5A-5B. The intermediary chamber 43 may have a bottom opening 602 which may allow a composition disposed therein to flow through the composition passage (e.g., 45) to the process chamber (e.g., 33).

Each of the composition chambers 42a, 42b, 42c may include valve 41 respectively disposed therein. Each of the valves 41 depicted at FIG. 6 comprise valves that operate in the fashion as discussed at FIGS. 5A-5B and FIGS. 7A-7B, and thus detailed explanation of how the valves operate is not provided. In other examples not shown at FIG. 6, valves 41 included in each composition chamber of a multi-chambered composition cavity may operate differently (e.g., solenoid actuated valves, etc.) without departing from the scope of this disclosure.

FIG. 6 depicts first composition chamber 42a fluidically coupled to intermediary chamber 43, such that the composition housed in first composition chamber 42 flows into intermediary chamber 43 as depicted by arrows 603. As depicted, second composition chamber 42b and third composition chamber 42c are not fluidically coupled to the intermediary chamber (the respective valves are in the retracted position), thus preventing compositions housed in each of the second and third composition chambers 42b, 42c from flowing into the intermediary chamber 43.

In some examples, each composition respectively disposed in the composition chambers (e.g., 42a, 42b, 42c) may be different from one another. When each composition is different, it may be understood that each composition may comprise a different viscosity. In other examples, two or more compositions respectively disposed in the composition chambers 42a, 42b, 42c may be the same as one another. In some examples, only one of the composition chambers 42a, 42b, 42c may be fluidically coupled to the intermediary chamber 43 at any one time. As such, each of the composition chambers 42a, 42b, 42c may independently provide a respective flow of a composition to intermediary chamber 43. In other examples, more than one of the composition chambers 42a, 42b, 42c may be fluidically coupled to intermediary chamber 43 at a same time, to enable mixing of the compositions housed in the respective composition chambers 42a, 42b, 42c.

As mentioned above, in some examples the atomization actuator (e.g., 20) may be manually depressed or otherwise manually actuated (e.g., slid, rotated, etc.), which may in turn activate the motor (e.g., 6) for providing the air flow to the process chamber (e.g., 33), and in some examples may further fluidically couple a composition chamber (e.g., 42a, 42b, 42c) to the process chamber (by way of the intermediary chamber 43 in a case where a plurality of composition chambers 42a, 42b, 42c are included in the head module, e.g., 70, of the atomizer, e.g., 50). However, in other examples a control strategy may be implemented by a controller (e.g., 13) for controlling the motor and/or for actuating a composition chamber to be fluidically coupled to the process chamber. Simply put, the atomization actuator may be understood to comprise in one example an on/off actuator (e.g., button, slidable member, rotatable protrusion) for actuating on and off the motor. It may be understood that such an atomization actuator may in some examples be accessible to a finger of a user or medical professional, such that the atomization actuator may be mechanically pressed, depressed, etc., (in other words, actuated), to actuate on and off the motor. For example, in a case where there is a single composition chamber (refer to FIG. 2) in the head module, there may be a single atomization actuator for actuating on and off the motor. In a case where there is a plurality of composition chambers (refer to FIG. 3), there may in some examples be a plurality of atomization actuators (e.g., three different depressible buttons or other actuators), which may each actuate on the motor and which may also, when actuated, control an open/closed status of a valve (e.g., 41) corresponding to a particular composition chamber. In this way, a user may, for example, depress a first atomization actuator which may control a first valve associated with a first composition chamber to an open position and also actuate the motor, depress a second atomization actuator which may control a second valve associated with the second composition chamber and also actuate the motor, and depress a third atomization actuator which may control a third valve associated with the third composition chamber and also actuate the motor. It may be understood that in such an example, depressing the first atomization actuator again may deactivate the motor and control the first valve to a closed position, and so on. In examples wherein the valve 41 includes a plunger (e.g., 44) extending through a particular composition chamber, when a corresponding atomization actuator is actuated, the plunger may be displaced to fluidically couple the composition chamber to the process chamber. However, as elaborated in further detail below, control of such valves and actuation of the motor may be in other examples under control of the controller.

Figures 8, 9A, 9B, 9C:
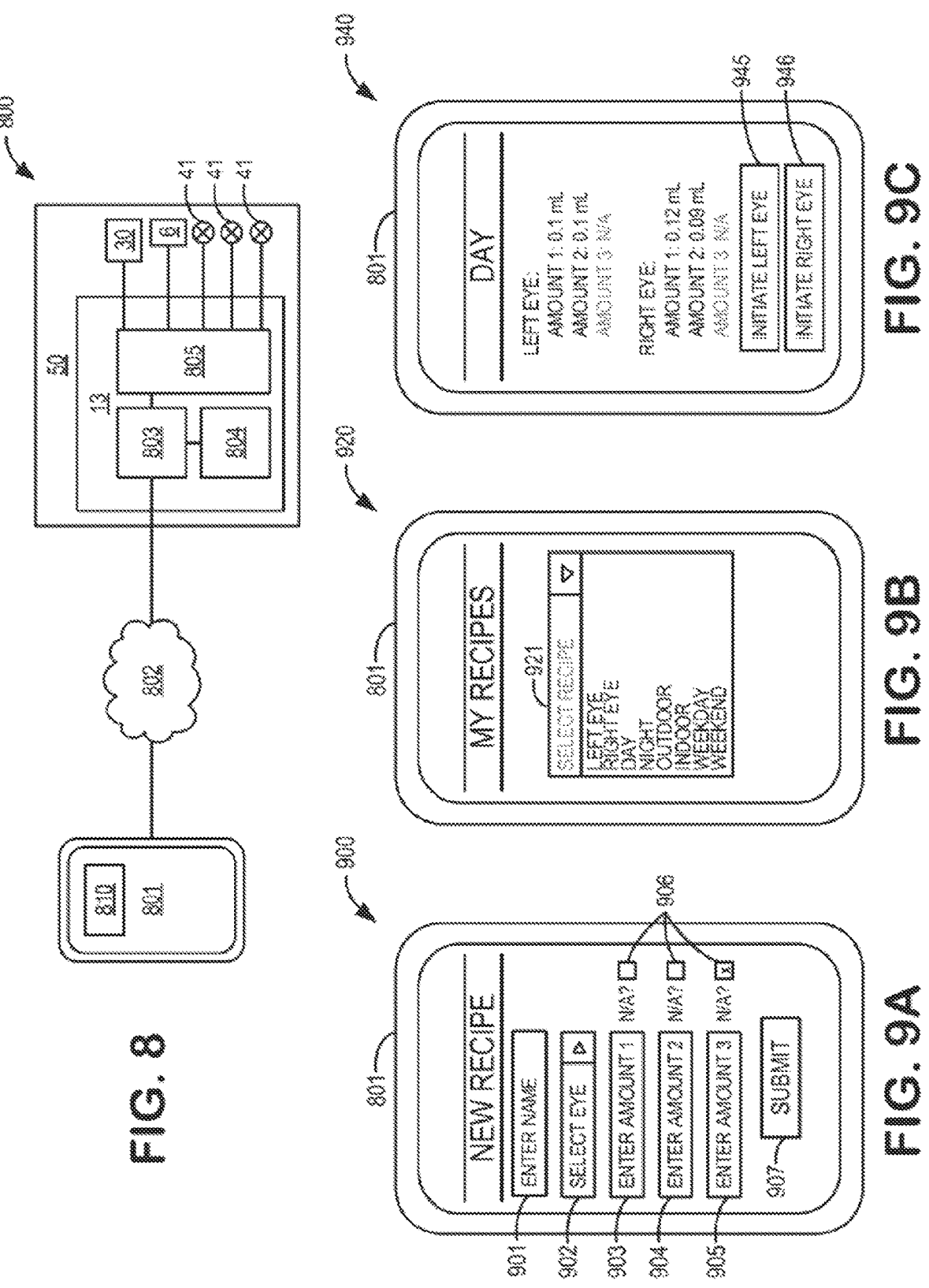
FIG. 8 shows a schematic computing environment for implementing one or more control methods of the present disclosure.
FIG. 9A shows a first example screen of a customization program for the atomizer of the present disclosure.
FIG. 9B shows a second example screen of the customization program for the atomizer of the present disclosure.
FIG. 9C shows a third example screen of the customization program for the atomizer of the present disclosure.

Referring now to FIG. 8, a schematic computing environment 800 for implementing control methods for atomizing and spraying a composition or compositions depicts the atomizer 50 selectively communicably coupled to a remote computing device 801 by way of a network 802. Network 802 may comprise a wired network in one example, or a wireless network in other examples. In examples where network 802 is wireless, it may be understood that a wireless transceiver (e.g., Bluetooth transceiver) (not shown) may be included in the body module (e.g., 60) of atomizer 50. The remote computing device 801 may be a laptop, smartphone, tablet, desktop computer, remote control, etc. As described in more detail below with reference to FIGS. 9A-9C, the remote computing device 801 may include a customization application or program 810 (e.g., software application), for which a user of the application may input a variety of parameters for controlling the atomizing and spraying of a composition or compositions.

In such an example atomizer 50 may include the PCB (e.g., 13) functioning as a controller of the atomizer 50. The PCB 13 in this example embodiment may include a processing unit 803, a memory 804 (e.g., read-only memory, random access memory), and input/output (I/O) ports 805. The processing unit 803 may be communicatively coupled to the memory 804, which may store non-transitory, computer readable data representing instructions executable by the processing unit 803 for performing one or more control methods, where such control methods may be based on parameters input into customization application 810, as will be discussed in further detail below with regard to FIGS. 9A-9C. Examples of such control methods are depicted below with regard to FIGS. 10-11, for example. The processing unit 803 may be communicatively coupled to the I/O ports 805, which may communicatively couple the processing unit 803 to an actuator (not shown) of the motor (e.g., 6) of the air pump (e.g., 5). In some examples, the I/O ports 805 may communicatively couple the processing unit 803 to one or more valve actuators (not shown) of the composition chamber valve(s) (e.g., 41). In this way, the processing unit 803 may, based on instructions stored in the memory 804, adjust position (e.g., closed or open, which in some examples may correspond to retracted and extended positions, respectively) of one or more valves (e.g., 41) associated with the composition chamber(s) (e.g., 42), and may additionally or alternatively control a speed of the motor (e.g., 6). Still further, the processing unit 803 may in some examples communicably couple to one or more nozzle actuators (not shown) associated with the nozzle (e.g., 30), which may enable a radius of an orifice of the nozzle to be adjusted. Such control strategy may be particularly useful in cases where the head module (e.g., 70) includes a plurality of composition chambers (e.g., 42a, 42b, 42c), each of which store a composition of a different viscosity, for example. Along similar lines, operational status of the valve(s) may be controlled at least in part based on viscosity of the composition(s) stored in the composition chamber(s), and the speed of the motor of the air pump may too be controlled at least in part based on viscosity of the composition(s) stored in the composition chamber(s).

Turning now to FIGS. 9A-9C, example screens of the customization application (e.g., 810) for the atomizer (e.g., 50) are depicted. Briefly, it is herein recognized that different users of the atomizer may have different requirements in terms of respective quantities of one or more of the mucin layer, the aqueous layer, and the lipid layer applied to a cornea of the user, that may be sufficient for providing relief from DES. In some examples, each eye of such a user may further require different respective quantities of one or more of the mucin layer, the aqueous layer, and/or the lipid layer applied to the cornea of the user, for providing relief from DES. Accordingly, via use of the customization application (e.g., 810), a user may personally define parameters for atomizing and spraying the composition or compositions in line with what has been found by the user to provide relief from DES symptoms, as discussed in further detail below with regard to FIGS. 9A-9C. Such parameters may be communicated to the controller (e.g., 13) of the atomizer via wired or wireless communication between the customization application and the atomizer, as discussed above.

Briefly, the customization application (e.g., 810) may include an ability to input parameters including but not limited to 1) a desired amount of each composition to apply to a particular eye or a desired location as a function of time; 2) a desired sequence of application of each composition (e.g., adhesive layer followed by aqueous layer followed by oil layer, etc.) applied to a particular eye; 3) a desired droplet size of the spray mist (e.g., 51) applied to a particular eye of the user, which may be defined by one or more of a radius of the nozzle (e.g., 30) and associated orifice of the atomizer (e.g., 50), and motor speed (e.g., the speed of the motor, e.g., 6, of the air pump, e.g., 5); 4) a desired duration of application of each composition to be applied to a particular eye of the user; etc.

Referring now to FIG. 9A, a first example screen 900 of the customization application (e.g., 810) for the atomizer (e.g., 50) is depicted on the remote computing device 801. It may be understood that first example screen 900 is a simplified example, for illustrative purposes. As depicted, first example screen 900 may be operable to receive information relating to a new customization recipe. Discussed herein, a customization recipe may include information pertaining to an amount of each composition to be applied to a particular eye, a sequence for applying compositions to a particular eye under circumstances where the customization recipe includes more than one composition, a viscosity and/or components of each composition, etc. Based on such information, the processing unit (e.g., 803) may control the process of atomization and spraying of the composition or compositions to the eye of the user. For example, based on input from the customization application, a motor speed may be controlled accordingly, a radius of the nozzle (e.g., 30) and associated orifice may be adjusted accordingly, one or more valve(s) (e.g., 41) associated with the composition chamber(s) (e.g., 42) may be controlled accordingly, etc. For simplicity, only the amount(s) of desired compositions are depicted at FIG. 9A. For example, a user, such as a patient or a medical professional, may enter a recipe name at 901 and select an eye at 902. The user may enter an amount of a first composition, for example the composition corresponding to the aqueous layer of tear film, at 903, may enter an amount of a second composition, for example the composition corresponding to the oil layer, at 904, and may enter an amount of a third composition, for example the composition corresponding to the adhesive layer, at 905. While this example includes options for customizing amounts of three compositions, in other examples more than three compositions may be selected from, without departing from the scope of this disclosure. In some examples, the user may indicate whether or not a given composition is applicable or not (N/A) to the customization recipe at 906. The user may submit the inputted information to the customization application at 907.

Referring now to FIG. 9B, a second example screen 920 of the customization application (e.g., 810) for the atomizer (e.g., 50) is depicted on the remote computing device 801. It may be understood that second example screen 920 is a simplified example, for illustrative purposes. As depicted, second example screen 920 may store one or more saved customization recipes, such that the user may select from the saved customization recipes. It may be understood that a user of the atomizer may have different recipes corresponding to different days of the week, different times of a particular day, different recipes for whether the user will spend time outdoors or indoors, different recipes for each eye, etc. The user, such as the patient or the medical professional, may select one of the one or more stored customization recipes by way of a menu, such as a drop-down menu, at 921. It may be understood that the stored customization recipes as depicted at FIG. 9B may be generated based on information provided to first example screen 900 as described above with reference to FIG. 9A.

Referring now to FIG. 9C, a third example screen 940 of the customization application (e.g., 810) for the atomizer (e.g., 50) is depicted on the remote computing device 801. It may be understood that third example screen 940 is a simplified example, for illustrative purposes. Third example screen 940 may be operable to display information relating to the stored customization recipes depicted at FIG. 9B. For example, at second example screen 920 the user may select a particular saved customization recipe, and at third example screen 940 the information pertaining to the saved customization recipe may be displayed, which may for example include the specified amount(s) of each composition to apply to a particular eye, the sequence of application of composition(s) to a particular eye, etc. Third example screen 940 may further include a selection option for initiating the atomization and spraying process for the particular selected recipe. For example, a first selection option 945 may initiate the process of atomizing and spraying the particular recipe for the left eye, and a second selection option 946 may initiate the process of atomizing and spraying the particular recipe for the right eye. The controller (e.g., 13) of the atomizer may receive the instructions from the customization application and may atomize and spray the composition(s) in accordance with the received instructions. In some examples where the process of atomization is initiated through the customization application as discussed with regard to FIG. 9C, there may be a time delay between the user selecting to initiate the atomization process and the atomizer actually atomizing and spraying the desired/selected composition. The time delay may enable the controller to adjust the radius of the nozzle (e.g., 30), as an example, although in other examples the radius of the nozzle may be adjusted under a different control command from the customization application and controller. The time delay may also allow for the user to properly position the atomizer with respect to the eye of the user, so that the user is prepared for the incoming spray mist (e.g., 51) at a time of delivery. In one example, the time delay may comprise 5 seconds. In another example, the time delay may comprise 10 seconds. In another example, the time delay may comprise 3 seconds. In still other examples, the time delay may be a parameter that the user may select or input into the customization application. In some examples where a sequence of compositions is desired, there may be another time delay between application of different compositions, which may each be of similar duration as that discussed above. Similar to that discussed above, such durations may be in some examples selectable or customized by the user, such as the patient or the medical professional.

Figure 10:
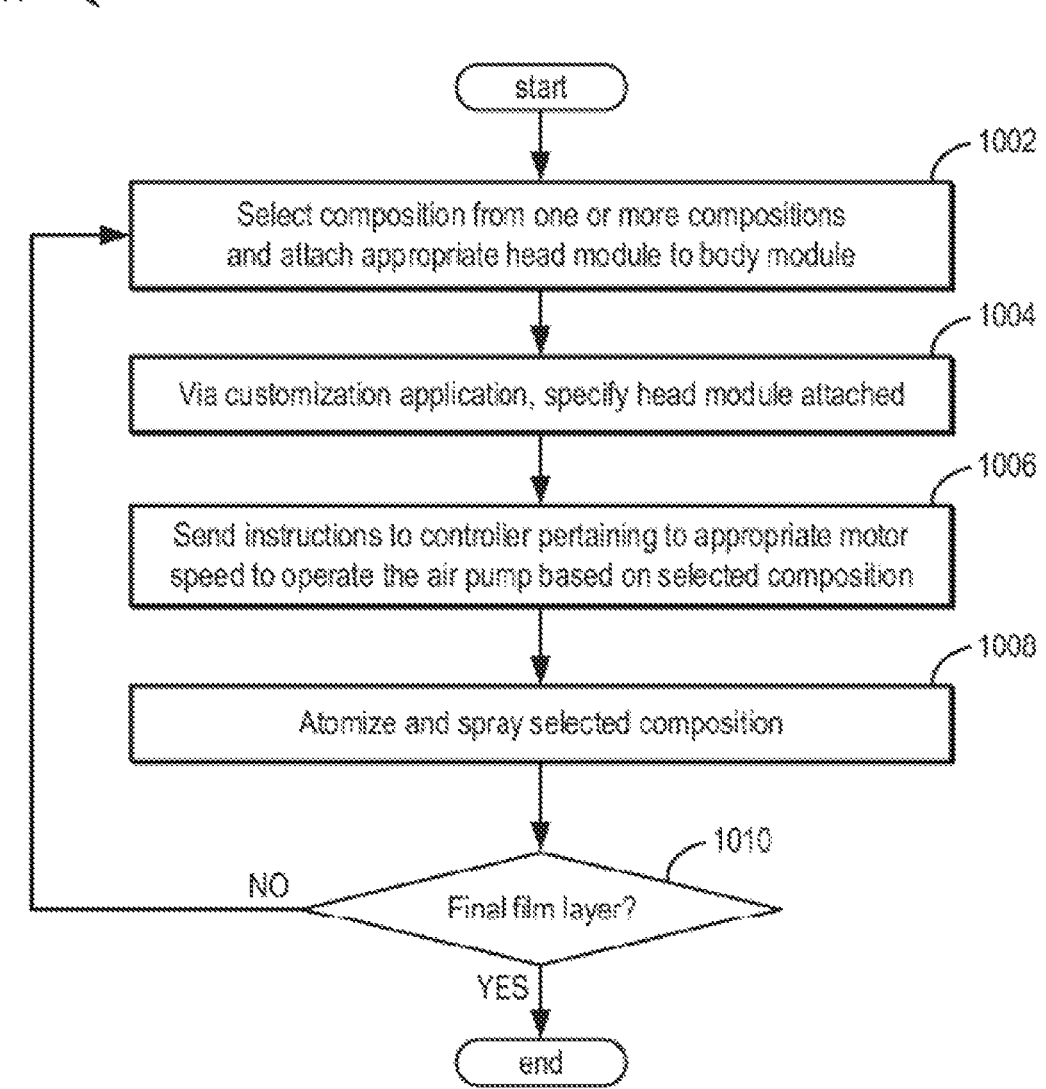
FIG. 10 shows a method for delivering one or more film layers to an eye via use of the atomizer of the present disclosure.

Referring now to FIG. 10, a method 1000 for delivering the one or more film layers that mimic layers of tear film to an eye via the atomizer (e.g., 50), is depicted. The method 1000 will be described with reference to the atomizer systems described herein, though it may be understood that similar methods may be applied to other systems without departing from the scope of this disclosure. It may be understood that the method of FIG. 10 relates to use of an atomizer where the head module (e.g., 70) is detachable from the body module (e.g., 60), where the head module includes a single composition chamber (e.g., 42), similar to the atomizer illustrated at FIG. 2. For the example method of FIG. 10, certain steps may be conducted via a user of the atomizer while other steps may include instructions received from the customization application (e.g., 810). Steps that are controlled via such instructions are specifically mentioned in the below description with regard to FIG. 10.

At 1002, a user may select a composition to apply to an eye or eyes (e.g., cornea(s)). Selecting the composition may include selecting from a first composition that mimics the aqueous layer of tear film, a second composition that mimics the oil layer of tear film, and a third composition that mimics the adhesive layer of tear film, for example. In some examples, selecting the composition at 1002 may include selecting which composition to apply first based on a desire to sequentially layer the eye or eyes with different compositions.

Upon selecting the composition, the user may then attach an appropriate head module (e.g., 70) to the body module (e.g., 60). For example, there may be a set of removable head modules (e.g., three or more different head modules), where each head module from the set is specified for receiving a particular composition. As a representative example, a first head module may be configured specifically for the first composition (e.g., aqueous composition), a second head module may be configured specifically for the second composition (e.g., lipid composition), and a third head module may be configured specifically for the third composition (e.g., adhesive composition). More specifically, a radius of the nozzle (e.g., 30) for each head module may be specific for the particular composition specified to be included in the given head module. In other words, because compositions corresponding to each of the tear film layers may differ, and therefore viscosities of the compositions may differ, the radius of the nozzle for each head module may be specific for the corresponding composition specified to be included in the particular head module. While not explicitly illustrated at step 1002, it may be understood that if the head module corresponding to the selected composition is not already filled with the selected composition, then the user may fill the composition chamber (e.g., 42) included in the head module with the selected composition. Filling the composition chamber may include adding the composition directly to the composition chamber from another external container or, in other examples, may include the user inserting a pre-filled vial, capsule, or cartridge that stores the selected composition into the appropriate composition chamber included in the head module.

Proceeding to 1004, with the head module (e.g., 70) attached, the user may input into the customization application (e.g., 810) which head module is attached for use. The customization application may then determine the appropriate corresponding motor speed (that is, the speed of the motor, e.g., 6, of the air pump, e.g., 5) for atomizing and spraying the selected composition, the motor speed determination a function of the viscosity of the composition specific to the particular head module. While in this example methodology the motor speed may be determined based on the input from the user pertaining to head module into the customization application, in other examples the body module may include a sensing means (not shown) which can interpret which head module is attached, and correspondingly control motor speed accordingly.

Continuing to 1006, method 1000 may include the customization application (e.g., 810) communicating instructions to the controller (e.g., 13) as to the motor speed for atomizing and spraying the selected composition. As discussed above, such communication of instructions may be via wired or wireless communication. With such instructions received at the controller, method 1000 may proceed to 1008.

At 1008, method 1000 may include atomizing and spraying the selected composition. Specifically, the user of the atomizer (e.g., 50) may initiate the process of atomizing and spraying the selected composition by actuating (e.g., depressing, sliding, rotating, etc.) an atomization actuator (e.g., button, knob, slidable actuator, etc.) that in turn activates the motor (e.g., 6) of the air pump (e.g., 5) at the instructed motor speed. In some examples, actuation of the atomization actuator (e.g., 20) may additionally fluidically couple the composition chamber (e.g., 42) with the process chamber (e.g., 33). The composition and air flow from the air pump may then be routed to the process chamber before exiting the nozzle (e.g., 30) as the spray mist (e.g., 51) for layering the cornea with the selected composition. In such an example where the atomization actuator is actuated via the user, the user may again actuate the atomization actuator to stop the process of atomizing and spraying the composition. Thus, in such an example, an amount of the composition applied to the eye of the user, and duration that the composition is applied to the eye of the user, is regulated via the user. In other examples, the controller (e.g., 13) may automatically stop the process of atomization after a predetermined duration, or based on instructions received from the customization application (e.g., 810).

After atomizing and spraying the selected composition, method 1000 may proceed to 1010. At 1010, method 1000 may include the user determining if the layer just applied corresponding to the selected composition is the last or final layer that is desired by the user to be applied to the eye of the user. If not, then method 1000 may return to 1002, where another composition may be selected by the user. In such a case, the user may then detach the head module (e.g., 70) currently attached to the body module (e.g., 60), may select which composition to apply to the eye next, and may then attach the appropriate head module corresponding to the next selected composition to the body module. Such a process may be repeated any number of times, depending on the user.

While the above-described methodology is directed to an application for treating DES, it may be understood that other applications are within the scope of this disclosure. For example, rather than the compositions corresponding to compositions that mimic tear film layers, in other examples the compositions may correspond to lotions, day/night creams, essences, etc. A similar methodology as that depicted at FIG. 10 may be used in such examples without departing from the scope of this disclosure. However, it may be understood that different head modules (e.g., 70) may be used for other applications, where the different head modules for the other applications are specific to each composition included therein for atomization.

Figure 11:
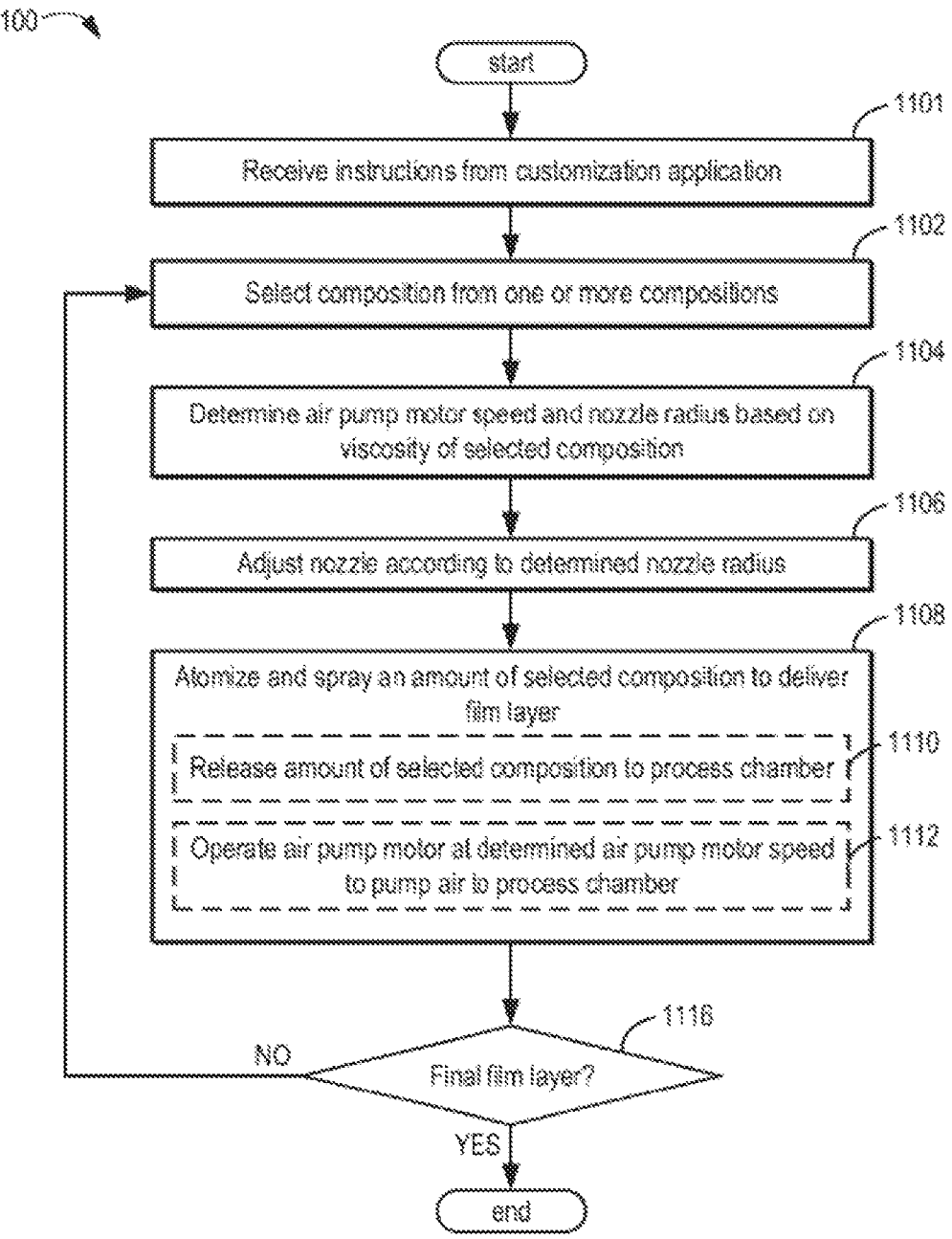
FIG. 11 shows another method for delivering one or more film layers to the eye via use of the atomizer of the present disclosure, wherein the head module of the atomizer includes multiple composition chambers.

Turning now to FIG. 11, another method 1100 for delivering one or more film layers to the eye via the atomizer (e.g., 50), is depicted, wherein the head module (e.g., 70) of the atomizer includes a plurality of composition chambers (e.g., 42a, 42b, 42c). Accordingly, method 1100 may relate to an atomizer such as that depicted illustratively at FIG. 3, for example. Method 1100 will be described with reference to the systems described herein, though it may be understood that similar methods may be applied to other systems without departing from the scope of this disclosure. Further, certain steps of the method 1100 depicted at FIG. 11 may be carried out via the controller (e.g., 13), and may be stored at the controller (e.g., a controller implemented by one or more micro-computer processors) as executable instructions in non-transitory memory. Instructions for carrying out method 1100 may be executed by the controller based on instructions stored on a memory (e.g., 804) and in conjunction with instructions received from a remote computing device (e.g., 801) running the customization application (e.g., 810) for use with the atomizer. The controller may employ one or more actuators to adjust operations of one or more elements described herein. More specifically, the controller may control open and closed positions of valve(s) (e.g., 41) for each composition chamber, may control a radius of the nozzle (e.g., 30), and may control a speed of the motor (e.g., 6) of the air pump (e.g., 5), for example.

At 1101, method 1100 may include the controller (e.g., 13) receiving instructions from the customization application (e.g., 810), the instructions related to a user-defined, or medical-professional defined, set of parameters for forming one or more tear film layers on an eye of a user of the atomizer. As discussed above, such instructions may be received via wired or wireless communication between a remote computing device (e.g., 801) that runs the customization application, and the controller of the atomizer (e.g., 50).

With the instructions received at 1101, method 1100 may proceed to 1102. At 1102, method 1100 may include selecting a composition to atomize and spray from a plurality of compositions respectively stored in the plurality of composition chambers (e.g., 42a, 42b, 42c). The selecting at 1102 may be via the controller (e.g., 13) based on the instructions received from the customization application (e.g., 810).

Continuing to 1104, method 1100 may include the controller determining a motor speed appropriate for atomizing and spraying the selected composition. At 1104, method 1100 may further include the controller determining a nozzle radius appropriate for atomizing and spraying the selected composition. It may be understood that both the motor speed and the radius of the nozzle (e.g., 30) may be determined as a function of a viscosity of the selected composition. That is, both the motor speed and the radius of the nozzle may be adjustable as a function of which composition is selected.

Proceeding to 1106, method 1100 may include adjusting the radius of the nozzle (e.g., 30) based on the selected composition. More specifically, the controller (e.g., 13) may send a signal to an actuator or actuators associated with the nozzle, thereby actuating the nozzle to be adjusted in terms of a radius appropriate for the selected composition.

Following adjustments to the nozzle (e.g., 30), method 1100 may proceed to 1108. At 1108, method 1100 may include atomizing and spraying a particular amount of the selected composition to deliver the desired film layer to the eye of the user of the atomizer (e.g., 50). The particular amount may originate as a parameter input into the customization application (e.g., 810), for example. However, in other examples, the particular amount may comprise a default amount, without departing from the scope of this disclosure. The particular amount (or default amount in other examples) may be a function of a duration that the composition chamber storing the selected composition is fluidically coupled to the process chamber (e.g., 33), for example. For example, the composition chamber may be fluidically coupled to the process chamber to release a desired amount of the selected composition into the process chamber (by way of the intermediary chamber, e.g., 43), at which point the composition chamber storing the selected composition may be sealed off from the process chamber. In other words, the controller may exert operational control over a position of a valve (e.g., 41) associated with the composition chamber storing the selected composition, to control an amount of the selected composition to be atomized and sprayed. Accordingly, at 1110, method 1100 includes the controller (e.g., 13) commanding open the valve associated with the composition chamber storing the selected composition to release the desired amount of the selected composition into the process chamber (by way of the intermediary chamber), after which the valve may be commanded closed via the controller. However, in other examples, the valve may be maintained open during the process of atomizing and spraying the selected composition, without departing from the scope of this disclosure. In such an example where the valve is kept open, the amount atomized and sprayed may be based on a time frame which the motor (e.g., 6) of the air pump (e.g., 5) is activated, and where the valve may be closed upon the motor of the air pump being deactivated.

At 1112, method 1100 may include the controller (e.g., 13) commanding the motor (e.g., 6) of the air pump (e.g., 5) to operate in order to supply the air flow from the air pump to the process chamber (e.g., 33) via the air passage (e.g., 46). The speed at which the motor of the air pump is operated may be retrieved from step 1104 of method 1100. As mentioned briefly above, the time frame for which the motor is activated may be a function of the desired amount of the selected composition to be atomized and sprayed onto the eye of the user. In this way, the selected composition may be atomized and sprayed as the spray mist (e.g., 51) onto the eye of the user to apply a layer, or film layer, that mimics a tear film layer. While not explicitly illustrated, the user may initiate the atomization and spraying process via one of pressing the atomization actuator (e.g., 20) associated with the head module (e.g., 70), or instructing the atomization and spraying process to commence via an option included in the customization application (e.g., 810), as discussed above.

With the selected composition atomized and sprayed onto the eye of the user, method 1100 may continue to 1116. At 1116, it may be determined as to whether the layer applied to the eye of the user is the final layer desired by the user to be applied. If so, method 1100 may end. For example, the atomizer may be turned off or deactivated to reduce power consumption. Alternatively, if at 1116 it is determined via the controller (e.g., 13) that another composition is desired to be sprayed onto the eye of the user to form another layer, then method 1100 may return to step 1102 where the method may repeat in order to apply the new layer. Upon the final layer being indicated as applied, method 1100 may end as discussed above.

Figures 12A, 12B, 12C:
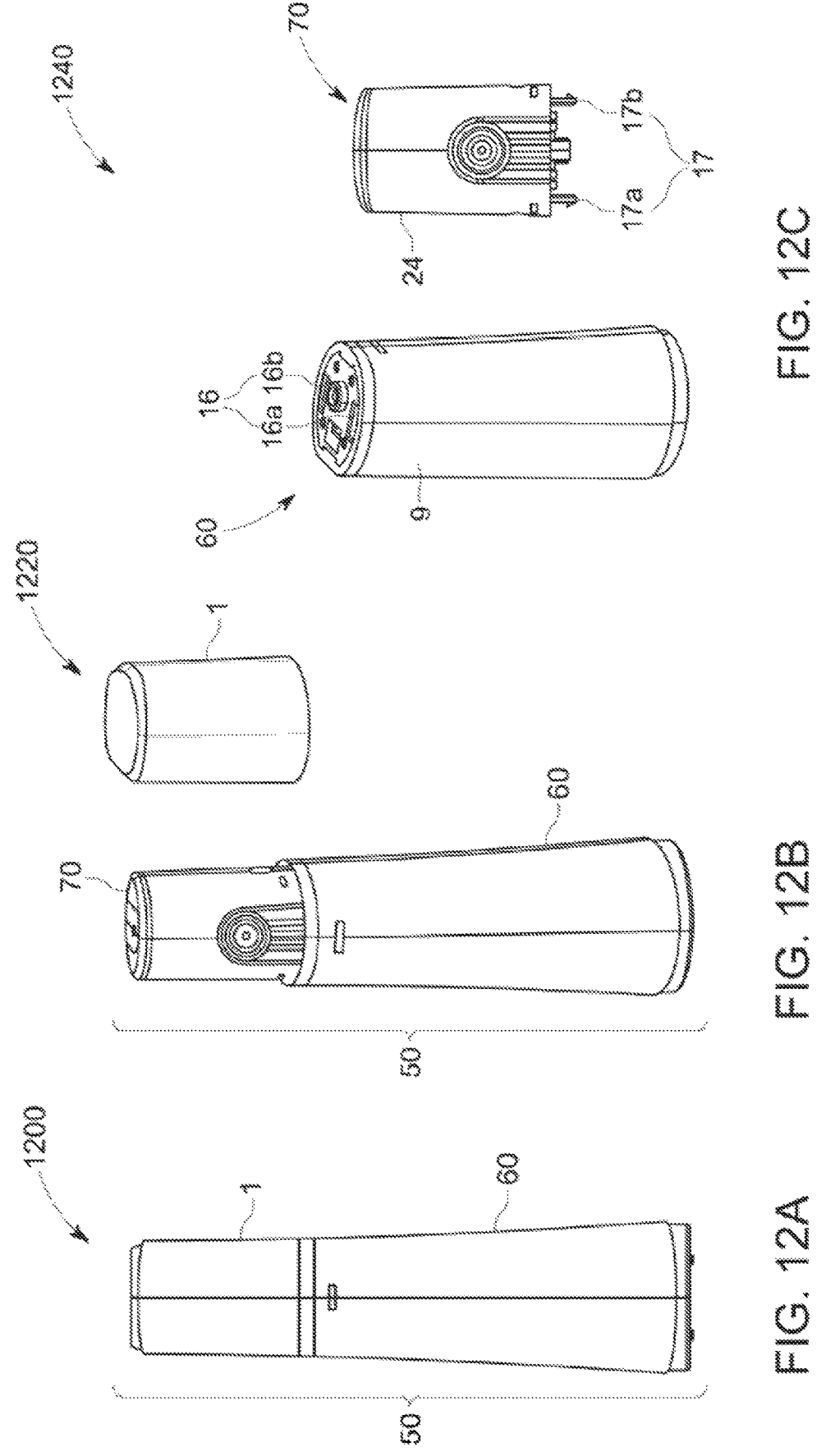
FIG. 12A shows a first view of the atomizer of the present disclosure.
FIG. 12B shows a second view of the atomizer of the present disclosure, where a cap of the atomizer has been detached from the atomizer.
FIG. 12C shows a view of a head module and a body module of the atomizer of the present disclosure, where the head module has been detached from the body module.

Referring now to FIG. 12A, a first view 1200 depicts the atomizer 50. As shown, the atomizer 50 may include the body module 60 and the cap 1, where the cap 1 may be removably coupled to the body module 60. The cap 1 may prevent accidental actuation of the atomizer 50 when being carried or held. Further, the cap 1 may prevent damage to the head module (e.g., 70) (disposed underneath the cap 1 in the first view 1200).

Referring now to FIG. 12B, a second view 1220 depicts the atomizer 50. As shown, the cap 1 may be detached and separated, exposing the head module 70. In some examples, the head module 70 may have a composition disposed therein. The body module 60 may be removably and mechanically coupled to the head module 70. As such, the head module 70 may be interchangeable with another head module 70 when, for example, the head module 70 is emptied of the composition, or another composition is desired.

Referring now to FIG. 12C, a view 1240 depicts the head module 70 and the body module 60 of the atomizer (e.g., 50). As shown, the head module 70 may be detached and separated from the body module 60. Mechanical fasteners 17 may be included in the head module 70. Specifically, a first mechanical fastener 17a and a second mechanical fastener 17b may be coupled to a head casing 24 of the head module 70. Further, mechanical fastener receiving elements 16 may be included in the body module 60 to receive the mechanical fasteners 17. Specifically, a first mechanical fastener receiving element 16a and a second mechanical fastener receiving element 16b may each be positioned on a top face of a body casing 9 of the body module 60. Insertion of the first mechanical fastener 17a into the first mechanical fastener receiving element 16a and insertion of the second mechanical fastener 17b into the second mechanical fastener receiving element 16b may thereby mechanically couple the head module 70 to the body module 60.

Figure 13:
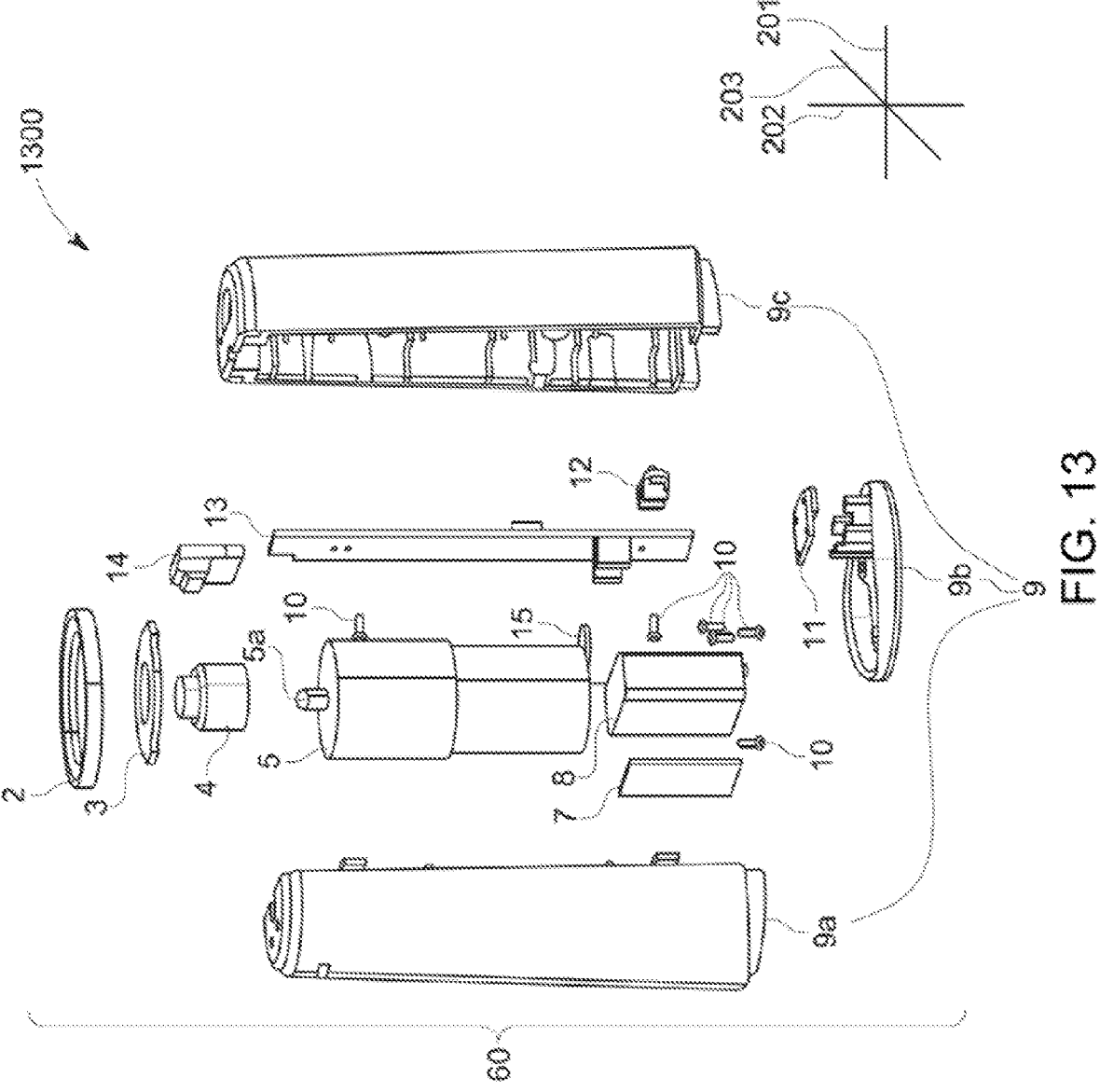
FIG. 13 shows an exploded view of the body module of the atomizer of the present disclosure.

Referring now to FIG. 13, an exploded view 1300 depicts the body module 60 of the atomizer (e.g., 50). Components of the body module 60 depicted in the exploded view 1300 may be included within the body casing 9. The body casing 9 may include three portions, specifically, a front body casing 9a, a bottom body casing 9b, and a back body casing 9c. As such, the front body casing 9a, the bottom body casing 9b, and the back body casing 9c may correspond to a front face, a bottom face, and a back face of the body module 60, respectively.

The body module 60 may include the air pump 5 with the motor (e.g., 6), where an air outlet 5a at least partially disposed within the air pump 5 may be fluidically coupled to the process chamber (e.g., 33) of the head module (e.g., 70) via the air passage (e.g., 46) of the process chamber 33. Further, the body module 60 may include a pump-to-head connector 4. The pump-to-head connector 4 may extend along the vertical axis 202 upwards from the body module 60 to the process chamber 33 of the head module 70. As shown, the pump-to-head connector 4 may be at least partially disposed around a protruding portion of the air outlet 5a. The pump-to-head connecter 4 may function to further secure the head module 70 to the body module 60.

The body module 60 may further include the battery 8. The battery 8 may be a rechargeable battery. The battery 8 may be electrically coupled to the motor (e.g., 6) of the air pump 5. The battery 8 may be positioned below the air pump 5 with respect to the vertical axis 202.

The body module 60 may further include the PCB 13 and a first spacer 14. A link rod (described below with reference to FIG. 14) of the head module (e.g., 70) may mechanically engage with the PCB 13 via a first spacer 14. Specifically, the first spacer 14 may be at least partially disposed on a front face of the PCB 13, and between the PCB 13 and the link rod of the head module 70. The PCB 13 may be electrically coupled to the motor (e.g., 6) of the air pump 5. When the link rod of the head module 70 mechanically engages with the PCB 13, the PCB 13 may thereby activate the motor 6 of the air pump 5 to produce an air flow to the process chamber (e.g., 33) of the head module 70. The PCB 13 may operate the motor 6 of the air pump 5 in a speed range from 100 RPM to 110,000 RPM. A speed at which the motor 6 of the air pump 5 operates may be controlled by the PCB 13 such that the speed corresponds to a viscosity of a composition stored in the head module 70 to be atomized.

The body module 60 may further include a power light source 3 which may be electrically coupled to the PCB 13. The power light source 3 may be annular in shape, encircling the pump-to-head connector 4. The power light source 3 may be positioned on the front body casing 9a, such that at least a portion of the power light source 3 may be exposed to an external surface of the body module 60. The power light source 3 may illuminate in response to activation of the motor (e.g., 6) of the air pump 5.

The body module 60 may further include a charging circuit board 11 and a charging light source 12. The charging circuit board 11 may be disposed below the PCB 13 with respect to the vertical axis 202, above the bottom body casing 9b with respect to the vertical axis 202, and behind the battery 8 with respect to the front-to-back axis 201. The battery 8 may be electrically coupled to the charging circuit board 11. Further, the charging light source 12 may be electrically coupled to the charging circuit board 11 and may be disposed between the PCB 13 and the back body casing 9b. When lit, the charging light source 12 may indicate a charging status of the battery 8.

The body module 60 may further include a second spacer 7, a third spacer 15, a plurality of fasteners 10, and a top ring 2. The second spacer 7 may be disposed along the front-toback axis 201 between the battery 8 and the front body casing 9a. The third spacer 15 may be disposed on a bottom face of the air pump 5. The plurality of fasteners 10 may hold various components of the body module 60 to one another. The top ring 2 may be positioned on top of the body casing 9 with respect to the vertical axis 202.

Figure 14:
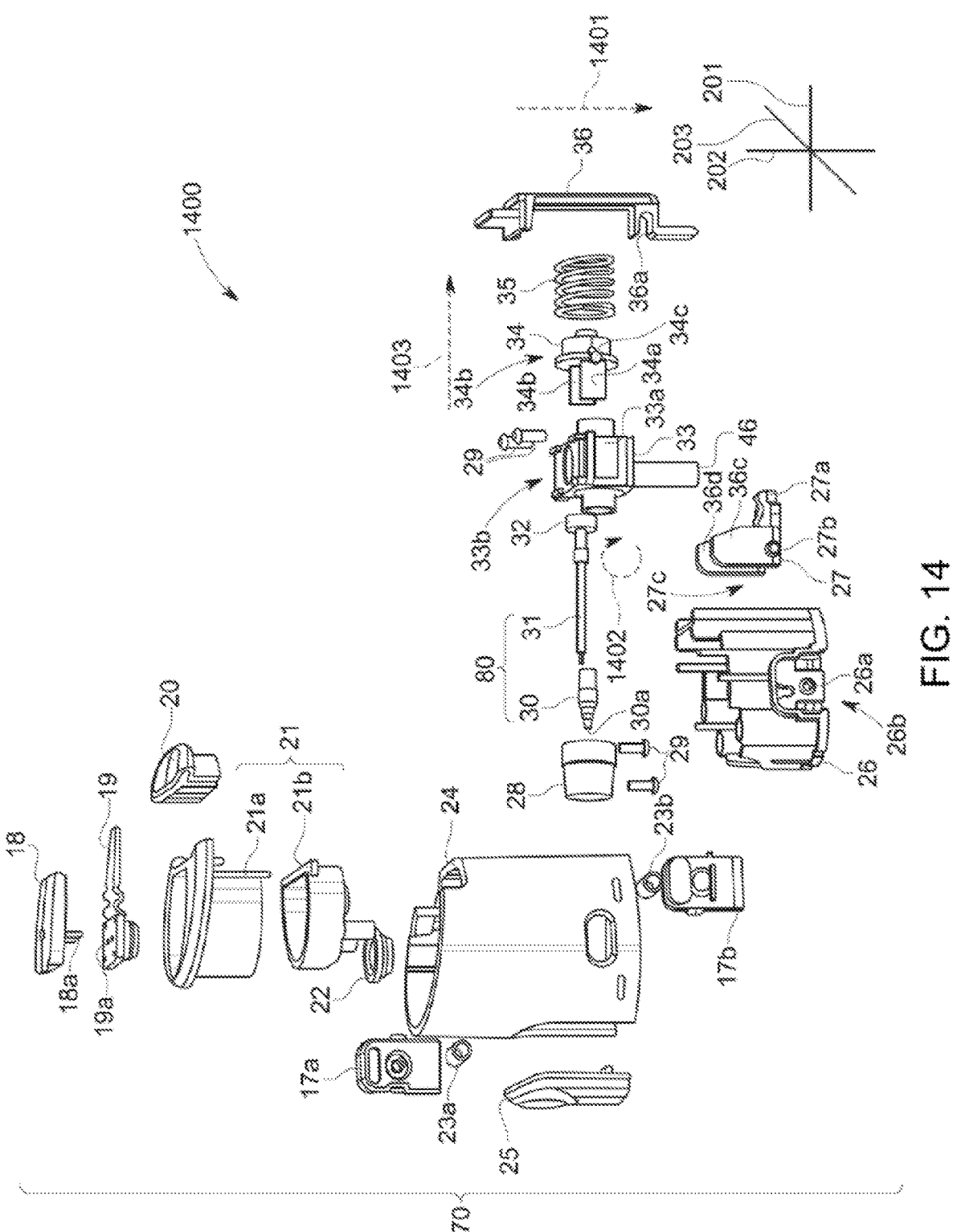
FIG. 14 shows an exploded view of the head module of the atomizer of the present disclosure.

Referring now to FIG. 14, an exploded view 1400 depicts the head module 70 of the atomizer (e.g., 50). A plurality of components of the head module 70 depicted in the exploded view 1300 may be included within the head casing 24.

The head module 70 may include a composition chamber 21, a first lid 19 for the composition chamber 21, a second lid 18 for the composition chamber 21, and a ring spacer 22. The composition chamber 21 may include an upper compartment 21a and a lower compartment 21b, where the upper compartment 21a may be disposed on top of the lower compartment 21b with respect to the vertical axis 202. Further, the upper compartment 21a may sealingly engage with the lower compartment 21b such that a composition stored within the composition chamber 21 may not leak between the upper compartment 21a and the lower compartment 21b. The first lid 19 may sealingly engage with the upper compartment 21a such that the composition stored with the composition chamber 21 may not leak between the upper compartment 21a and the first lid 19. Further, the first lid 19 may be composed of silicone. The second lid 18 may include one or more male connectors 18a extending from a bottom face of the second lid 18. The one or more male connectors 18a may sealingly engage with one or more female connectors 19a associated with a top face of the first lid 19. Further, the ring spacer 22 may be disposed below the lower compartment 21b and above the process chamber 33 with respect to the vertical axis 202. The ring spacer 22 may prevent leakage of the composition when the composition passes from the composition chamber 21 to the process chamber 33 for atomization.

The head module 70 may further include the process chamber 33, a needle valve assembly 80, a front frame 25, a front cover 28, a sealing element 32, a needle valve cover 34, and a first spring 35. The process chamber 33 may be positioned below the composition chamber 21 with respect to the vertical axis 202. The process chamber 33 may include the air passage 46, which may fluidically couple to the air pump (e.g., 5) of the body module (e.g., 60) via the air outlet (e.g., 5a) of the air pump 5. The process chamber 33 may further include a first groove 33a and a second groove 33b. It will be understood that the second groove 33b, though not visible in the exploded view 1400, may be of a mirrored configuration of the first groove 33a, and may be disposed on a second outer face of the process chamber 33 opposite a first outer face of the process chamber 33 including the first groove 33a along the horizontal axis 203.

The needle valve assembly 80 may be included within the process chamber 33. The needle valve assembly 80 may extend along the front-to-back axis 201. Further, the needle valve assembly 80 may include a micro nozzle 30 and a needle 31, where the needle 31 may be at least partially disposed within the micro nozzle 30. The micro nozzle 30 may have an orifice 30a positioned at the front frame 25.

The front cover 28 may be disposed between the micro nozzle 30 and the front frame 25 with respect to the front-to-back axis 201. The sealing element 32 may be disposed between the needle 31 and the needle valve cover 34 with respect to the front-to-back axis 201. The needle valve cover 34 may include a first prong 34a and a second prong 34b that extend along the front-to-back axis 201. The first prong 34a and the second prong 34b of the needle valve cover 34 may slidingly engage along the front-to-back axis 201 with the first groove 33a and the second groove 33b of the process chamber 33, respectively. The needle valve cover 34 may include a first prong 34c and a second prong 34d. It will be understood that the second prong 34d, though not visible in the exploded view 1400, may be of a mirrored configuration of the first prong 34c, and may be disposed on a second outer face of the needle valve cover 34 opposite a first outer face of the needle valve cover 34 including the first prong 34c along the horizontal axis 203. The needle valve cover 34 may further be mechanically coupled to each of the needle 31 and the first spring 35 such that the needle valve cover 34 may be disposed between the needle 31 and the first spring 35 with respect to the front-to-back axis 201. The first spring 35 may bias the needle 31 to a fully seated position within the nozzle 30.

The head module 70 may further include an atomization actuator 20, a link rod 36, a hinged connector 27, and a body frame 26. The atomization actuator 20 may be depressible. The link rod 36 may extend along the vertical axis 202 from the head module 70 to the body module 60. Further, the link rod 36 may be selectively mechanically coupled to the atomization actuator 20 such that the atomization actuator 20 and the link rod 36 together may depress in a direction 1401 parallel to the vertical axis 202. The link rod 36 may include a link rod groove 36a disposed on a lower portion of the link rod 36 with respect to the vertical axis 202.

The hinged connector 27 may include a first pin 27a and a second pin 27b. It will be understood that the second pin 27b, though not visible in the exploded view 1400, may be of a mirrored configuration of the first pin 27a, and may be disposed on a second outer face of the hinged connector 27 opposite a first outer face of the hinged connector 27 including the first pin 27a along the horizontal axis 203. The hinged connector 27 may further include a first fin 27c and a second fin 27d that extend along the vertical axis 202. The hinged connector 27 may further include a connecting element 27e positioned along the front-to-back axis 201. The connecting element 27e may fit into the link rod groove 36a such that downward movement of the link rod 36 in the direction 1401 rotationally mechanically engages the hinged connector 27 via the connecting element 27e. Upon mechanical engagement, the hinged connector 27 may rotate in a direction 1402 around a rotational axis, where the rotational axis is parallel with the horizontal axis 203. The hinged connector 27 may then mechanically engage with the needle valve cover 34 to compress the first spring 35 in a direction 1403 parallel with the front-to-back axis 201. Specifically, the first fin 27c and the second fin 27d of the hinged connector 27 may contact the first prong 34c and the second prong 34d of the needle valve cover 34. When the first spring 35 is compressed, the needle 31 may be unseated from the fully seated position in the nozzle 30, moving in the direction 1403. When the composition stored in the composition chamber 21 has been passed to the process chamber 23, the needle 31 has been unseated from the fully seated position in the nozzle 30, and the motor (e.g., 6) of the air pump (e.g., 5) has been activated, the composition may interact with the air from the air pump 5 and exit the orifice 30a as the spray mist (e.g., 51).

The process chamber 33 may be surrounded by the body frame 26. The body frame 26 may include a first female acceptor element 26a and a second female acceptor element 26b. It will be understood that the second female acceptor element 26b, though not visible in the exploded view 1400, may be of a mirrored configuration of the first female acceptor element 26a, and may be disposed on a second outer face of the body frame 26 opposite a first outer face of the body frame 26 including the first female acceptor element 26a along the horizontal axis 203. The first female acceptor element 26a and the second female acceptor element 26b of the body frame 26 may receive the first pin 27a and the second pin 27b of the hinged connector 27, respectively.

The head module 70 may further include the first mechanical fastener 17a, the second mechanical fastener 17b, a second spring 23a, and a third spring 23b. The first mechanical fastener 17a may be biased to a first locked position via the second spring 23a. Further, the second mechanical fastener 17b may be biased to a second locked position via the third spring 23b. When the head module 70 is attached to the body module (e.g., 60), compression of the second spring 23a may disengage and release the first mechanical fastener 17a from the first mechanical fastener receiving element 16a of the body module 60. Further, when the head module 70 is attached to the body module 60, compression of the third spring 23b may disengage and release the second mechanical fastener 17b from the second mechanical fastener receiving element 16b of the body module 60.

The head module 70 may further include a plurality of fasteners 29. The plurality of fasteners 29 may hold various components of the body module 60 to one another.

Figure 15:
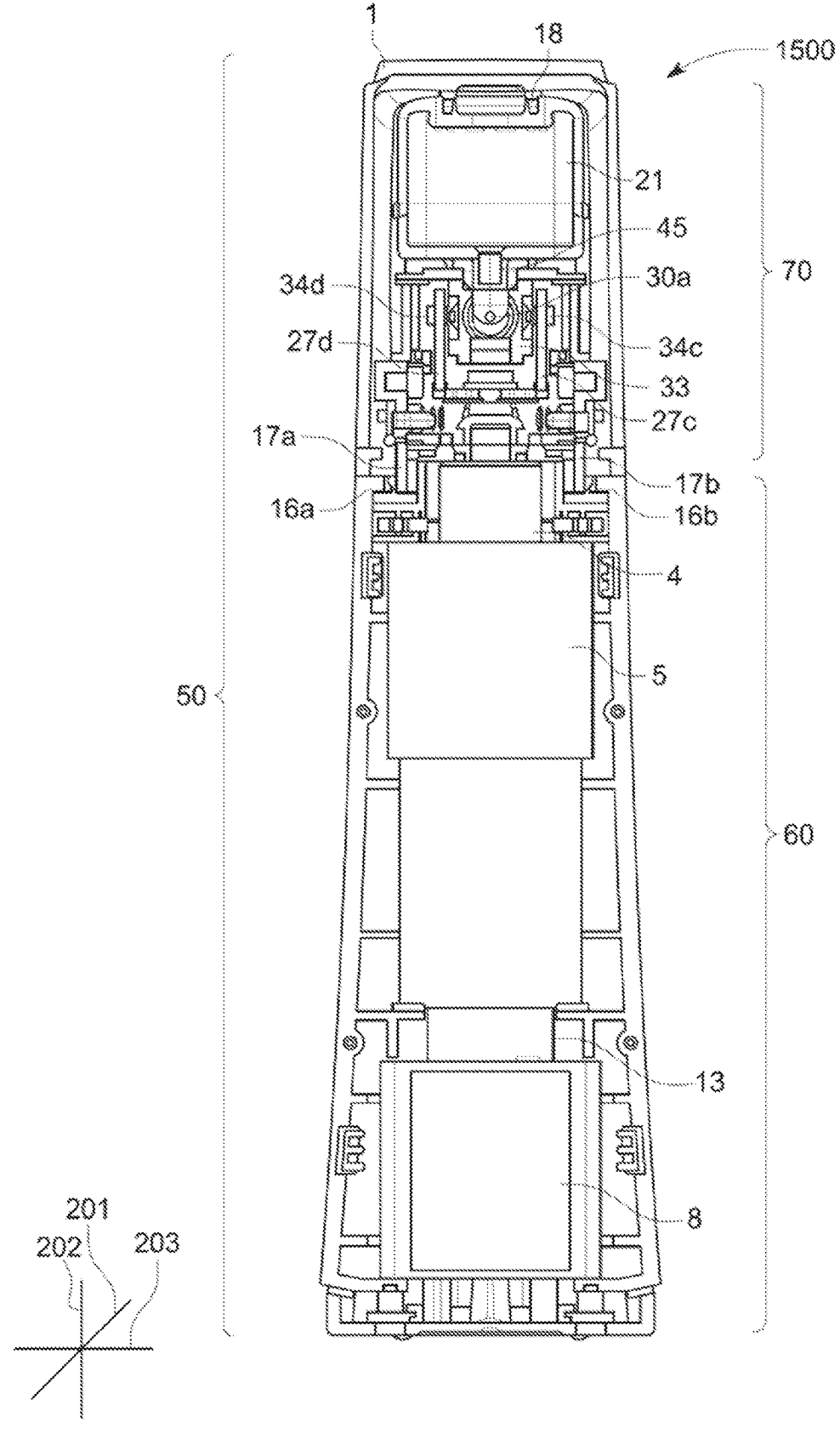
FIG. 15 shows a first cross-sectional view of the atomizer of the present disclosure.

Referring now to FIG. 15, a first cross-sectional view 1500 depicts the atomizer 50. As shown, the body module 60 may be positioned below the head module 70 with respect to the vertical axis 202. Further, and as shown, the cap 1 may cover the head module 70. The first mechanical fastener 17a and the second mechanical fastener 17b are shown as being mechanically coupled to the first mechanical fastener receiving element 16a and the second mechanical fastener receiving element 16b, respectively.

The battery 8 may be positioned below the air pump 5 with respect to the vertical axis 202. Further, the air pump 5 may be positioned below the pump-to-head connector 4 with respect to the vertical axis 202. In the first cross-sectional view 1500, the PCB 13 is shown as partially obscured by the battery 8, the air pump 5, and the pump-to-head connector 4.

The second lid 18 may be positioned above the composition chamber 21 with respect to the vertical axis 202. In the first cross-sectional view 1500, the second lid 18 is shown as being engaged with the composition chamber 21. Further, the composition chamber 21 may be positioned above the process chamber 33 with respect to the vertical axis 202. The composition chamber 21 may include the composition passage 45 which may couple to the process chamber 33. As such, the process chamber 33 may be fluidically coupled to the composition chamber 21 via the composition passage 45. A composition stored in the composition chamber 21 may pass into the process chamber 33 and may exit the atomizer 50 via the orifice 30a during an atomization. Further, and as shown, the first fin 27c and the second fin 27d of the hinged connector 27 may contact the first prong 34c and the second prong 34d of the needle valve cover 34.

Figure 16:
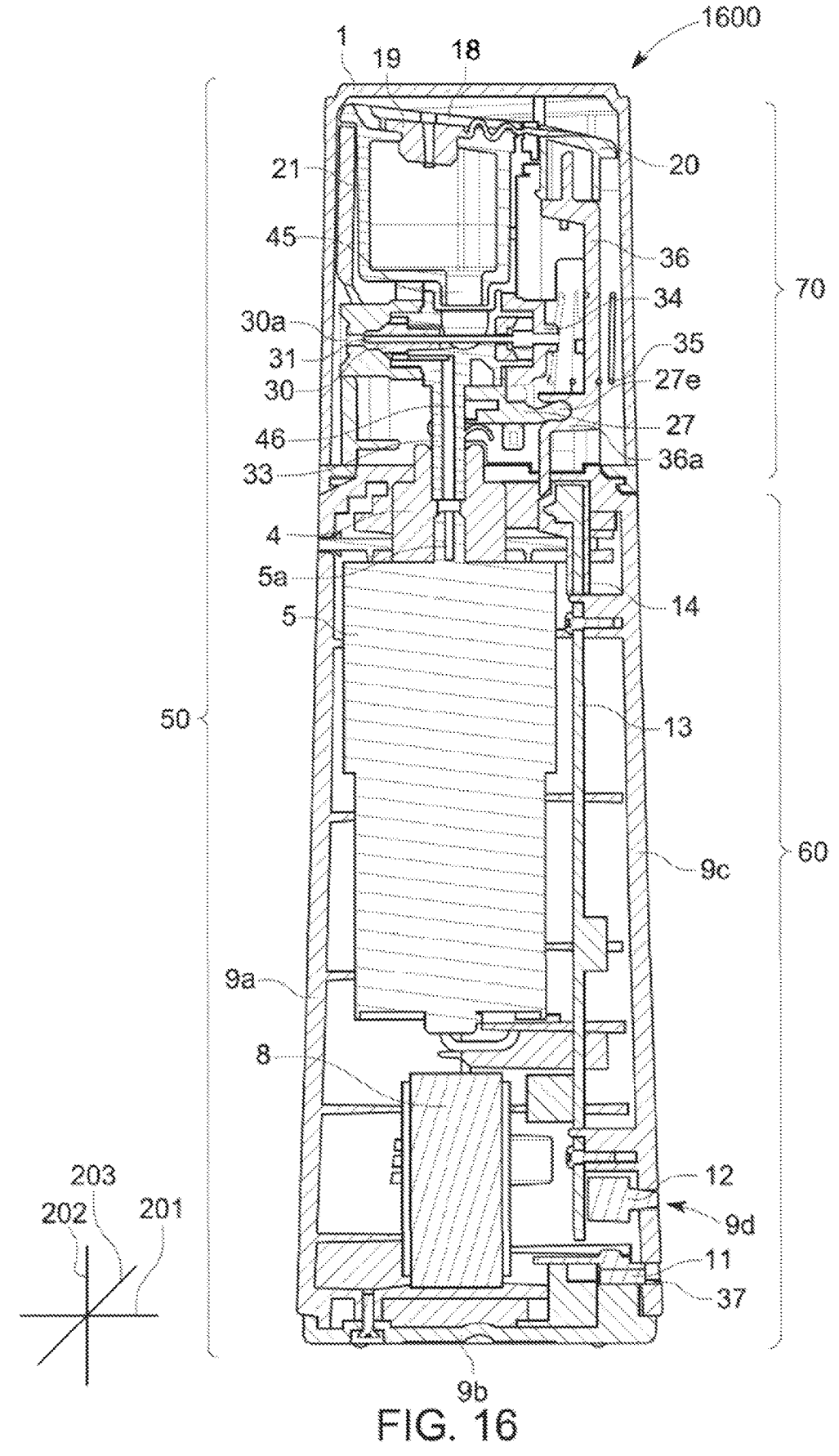
FIG. 16 shows a second cross-sectional view of the atomizer of the present disclosure.

Referring now to FIG. 16, a second cross-sectional view 1600 depicts the atomizer 50. As shown, the body module 60 may be positioned below the head module 70 with respect to the vertical axis 202. Further, and as shown, the cap 1 may cover the head module 70.

Various components of the body module 60 may be supported by one or more of the front body casing 9a, the bottom body casing 9b, and the back body casing 9c. The air pump 5 may be positioned below the pump-to-head connector 4 with respect to the vertical axis 202. The air pump 5 may include the air outlet 5a, which may couple to the air passage 46 of the process chamber 33. As such, the process chamber 33 may be fluidically coupled to the air pump 5 via the air passage 46 and the air outlet 5a.

The battery 8 may be positioned below the air pump 5 with respect to the vertical axis 202. The charging circuit board 11 may be positioned below the charging light source 12 with respect to the vertical axis 202. A charging port 37 may be included in the back body casing 9c such that an external power source may selectively couple to the charging circuit board 11. Further, an aperture 9d may be included in the back body casing 9c above the charging port 37 with respect to the vertical axis 202 such that the charging light source 12 may be visible, and may communicate the charging status of the battery 8. The PCB 13 may be positioned above the charging circuit board 11 with respect to the vertical axis 202. Further, the first spacer 14 may be disposed on a top portion of the PCB 13 relative to the vertical axis 202.

The atomization actuator 20 may be disposed above the link rod 36 with respect to the vertical axis 202. Further, the link rod 36 may be disposed above the first spacer 14 with respect to the vertical axis 202. Upon actuation (e.g., depression) of the atomization actuator 20, the link rod 36 may mechanically engage with the PCB 13 via the first spacer 14. The link rod groove 36a of the link rod 36 may further mechanically engage with the connecting element 27e of the hinged connector 27.

The second lid 18 may be positioned above the first lid 19 with respect to the vertical axis 202. Further, the first lid 19 may be positioned above the composition chamber 21 with respect to the vertical axis 202. In the second cross-sectional view 1600, the second lid 18 and the first lid 19 are shown as together being engaged with the composition chamber 21. The composition chamber 21 may be positioned above the process chamber 33 with respect to the vertical axis 202. The composition chamber 21 may include the composition passage 45 which may couple to the process chamber 33. As such, the process chamber 33 may be fluidically coupled to the composition chamber 21 via the composition passage 45. A composition stored in the composition chamber 21 may pass into the process chamber 33 and may exit the atomizer 50 via the orifice 30a of the nozzle 30 during an atomization. Specifically, upon compression of the first spring 35, the needle 31 may be unseated from the fully seated position in the nozzle 30, allowing the composition to exit the atomizer 50. Further, the needle valve cover 34, disposed between the needle 31 and the first spring 35 along the front-to-back axis 201, may move in tandem with the needle 31 and the compression of the first spring 35.

In this way, an atomizer may atomize one or more compositions to deliver one or more film layers to a cornea of an eye. The atomizer may include a head module and a body module, wherein the head module is detachable from the body module. In one example, multiple, interchangeable head modules may be respectively adapted to one of the one or more compositions. In another example, a single head module may apply multiple compositions by means of an adjustable nozzle. In this case, a radius of the nozzle may be adjusted based upon a viscosity of a selected composition. In either example head module, a speed of a motor of an air pump pumping air for the atomization may further be adjusted based upon the viscosity of the selected composition. The technical effect of controlling the atomization based upon the viscosity of the selected composition is that multiple compositions of varying viscosities may be applied utilizing a single device. Said another way, an identity of the composition may be utilized to determine one or more operating parameters of the atomizer such that a tear film may be generated and applied to the cornea of the eye which appropriately mimics biological tear film layers of varying viscosities.

In one example, a method for creating a biomimicry tear film on a cornea, the method comprising forming a multi-layered tear film that includes forming a first smooth conformal biomimicry tear film layer on the cornea. In a first example of the method, the method further includes wherein the first smooth conformal biomimicry tear film layer is an adhesive layer. A second example of the method, optionally including the first example of the method, further includes wherein forming the multilayered tear film further includes forming a second smooth conformal biomimicry tear film layer on the first smooth conformal biomimicry tear film layer. A third example of the method, optionally including one or both of the first and second examples of the method, further includes wherein the second smooth conformal bio-mimicry tear film layer is an aqueous layer. A fourth example of the method, optionally including one or more of the first through third examples of the method, further includes wherein forming the multilayered tear film further includes forming a third smooth conformal biomimicry tear film layer on the second smooth conformal biomimicry tear film layer. A fifth example of the method, optionally includ-ing one or more of the first through fourth examples of the method, further includes wherein the third smooth confor-mal biomimicry tear film layer is an oil layer. A sixth example of the method, optionally including one or more of the first through fifth examples of the method, further includes wherein each of the first smooth conformal bio-mimicry tear film layer, the second smooth conformal bio-mimicry tear film layer, and the third smooth conformal biomimicry tear film layer have a thickness ranging from a single molecule to several molecules (ranging from approxi-mately a few microns to 250 microns), and wherein the thickness of each of the first smooth conformal biomimicry tear film layer, the second smooth biomimicry tear film layer, and the third smooth conformal biomimicry tear film layer is user-defined. A seventh example of the method, optionally including one or more of the first through sixth examples of the method, further includes wherein the first smooth conformal biomimicry tear film layer is formed from a first composition, wherein the second smooth conformal biomimicry tear film layer is formed from a second com-position, and wherein the third smooth conformal biomim-icry tear film layer is formed from a third composition, wherein the first composition includes mucin or mucin-like proteins or molecules, wherein the second composition includes water and one or more electrolytes, and wherein the third composition comprises one or more of phospholipids, cholesterols, cholesterol esters, triglycerides, castor oil, min-eral oil, fish oil, flaxseed oil, unsaturated lipids, hyaluronic acid, soy oil, petrolatum, waxes, anhydrous lanolin, lanolin, oleaginous ingredients, liposomes, ophthalmic emollients, demulcents, and synthetic materials. A eighth example of the method, optionally including one or more of the first through seventh examples of the method, further comprises using an atomizer to form the multilayered tear film. A ninth example of the method, optionally including one or more of the first through eighth examples of the method, further comprises using a microelectromechanical systems module to form the multilayered tear film. A tenth example of the method, optionally including one or more of the first through ninth examples of the method, further includes wherein the mul-tilayered tear film that is formed is optically transparent.

In another example, a system for creating a biomimicry tear film on a cornea, the system comprising a first compo-sition for forming a first layer of the biomimicry tear film, a second composition for forming a second layer of the biomimicry tear film, a third composition for forming a third layer of the biomimicry tear film, and an atomizer for atomizing and spraying the first composition, the second composition, and the third composition to create the bio-mimicry tear film on the cornea. In a first example of the system, the system further includes wherein the first com-position includes mucin or mucin-like proteins or molecules that include a cytoplasmic domain, a membrane-spanning domain, and an extracellular domain. A second example of the system, optionally including the first example of the system, further includes wherein the second composition includes water and one or more electrolytes. A third example of the system, optionally including one or both of the first and second examples of the system, further includes wherein the third composition includes components selected from a group comprising phospholipids, cholesterols, cholesterol esters, triglycerides, castor oil, mineral oil, fish oil, flaxseed oil, unsaturated lipids, hyaluronic acid, soy oil, petrolatum, waxes, anhydrous lanolin, lanolin, oleaginous ingredients, liposomes, ophthalmic emollients, demulcents, and syn-thetic materials. A fourth example of the system, optionally including one or more of the first through third examples of the system, further includes wherein the third composition includes one or more lipid-soluble vitamins. A fifth example of the system, optionally including one or more of the first through fourth examples of the system, further comprises an air pump included within the atomizer, and wherein atom-izing and spraying the first composition, the second com-position, and the third composition includes activating the air pump. A sixth example of the system, optionally includ-ing one or more of the first through fifth examples of the system, further includes wherein the third layer comprises an outermost layer with respect to the cornea, wherein the first layer is disposed adjacent to the cornea, and wherein the second layer is disposed between the first layer and the third layer.

In another example, an apparatus for creating a biomim-icry tear film on a cornea, the apparatus comprising an air pump operable via a motor, at least one composition cham-ber, and a controller that stores user-defined instructions for operating the air pump to atomize and spray a first compo-sition to form a first layer on the cornea that comprises an adhesive layer of the biomimicry tear film, a second com-position to form a second layer on the first layer that comprises an aqueous layer of the biomimicry tear film, and a third composition to form a third layer on the second layer that comprises an oil layer of the biomimicry tear film. In a first example of the apparatus, the apparatus further includes wherein the first composition includes mucin or mucin-like proteins or molecules that include a cytoplasmic domain, a membrane-spanning domain, and an extracellular domain, wherein the second composition includes water and one or more electrolytes, and wherein the third composition com-prises one or more of phospholipids, cholesterols, choles-terol esters, triglycerides, castor oil, mineral oil, fish oil, flaxseed oil, unsaturated lipids, hyaluronic acid, soy oil, petrolatum, waxes, anhydrous lanolin, lanolin, oleaginous ingredients, liposomes, ophthalmic emollients, demulcents, and synthetic materials.

In another example, a method for treating dry eye syn-drome using an atomizer comprises routing a composition stored in a composition chamber of the atomizer into a process chamber of the atomizer via a composition pathway, routing an air flow from an air pump that includes a motor into the process chamber via an air pathway, controlling a speed of a motor and in turn a rate of the air flow based on the composition stored in the composition chamber, establishing an exit pathway where a combination of the composition and the air flow exit the atomizer as a spray mist, and applying the spray mist to a cornea of a user of the atomizer. In a first example of the method, the method further includes wherein controlling the speed of the motor based on the composition further comprises increasing the speed of the motor as a viscosity of the composition increases, and decreasing a speed of the motor as the viscosity of the composition decreases. A second example of the method, optionally including the first example of the method, further includes wherein establishing the exit pathway includes controlling a needle valve assembly that includes a needle and a nozzle, the needle valve assembly included in the process chamber, and wherein controlling the needle valve assembly includes unseating the needle from a fully seated position in the nozzle to establish the exit pathway. A third example of the method, optionally including one or both of the first and second examples of the method, further includes wherein routing the composition stored in the composition chamber into the process chamber includes opening a valve that, when closed, prevents the composition from being routed into the process chamber. A fourth example of the method, optionally including one or more of the first through third examples of the method, further includes wherein routing the composition stored in the composition chamber into the process chamber includes opening a valve that, when closed, prevents the composition from being routed into the process chamber. A fifth example of the method, optionally including one or more of the first through fourth examples of the method, further includes wherein the composition is one of a first composition wherein the spray mist comprises a first spray mist, a second composition wherein the spray mist comprises a second spray mist and a third composition wherein the spray mist comprises a third spray mist, and wherein the first composition mimics an aqueous layer of a tear film, wherein the second composition mimics an oil layer of the tear film, and wherein the third composition mimics an adhesive layer of the tear film. A sixth example of the method, optionally including one or more of the first through fifth examples of the method, further includes wherein applying the spray mist further comprises sequentially applying the first spray mist followed by the second spray mist. A seventh example of the method, optionally including one or more of the first through sixth examples of the method, further includes wherein applying the spray mist further comprises sequentially applying the third spray mist, followed by the first spray mist, which is then followed by the second spray mist.

In another example, a method for treating dry eye syndrome comprises receiving, via a controller of an atomizer, instructions pertaining to atomizing one of a first composition into a first spray mist, a second composition into a second spray mist and a third composition into a third spray mist, routing one of the first composition, the second composition and the third composition into a process chamber of the atomizer based on the instructions, commanding, based on the instructions, a speed of a motor of an air pump to route an air flow into the process chamber, and where air and one of the first composition, the second composition and the third composition exit the process chamber as one of the first spray mist, the second spray mist and the third spray mist, respectively, for application to a cornea of a user of the atomizer. In a first example of the method, the method further includes wherein the instructions pertaining to atomizing one of the first composition, the second composition and the third composition are received at the controller from a customization application communicatively coupled to the controller. A second example of the method, optionally including the first example of the method, further includes wherein the first composition is stored in a first composition chamber of the atomizer, wherein the second composition is stored in a second composition chamber of the atomizer, and wherein the third composition is stored in a third composition chamber of the atomizer, and wherein routing one of the first composition, the second composition and the third composition includes commanding open a first valve to fluidically couple the first composition chamber to the process chamber, commanding open a second valve to fluidically couple the second composition chamber to the process chamber and commanding open a third valve to fluidically couple the third composition chamber to the process chamber, respectively. A third example of the method, optionally including one or both of the first and second examples of the method, further includes wherein commanding the speed of the motor further comprises commanding the motor to a first speed for atomizing the first composition, commanding the motor to the second speed for atomizing the second composition, and commanding the motor to the third speed for atomizing the third composition. A fourth example of the method, optionally including one or more of the first through third examples of the method, further includes wherein air and one of the first composition, the second composition and the third composition exit the process chamber via a nozzle, where a radius of the nozzle is adjustable, and wherein the controller further receives instructions for adjusting the radius of the nozzle as a function of the first composition, the second composition and the third composition. A fifth example of the method, optionally including one or more of the first through fourth examples of the method, further includes wherein the instructions for routing one of the first composition, the second composition and the third composition to the process chamber further comprise instructions for routing an amount of one of the first composition, the second composition and the third composition. A sixth example of the method, optionally including one or more of the first through fifth examples of the method, further includes wherein the first composition includes water and electrolytes, wherein the second composition includes one of phospholipids, cholesterols, cholesterol esters, triglycerides, castor oil, mineral oil, fish oil, flaxseed oil, unsaturated lipids, hyaluronic acid, soy oil, petrolatum, waxes, anhydrous lanolin, lanolin, oleaginous ingredients, liposomes, ophthalmic emollients, demulcents, and synthetic materials, and wherein the third composition includes mucin or mucin-like proteins or molecules that include a cytoplasmic domain, a membrane-spanning domain, and an extracellular domain. A seventh example of the method, optionally including one or more of the first through sixth examples of the method, further includes wherein the instructions pertaining to atomizing one of the first composition, the second composition and the third composition further comprise instructions related to an order in which the first composition, the second composition and the third composition are atomized into the first spray mist, the second spray mist and the third spray mist, respectively.

In another example, an atomizer system for applying a spray mist to a cornea or skin comprises a remote computing device implementing a customization application, an atomizer that includes a plurality of composition chambers, an air pump operable via a motor, a process chamber that receives a composition from one of the plurality of composition chambers at a time and an air flow from the air pump, a nozzle that receives a mixture of the composition and the air flow for generating the spray mist, and a controller of the atomizer that receives a set of instructions for applying the spray mist from the customization application. In a first example of the atomizer system, the atomizer system further includes wherein the set of instructions include instructions for controlling one or more of a radius of the nozzle and a rate of the air flow provided to the process chamber. A second example of the atomizer system, optionally including the first example of the atomizer system, further includes wherein the set of instructions pertain to one or more of a desired amount of the composition to be applied, a desired sequence of application of compositions stored in the plurality of composition chambers, a desired droplet size of the spray mist, and a desired duration of application of the spray mist. A third example of the atomizer system, optionally including one or both of the first and second examples of the atomizer system, further includes wherein each of the plurality of composition chambers include a corresponding valve, and wherein the controller controls the corresponding valve based on the set of instructions.

In another example, an atomizer for administering a spray mist to a cornea or skin comprises a removable head module that includes a composition chamber and a process chamber, the process chamber fluidically coupled to the composition chamber via a composition passage, a body module that includes an air pump and a motor of the air pump for supplying air to the process chamber via an air passage, a needle valve assembly including a needle and a nozzle, the needle valve assembly included in the process chamber, and a controller included in the body module storing instructions for adjusting a speed of the motor as a function of a viscosity of a composition included in the composition chamber. In a first example of the atomizer, the atomizer may further comprise a rechargeable battery included within the body module for providing power to the motor. A second example of the atomizer, optionally including the first example of the atomizer, further comprises an atomization actuator coupled to the removable head module for actuating on the motor and unseating the needle from a fully seated position in the nozzle, where the spray mist exits the nozzle when the motor is activated and the needle is unseated. A third example of the atomizer, optionally including one or both of the first and second examples of the atomizer, further includes wherein the controller receives instructions for adjusting the speed of the motor from a customization application.

In another example, an atomizer for administering a spray mist to a cornea or skin comprises a composition cavity included in a head module of the atomizer, wherein the composition cavity includes a first composition chamber having a first valve, a second composition chamber having a second valve, and a third composition chamber having a third valve, a process chamber included in the head module that independently receives a first composition from the first composition compartment when the first valve is open, a second composition from the second composition compartment when the second valve is open, and a third composition from the third composition compartment when the third valve is open, a body module mechanically coupled to the head module, the body module including an air pump operable via a motor for supplying an air flow to the process chamber, and a nozzle fluidically coupled to the process chamber where one of the first composition, the second composition, and the third composition respectively exits the atomizer as one of a first spray mist, a second spray mist, and a third spray mist. In a first example of the atomizer, the atomizer further includes where the head module includes a first atomization actuator, a second atomization actuator, and a third atomization actuator, where actuation of the first atomization actuator activates the motor and opens the first valve that induces the first composition to flow into the process chamber, where actuation of the second atomization actuator activates the motor and opens the second valve that induces the second composition to flow into the process chamber, and where actuation of the third atomization actuator activates the motor and opens the third valve that induces the third composition to flow into the process chamber. A second example of the atomizer, optionally including the first example of the atomizer, further includes wherein the first valve comprises a first plunger extending through the first composition compartment that, when the first atomization actuator is actuated, results in displacement of the first plunger to fluidically couple the first composition compartment to the process chamber, wherein the second valve comprises a second plunger extending through the second composition compartment that, when the second atomization actuator is actuated, results in displacement of the second plunger to fluidically couple the second composition compartment to the process chamber, and wherein the third valve comprises a third plunger extending through the third composition compartment that, when the third atomization actuator is actuated, results in displacement of the third plunger to fluidically couple the third composition compartment to the process chamber. A third example of the atomizer, optionally including one or both of the first and second examples of the atomizer, further comprises a link rod that extends from the head module to the body module, a printed circuit board positioned in the body module, and where actuation of one of the first atomization actuator, the second atomization actuator, and the third atomization actuator induces movement of the link rod to mechanically couple the link rod to the printed circuit board that in turn activates the motor of the air pump to provide the air flow to the process chamber. A fourth example of the atomizer, optionally including one or more of the first through third examples of the atomizer, further includes wherein a radius of the nozzle are adjustable. A fifth example of the atomizer, optionally including one or more of the first through fourth examples of the atomizer, further includes where a speed of the motor is adjustable.

In another example, an atomizer for administering a spray mist onto a cornea or skin comprises a head module, a body module positioned below the head module with respect to a vertical axis of the atomizer, the body module removably coupled to the head module, a composition chamber included in the head module, a process chamber included in the head module, the process chamber positioned below the composition chamber with respect to the vertical axis, the process chamber fluidically coupled to the composition chamber via a composition passage, an air pump with a motor positioned in the body module, where the air pump is fluidically coupled to the process chamber via an air passage of the process chamber that extends along the vertical axis from the head module to the body module, a needle valve assembly included in the process chamber, the needle valve assembly including a needle and a nozzle with an orifice, the orifice positioned at a front frame of the head module and where the needle valve assembly extends along a front-to-back axis of the atomizer perpendicular to the vertical axis, a needle valve cover mechanically coupled to the needle, and a first spring connected to the needle valve cover that biases the needle to a fully seated position in the nozzle, an atomization actuator, a link rod extending along the vertical axis from the head module to the body module, the link rod selectively mechanically coupled to the atomization actuator, a hinged connector with a connecting element positioned along the front-to-back axis of the atomizer that fits into a link rod groove of the link rod, where movement of the link rod in a downward direction with respect to the vertical axis rotationally mechanically engages the hinged connector with the needle valve cover to compress the first spring and unseat the needle from the fully seated position in the nozzle, a printed circuit board included in the body module, wherein the downward direction of movement of the link rod mechanically engages the link rod with the printed circuit board to activate the motor to produce an air flow to the process chamber, and wherein a composition stored in the composition chamber flows through the process chamber and exits the orifice as the spray mist when the needle is unseated from the fully seated position while the motor is activated. In a first example of the atomizer, the atomizer further comprises a rechargeable battery included in the body module for providing power to the motor, the rechargeable battery positioned below the motor with respect to the vertical axis, a charging circuit board included behind the battery with respect to the front-to-back axis of the atomizer, a charging port for selectively coupling an external power source to the charging circuit board, the charging port included on a back face of the body module, and a charging light source electrically coupled to the charging circuit board and included on the back face of the body module above the charging port with respect to the vertical axis to indicate a charging status of the rechargeable battery. A second example of the atomizer, optionally including the first example of the atomizer, further comprises a power light source positioned on a front face of the body module that is illuminated in response to activation of the motor. A third example of the atomizer, optionally including one or both of the first and second examples of the atomizer, further comprises a first lid for the composition chamber that sealingly engages with an upper compartment of the composition chamber, and a second lid for the composition chamber that includes one or more male connectors extending from a bottom face of the second lid that sealingly engage with one or more female connectors associated with a top face of the first lid. A fourth example of the atomizer, optionally including one or more of the first through third examples of the atomizer, further includes wherein the first lid is composed of silicone. A fifth example of the atomizer, optionally including one or more of the first through fourth examples of the atomizer, further includes wherein the needle valve cover includes a first prong and a second prong, where the first prong and the second prong slidingly engage along the front-to-back axis with a first groove and a second groove, respectively, included on the process chamber, the first groove positioned on a first outer face of the process chamber and the second groove positioned on a second outer face of the process chamber. A sixth example of the atomizer, optionally including one or more of the first through fifth examples of the atomizer, further includes wherein the hinged connector includes a first fin and a second fin that extend along the vertical axis, and wherein engaging the hinged connector with the needle valve cover further comprises the first fin of the hinged connector contacting the first prong of the needle valve cover and the second fin of the hinged connector contacting the second prong of the needle valve cover. A seventh example of the atomizer, optionally including one or more of the first through sixth examples of the atomizer, further includes wherein the process chamber is surrounded by a body frame that includes two female acceptor elements for receiving two pins extending from the hinged connector. A eighth example of the atomizer, optionally including one or more of the first through seventh examples of the atomizer, further includes wherein a speed range of the motor is from 100 revolutions per minute to 110,000 revolutions per minute. A ninth example of the atomizer, optionally including one or more of the first through eighth examples of the atomizer, further comprises a first mechanical fastener and a second mechanical fastener coupled to a head casing of the head module, and a first mechanical fastener receiving element and a second mechanical fastener receiving element each positioned on a top face of the body module, where insertion of the first mechanical fastener into the first mechanical fastener receiving element and insertion of the second mechanical fastener into the second mechanical fastener receiving element mechanically couples the head module to the body module, and wherein the first mechanical fastener and the second mechanical fastener are biased to a first locked position and a second locked position, respectively, via a second spring and a third spring, and wherein compression of the second spring and the third spring disengages or releases the first mechanical fastener and the second mechanical fastener from the first mechanical fastener receiving element and the second mechanical fastener receiving element, respectively.

FIGS. 2-7B and 12A-16 show example configurations with relative positioning of the various components described herein. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

In some embodiments, the methods and apparatus described in various examples above are utilized to implement and/or supplement the method and apparatus disclosed below. In some embodiments, it is recognized that the lipid layer of the artificial tear film plays a vital role in preventing evaporation of moisture from the eyes, and in some embodiments, applying the lipid layer alone or applying a lipid layer with an aqueous layer (e.g., lipid layer applied over aqueous layer, or irrespective of the order of application, etc.) are effective in improving the dry eye condition.

In some embodiments, in addition to the order by which the compositions corresponding to different layers of the artificial tear film are applied to the eye, dispensing volumes of the compositions corresponding to the different layers of the artificial tear film also play an important role in the effectiveness of the resulting artificial tear film. Specifically, a smaller dispensing volume achieved by even application of a mist of small average droplet size have more superior performance compared to a few large liquid drops from a dropper-type dispenser. Contrary to conventional logic, a larger quantity of artificial tear liquid, and/or a mixture of compositions corresponding to multiple artificial tear layers, applied to the eye perform more poorly compared to applying only a smaller quantity of liquid that is commensurate with the natural tear volume in the eye and/or application of only the composition of the lipid layer on the cornea surface. The following method focus on the advantages of small volume lipid layer formula application that effectively slows down tear evaporation.

In general, average tear volume is about 7 μl, with a range from 3 μls to 10 μls. The aqueous layer takes up about 80% of the tear volume, while the lipid layer takes up about 3-4% of the total tear volume which amounts to less than 0.03 ul on average. With conventional eye droppers, the glass or plastic dropper tubes deliver drops with a volume that ranges from 25 μL to 75 L (e.g., on average a 40 μL drop size). It is difficult to control the drop size below 25 μL using conventional eye droppers, and as a result, much of the ophthalmic liquid deposited on the eye exits the eye when the patient blinks. In contrast, using a dispenser with a sprayer to deliver an ophthalmic solution is more effective in delivering a smaller volume of liquid. The solution can be delivered to the eye surface as micro droplets achieving a dispensing volume range from 0.01 μl to 20 μl. Even with eye dropper type dispensers, by reducing the dispensing opening or increasing dispensing pressure, etc., to reduce the droplet size to about 1 ul-10 ul, the resulting application will be more effective than that achieved using conventional eye droppers. In some embodiments, a lipid-only or lipid-dominant composition (e.g., a mixture of non-aqueous liquids and optionally some gases, without any water or with less than 5% water) is used instead of a mixture containing compositions corresponding to both the lipid layer and the aqueous layer. A dispenser configured to dispense a total volume of 0.05 μl to 1 μl of the lipid-only or lipid dominant composition, which results in a lipid layer that much more closely match the lipid presence in human tears.

It is also emphasized that the high oil concentration in the lipid layer formula is important regardless of whether a complete layer is formed on the surface of the eye or not. Currently, oil-based ointments and oil-based emulsions are available on the market. Ointments contains high oil ingredients but are in gel form. It's typically used at night due to its greasiness and opaqueness. It is quite uncomfortable and inconvenient for the patient to apply the gel and endure the loss of clear vision. This is especially difficult for pediatric use, because children cannot tolerate the discomfort and will rub the eye to remove the greasy composition. As disclosed herein, the lipid formula that can be dispensed using a dropper type dispenser with reduced droplet size or a mist-generation dispenser has a very high percentage of oil ingredients (e.g., 95-100%, or 100%) and is in liquid form (e.g., as opposed to gel form). In some embodiments, the composition includes 50% mineral oil and 50% light mineral oil; or 45% mineral oil, 50% light mineral oil, and 5% white petroleum. The viscosity of the lipid layer formula can be ranged from 5 cp to 50 cp by varying the percentage of mineral oil, light mineral oil, and white petroleum. The resulting lipid layer formula is transparent, non-greasy, and non-water-soluble, and can be effective for 4-12 hours on the eye surface to slow down tear evaporation.

In some embodiments, the oil-based lipid formula will spread conformally on the eye surface (e.g., directly on the exterior surface of the cornea, over the natural tear film on the exterior of the cornea, over an aqueous layer of an artificial tear film, over conventional artificial tear film formed by an artificial tear mixture (e.g., a mixture of ingredients of mucin, aqueous, and lipid layers of natural tear) deposited using a conventional dropper, etc.) and form a thin layer with thickness ranging from 10 nm to 10 um.

In some embodiments, a method for delivering the one or more film layers that mimic layers of tear film to an eye is described herein. The method optionally utilizes the dispensing systems described herein, though it may be understood that similar methods may be applied to other systems without departing from the scope of this disclosure. In some embodiments, certain steps may be conducted via a user of the dispensing systems while other steps may include instructions received from the customization application. In some embodiments, steps that are controlled via such instructions are optionally carried out via a controller, and may be stored at the controller (e.g., a controller implemented by one or more micro-computer processors) as executable instructions in non-transitory memory. Instructions for carrying out the method may be executed by the controller based on instructions stored on a memory (e.g., 804) and optionally in conjunction with instructions received from a remote computing device running a customization application for use with the dispenser. In some embodiments, the controller may employ one or more actuators to adjust operations of one or more elements described herein. More specifically, the controller may control open and closed positions of valve(s) (e.g., 41) for each composition chamber, may control a radius of the nozzle (e.g., 30), and may control a speed of the motor (e.g., 6) of the air pump (e.g., 5), for example.

In some embodiments, a method of treating dry eye includes applying one or more distinct compositions (e.g., mixtures of ingredients that correspond to different layers of natural tear, or artificial tear, medication, etc.) to a surface that corresponds to a cornea of an eye (e.g., exterior surface of the eye ball, interior surface of a contact lens, exterior surface of a contact lens, etc.). In some embodiments, applying the one or more distinct compositions includes generating and propelling (e.g., generating droplets from a liquid and forcing the droplets to move into a preset general direction) a respective mist of a first composition (e.g., the lipid layer formula, a mixture of oils, a mixture of non-aqueous liquids, etc.) of the one or more compositions toward the surface that corresponds to the cornea of the eye, wherein the first composition consists one or more non-aqueous substances (e.g., oils, a pre-established composition with oil-based ingredients having preset proportions, etc., without any water, or with less than 5% of water or aqueous solutions, etc.), wherein the respective mist (e.g., micro-droplets of liquid, oil droplets, etc.), including droplets of the one or more non-aqueous substances, after reaching the surface that corresponds to the cornea of the eye, forms a first film layer that corresponds to a lipid layer of an artificial tear film (e.g., a complete film layer, or patches of an oil film distributed over the surface of the cornea, etc.). In some embodiments, the first composition is deposited over the cornea of the eye directly without first depositing another liquid or gel composition immediately prior to the first composition. In some embodiments, the first composition is deposited over a layer of artificial tear composition (e.g., artificial tear deposited using a dropper dispenser, a layer of aqueous solution, etc.). In some embodiments, the first composition is deposited using one of the dispensers that atomize or nebulize the first composition, as described in the present disclosure.

In some embodiments, a controller of the dispenser or a user of the dispenser controls the dispenser of the first composition such that a dispensing volume of the first composition is within a range of 0.01-20 microliters per application during normal operation. In some embodiments, the dispenser has a structure and/or configuration (e.g., nozzle size, nozzle shape, nozzle count, dispensing pressure, dispensing speed, actuation force/speed/frequency, liquid chamber size/shape, etc.) that controls the dispensing volume of the first composition to be within the range of 0.01-20 microliters per spray/actuation/activation, etc. In some embodiments, the dispenser is optionally activated multiple times to achieve the required dispensing volume. In some embodiments, the dispenser is configured to prevent repeated activations within a threshold amount of time to exceed the preset range for the dispensing volume. In some embodiments, warning is presented by the dispenser when a preset number of repeated activation is being approached or exceeded to avoid excessive amount of the first composition being deposited per application. In some embodiments, a controller is used to control various parameters of the dispenser such that the dispending volume per activation of the dispenser is controlled to be within the preset range.

In some embodiments, the dispenser of the first composition is controlled (e.g., by the structure of the dispenser, but the user, and/or by the controller, etc.) such that a dispensing volume of the first composition is within a range of 0.01-10 microliters per application during normal operation (e.g., per activation of the dispenser, per use of the dispenser with a preset number of activations within a threshold amount of time, etc.).

In some embodiments, one or more parameters (e.g., nozzle size, nozzle shape, nozzle count, dispensing pressure, dispensing speed, actuation force/speed/frequency, liquid chamber size/shape, dispensing volume, etc.) of the dispenser of the first composition is controlled (e.g., by the structure of the dispenser, but the user, and/or by the controller, etc.) such that the first film layer of the one or more non-aqueous substance has a thickness within a range of 10 nm-200 nm on the surface that corresponds to the cornea of the eye.

In some embodiments the dispenser of the first composition is controlled (e.g., by the structure of the dispenser, but the user, and/or by the controller, etc.) such that an average droplet size of the respective mist of the first composition is within a range of 0.01 microliters-2 microliters. In some embodiments, the dispensing volume can be 0.1-20 microliter for each spray, with average droplet size with the range of 0.01 microliters to 2 microliters. In some embodiments, at a preset spray distance of between 1 cm to 20 cm, the spray area is about 2 cm×2 cm or greater. In embodiments, the layer thickness for the lipid layer ranges between 10 nm to 200 nm using a spray-type dispenser. In some embodiments, the layer thickness for the aqueous layer ranges between 3 μm to 20 μm using the spray-type dispenser. In some embodiments, the layer thickness for the mucin layer ranges between 10 μm to 30 μm using the spray-type dispenser or a dropper-type dispenser. In some embodiments, the spray area corresponds to average eye area (e.g., 2 cm×2 cm, or larger), and the corresponding dispensing volume is 0.02 microliter-60 microliter total. In some embodiments, the dispensing volume of each spray is a smaller range such as 0.01 microliter to 10 microliter. A large volume can be achieved by multiple/repeated activation/actuations of the dispenser.

In some embodiments, the one or more non-aqueous substances, when combined in the first composition, is a liquid with a viscosity in the range of 5 centipoises to 50 centipoises. In some embodiments, the first composition is disposed into a chamber of the dispenser premixed, or is mixed within the chamber close to the time of use. In some embodiments, the first composition includes 95%-100% oils that are not water-soluble. In some embodiments, the first composition includes one or more ingredients from the list of emollient drug products for ophthalmic drugs published in Title 21-Food and Drugs, Chapter I—Food and Drug Administration Department of Health and Human Services Subchapter D—Drugs for Human use, Part 349 Ophthalmic Drug Products for Over-The-Counter Human Use, which is incorporated herein by its entirety, as is and as may be updated from time to time during the pendency of this patent. In some embodiments, the first composition includes one or more ingredients from: a) Lanolin preparations: (1) Anhydrous lanolin, 1 to 10 percent in combination with one or more oleaginous emollient agents included in the monograph; and/or (2) Lanolin, 1 to 10 percent in combination with one or more oleaginous emollient agents included in the monograph; and/or (b) Oleaginous ingredients: (1) Light mineral oil, up to 50 percent in combination with one or more other emollient agents included in the monograph; (2) Mineral oil, up to 50 percent in combination with one or more other emollient agents included in the monograph; (3) Paraffin, up to 5 percent in combination with one or more other emollient agents included in the monograph; (4) Petrolatum, up to 100 percent; (5) White ointment, up to 100 percent; (6) White petrolatum, up to 100 percent; (7) White wax, up to 5 percent in combination with one or more other emollient agents included in the monograph; and/or (8) Yellow wax, up to 5 percent in combination with one or more other emollient agents included in the monograph.

In some embodiments, the surface that corresponds to the cornea of the eye is an exterior surface of the cornea and the mist is directly deposited onto the exterior surface of the cornea without first applying other liquid or gels. In some embodiments, the surface that corresponds to the cornea of the eye is an exterior surface of an aqueous layer that has been deposited on the exterior surface of the cornea and the mist is deposited onto the exterior surface of the aqueous layer. In some embodiments, the first composition quickly spreads over and conforms to the surface shape of the aqueous layer or the shape of the cornea without mixing with the aqueous layer or the natural tear on the cornea.

In some embodiments, the first composition has a refractive index in the range of 1.46-1.64 that more closely corresponds to a refractive index of the lipid layer of natural tear than to an aqueous layer of the natural tear (e.g., natural tear with refractive index of 1.33). In some embodiments, the first composition has a refractive index in the range of 1.25-1.4 that more closely corresponds to a refractive index of the cornea than an aqueous layer of natural tear does.

In some embodiments, the first composition has a surface tension in the range of 10-100 mN/m that, when deposited over an aqueous layer (e.g., the aqueous layer of the artificial tear film that has been deposited using the same dispenser or another dispenser, the aqueous layer of the natural tear with incomplete or insufficient natural lipid layer, etc.), spreads over the aqueous layer in within a time window ranging 1-20 seconds.

In some embodiments, applying the one or more distinct compositions to the surface that corresponds to the cornea of the eye includes: prior to generating and propelling the respective mist of the first composition of the one or more compositions toward the surface that corresponds to the cornea of the eye, applying (e.g., using the same dispenser connected to a different fluid chamber, using a different dispenser, etc.) a second composition that includes one or more aqueous substances (e.g., without any non-aqueous ingredients, without oils, or ingredients corresponding to the lipid layer of the artificial tear film, etc.) to the surface that corresponds to the cornea of the eye (e.g., directly on the exterior surface of the cornea (e.g., over a natural tear film) or over an artificial mucin layer, etc.), wherein the one or more aqueous substance form a second film layer that corresponds to an aqueous layer of the artificial tear film, and wherein the respective mist is applied to the second film layer when propelled toward the surface that corresponds to the cornea of the eye (e.g., the artificial lipid layer is deposited over the artificial aqueous layer and expands to coat the aqueous layer due to surface tension difference and non-mixing between the first composition and the second composition).

In some embodiments, the one or more dispensers of the first composition and the second composition are controlled (e.g., by their respective structures, by the user, and/or by the controller, etc.) such that respective quantities of the first composition and the second composition that are dispensed per application (e.g., per respective spray of the first composition and the second composition, per preset combination of preset numbers of sprays of the first composition and the second composition, etc.) correspond to a preset ratio between the first composition and the second composition (e.g., ratio corresponding to natural ratio of aqueous volume and lipid volume in natural tear). In some embodiments, the ratio is controls by varying the relative numbers of sprays for the first composition and the second composition. In some embodiments the ratio is controlled by varying the nozzle sizes and/or spray speed used for dispensing the first composition and the second composition. In some embodiments, applying the one or more distinct compositions to the surface that corresponds to the cornea of the eye includes: prior to applying the second composition that includes the one or more aqueous substances to the surface that corresponds to the cornea of the eye, applying a third composition to the surface that corresponds to the cornea of the eye to form a mucin layer of the artificial tear film. In some embodiments, the first composition and the second composition are applied using a single device that dispenses the first and second compositions using respective dispensing apparatus with distinct dispensing parameters corresponding to the first and second compositions. In some embodiments, the third composition is also applied using the same device. In some embodiments, the principles and mechanisms used for varying the ratio of the dispensing volumes for the first composition and the second composition also apply to the third composition. In some embodiments, the third composition is applied using a different dispenser as the dispensing volume tolerance is larger compared to the second and first compositions.

In some embodiments, the first composition comprises one or more of phospholipids, cholesterols, cholesterol esters, triglycerides, castor oil, mineral oil, fish oil, flaxseed oil, unsaturated lipids, hyaluronic acid, soy oil, petrolatum, waxes, anhydrous lanolin, lanolin, oleaginous ingredients, liposomes, ophthalmic emollients, demulcents, and synthetic oils. In some embodiments, the first composition includes no water.

In some embodiments, an apparatus for treating dry eye is disclosed. The apparatus optionally includes any of the apparatuses disclosed herein and/or implements the methods described herein with or without modifications. In some embodiments, characteristics of the apparatus are described with respect to various methods disclosed herein and are not repeated in the interest of brevity. In some embodiments, the apparatus includes one or more composition chambers, including a first composition chamber containing a first composition, wherein the first composition includes one or more non-aqueous substances (e.g., oils, non-water-soluble ingredients, etc.); and an air pump (or equivalents) that is fluidly connected to the one or more composition chambers and that is configured to apply one or more distinct compositions to a surface that corresponds to a cornea of an eye, wherein: the air pump (or equivalents) is configured to generate and propel a respective mist of the first composition toward the surface that corresponds to the cornea of the eye during activation, wherein the respective mist, including droplets of the one or more non-aqueous substances, after reaching the surface that corresponds to the cornea of the eye, forms a first film layer that corresponds to a lipid layer of an artificial tear film. In some embodiments, the air pump includes vibrating components that generates and propel the mist, and may not require air to propel the mist. In some embodiments, the air pump is configured to dispense the first composition with a dispensing volume that is within a range of 0.01-20 microliters per application during normal operation of the apparatus. In some embodiments, the air pump is configured to dispense the first composition with a dispensing volume that is within a range of 0.01-10 microliters per application during normal operation. In some embodiments, the air pump is configured to operate with one or more adjustable parameters such that the first film layer of the one or more non-aqueous substance has a thickness within a range of 10 nm-200 nm on the surface that corresponds to the cornea of the eye. In some embodiments, the air pump is configured to dispense the first composition with an average droplet size in the respective mist of the first composition that is within a range of 0.01-2 microliters. In some embodiments, the one or more non-aqueous substances when combined in the first composition, is a liquid with a viscosity in the range of 5 centipoises to 50 centipoises. In some embodiments, the first composition includes 95%-100% oils that are not water-soluble. In some embodiments, the surface that corresponds to the cornea of the eye is an exterior surface of the cornea. In some embodiments, the first composition has a refractive index in the range of 1.25-1.4 that more closely corresponds to a refractive index of the cornea than an aqueous layer of natural tear does. In some embodiments, the air pump is configured to, prior to generating and propelling the respective mist of the first composition of the one or more compositions toward the surface that corresponds to the cornea of the eye, apply a second composition that includes one or more aqueous substances to the surface that corresponds to the cornea of the eye, wherein the one or more aqueous substance form a second film layer that corresponds to an aqueous layer of the artificial tear film, and wherein the respective mist is applied to the second film layer when propelled toward the surface that corresponds to the cornea of the eye. In some embodiments, the air pump is configured to dispense the first composition and the second composition with a combined volume of the first composition and the second composition that is dispensed to the surface that corresponds to the cornea of the eye not exceeding 60 microliters per application during normal operation. In some embodiments, the air pump is configured to dispense the first composition and the second composition such that respective quantities of the first composition and the second composition that are dispensed per application correspond to a preset ratio between the first composition and the second composition. In some embodiments, the air pump is configured to, prior to applying the second composition that includes the one or more aqueous substances to the surface that corresponds to the cornea of the eye, apply a third composition to the surface that corresponds to the cornea of the eye to form a mucin layer of the artificial tear film. In some embodiments, the apparatus dispenses the first composition and the second composition using the air pump with distinct dispensing parameters corresponding to the first and second compositions. In some embodiments, the first composition comprises one or more of phospholipids, cholesterols, cholesterol esters, triglycerides, castor oil, mineral oil, fish oil, flaxseed oil, unsaturated lipids, hyaluronic acid, soy oil, petrolatum, waxes, anhydrous lanolin, lanolin, oleaginous ingredients, liposomes, ophthalmic emollients, demulcents, and synthetic oils. Other features of the apparatus are described throughout the disclosure and are not repeated herein.

Atomizer for Delivery of Ophthalmic and Other Fluids

In some embodiments, the methods and apparatus described in various examples above are utilized to implement and/or supplement the method and apparatus disclosed below.

Some embodiments of the present disclosure are directed to a device (e.g., an apparatus) that can be used for delivery of ophthalmic fluids, nasal solutions, and/or fluid-based vaccines to a person's sensory organs, such as the eye, nose, and/or ear.

In accordance with some embodiments, a device (e.g., apparatus, an atomizer, etc.) for delivering ophthalmic fluids and/or fluid-based vaccines includes a housing (e.g., an outer case, a casing, a detachable housing, a detachable housing, etc.). The housing includes a first end and a second end opposite to the first end. The first end includes an opening. The device includes a compartment (e.g., a region) positioned at (e.g., next to, adjacent to, proximate to) the first end. In some embodiments, the compartment is capable of holding a fluid (e.g., a liquid). In some embodiments, the fluid is contained in a liquid reservoir. IN some embodiments, the liquid reservoir is fully sealed. For example, in some embodiments, the liquid reservoir includes an enclosed capsule, a fully sealed capsule, a fully sealed liquid reservoir, etc., that is positioned in the compartment. The device includes an air pump positioned within (e.g., inside) the housing, at (e.g., toward) the second end. The device includes an actuator (e.g., an electric actuator) positioned within the housing, between the compartment and the air pump. The actuator includes an extendible (and retractable) piston (e.g., a lead screw) that is configured to extend (and retract) laterally toward the compartment.

In some embodiments, during operation of the device, the actuator causes the piston executes a translational movement. In some embodiments, the piston extends towards the liquid reservoir, and exerts a force (e.g., push force) on (e.g., against) the liquid reservoir. In some embodiments, the force exerted by the piston on the liquid reservoir causes fluid to be expelled (e.g., ejected) from the liquid reservoir (e.g., at the first end). In some embodiments, the air pump is configured to atomize the fluid as (e.g., during) the fluid is expelled from the liquid reservoir (e.g., at the first end).

In some embodiments, the device includes a controller (e.g., one or more processors and memory). The controller includes (e.g., stores) instructions that, when executed by the controller, cause the controller to operate the actuator such that the piston extends (e.g., laterally) (e.g., executes a translational movement) towards the liquid reservoir and contacts the liquid reservoir, thereby exerting (e.g., applying) a force (e.g., a push force) on the liquid reservoir. In some embodiments, the liquid reservoir is an enclosed (e.g., fully sealed) container (e.g., a capsule). The force exerted by the piston causes a portion of the liquid reservoir to break and fluid to be expelled (e.g., ejected) from the liquid reservoir at the first end. The controller includes instructions that, when executed by the controller, cause the controller to operate the air pump to atomize (e.g., generate a fine mist of) the fluid to form droplets as it is expelled from the liquid reservoir. In some embodiments, the droplets have a size (e.g., a diameter) not exceeding 100 μm. In some embodiments, the atomized fluid is propelled toward to person's sensory organ, such as the eye, nose, or ear.

In some embodiments, the controller includes instructions that, when executed by the controller, cause the controller to operate the air pump via a motor at an air flow rate of 1-4 liters per minute.

In some embodiments, the fluid in the liquid reservoir has a volume ranging from 300 μl to 1000 μl.

In some embodiments, the liquid reservoir includes a diameter ranging from 5 mm to 15 mm.

In some embodiments, the air pump is operable via a motor.

In some embodiments, the actuator is operable via a motor.

In some embodiments, the piston has a stroke that does not exceed 100 mm. In some embodiments, the piston has a stoke ranging from 5 mm to 100 mm. In some embodiments, the piston has a stroke ranging from 50 mm to 100 mm.

In some embodiments, the actuator comprises a linear actuator.

In some embodiments, the linear actuator includes a motor (e.g., a linear motor, a DC motor or an AC motor) configured to convert rotational motion into a translational motion (e.g., straight movement, linear movement, push/pull movement, backward and forward movement) of the piston.

In some embodiments, the linear actuator includes three main components: spindle, motor and gears In some embodiments, the linear actuator is a stepper motor that incorporate the piston (e.g., a lead screw) as the rotor, which translates motor torque into linear thrust. The linear thrust produces a linear motion along an axis (e.g., an axis parallel to a length of the housing), which produces a linear force along its length.

In some embodiments, the compartment is positioned within the housing, at (e.g., proximate to, adjacent to) the first end.

In some embodiments, the device includes a spray head (e.g., a disposable spray head, a detachable spray head, etc.) positioned at the first end. The compartment is positioned in the spray head. In some embodiments, the device includes a removable spray head case that protects the spray head.

In some embodiments, the spray head includes a nozzle.

In some embodiments, the nozzle includes a length of 2-20 mm. In some embodiments, the nozzle includes a length of 2-15 mm. In some embodiments, the nozzle includes a length of 2-10 mm.

In some embodiments, the nozzle includes a length of 5-8 mm.

In some embodiments, the device includes a power source (e.g., battery) and a switch configured to control (e.g., activate or deactivate) the power source.

In some embodiments, the device includes a charging port. For example, the charging port can comprise a micro USB port, a magnetic connector, or a wireless charger. In some embodiments, the charging port is part of a power unit of the device. The power unit may also include a battery (e.g., a rechargeable battery), and the charging port connects the device to a power source (e.g., via a cable) to recharge the battery.

In some embodiments, the fluid comprises an ophthalmic fluid (e.g., liquid eye drops). For example, the ophthalmic fluid can be used to treat conditions such as dry eye, eye infections, eye allergies and/or corneal ulcers, etc.

In some embodiments, the fluid comprises a nasal solution.

In some embodiments, the fluid comprises a vaccine.

In some embodiments, the device is configured to administer the fluid through a person's eye.

In some embodiments, the device is configured to administer the fluid through a person's nose.

In accordance with some embodiments, a method of administering ophthalmic fluids and/or fluid-based vaccines is performed by a device. The device includes an actuator having an extendible (and retractable) piston. The device includes an air pump. The method includes operating the actuator such that the piston extends towards a compartment of the device and exerts (e.g., applies) a force (e.g., push force, or pressure) on a liquid reservoir positioned in the compartment. The force causes fluid contained in the liquid reservoir to be expelled from the liquid reservoir. In some embodiments, the fluid is expelled at (e.g., proximate to) a first end of the device. The method includes operating the air pump to atomize the fluid at the first end as it is ejected from the liquid reservoir.

Accordingly, the devices and/or methods disclosed herein advantageously improve the administration of ophthalmic fluids, nasal solutions, ear solutions, and/or fluid-based vaccines, etc. in several aspects, as described below:

First, the fluid (and fluid path) is fully contained within the liquid reservoir (e.g., liquid capsule) until it is expelled through the device opening. Accordingly, the fluid does not contact any other parts in the device, thus providing hygiene and minimizing contamination.

Second, the solutions and/or vaccines to applied to a user can be contained in a fully enclosed liquid reservoir (e.g., a sealed capsule, a sealed package) for use in conjunction with the device. The liquid reservoir can be individually packaged for single use, and can be disposed after use. This makes it safe, easy, and convenient for the user, and minimizes the risk of contamination.

Third, in some embodiments disclosed herein, the device includes a spray head, which can be easily replaced and/or disposed as needed. This also reduces the risk of contamination and improves user safety.

Fourth, the disclosed devices and/or methods improve over conventional, ultrasonic-based sprays (e.g., resonators)

in the case of administering fluid-based vaccines. Ultrasonic-based resonators tend to be more effective at administering liquids of low viscosity (e.g., water and other low viscosity liquids, liquids with a viscosity of <2 centipoises, etc.) but are less effective at administering high viscosity fluids. Because many fluid-based vaccines tend to have high viscosity, the ultrasonic-based approaches are not ideal for delivering the vaccines. The disclosed device uses an air pump with a motor for the atomization process, making it more effective for atomizing fluids with high viscosity compared to the conventional resonators.

Fifth, in some instances, vaccines need to be stored at low temperature (e.g., −40° C., −80° C., etc.). Because the disclosed device includes a compartment for placing an enclosed liquid reservoir (e.g., vaccine-containing capsule, vaccine-containing liquid reservoir), only the liquid capsules—and not the devices—need to be stored at low temperature. Consequently, the disclosed device does not take up additional storage space in the low-temperature storage areas.

Furthermore, the average volume of vaccination required for vaccinating a person is typically about 500 μl. The disclosed devices and methods can be used complementarily with fluid-based vaccines, which can be individually packaged and sealed in small volumes. The vaccines can remain sealed until they are applied to a user's sensory organ (e.g., nose). Thus, the disclosed device and methods as applied to vaccine delivery render it safe, easy, and convenient for the user and reduces the risk of contamination.

Accordingly, the disclosed device and method offer hygienic and safe and delivery precision. The small droplet sizes (e.g., <100 μm) enables the active ingredients of the fluid/vaccine to be better absorbed by a user.

FIG. 17 illustrates a device 1700 (e.g., an apparatus) that can be used to deliver solutions (e.g., ophthalmic fluids, nasal solutions, ear solutions, etc.) and/or fluid-based vaccines, according to some embodiments.

In some embodiments, the device 1700 includes a housing 1702 (e.g., an outer case, a casing, etc.). In some embodiments, the housing 1702 comprises a detachable (e.g., removable) housing. For example, the housing 1702 can include an upper portion 1704 and a lower portion 1706, which are connected to or separated from each other via region 1708.

In some embodiments, the device 1700 includes an actuator 1710 that produces motion by converting energy and signals going into the actuator 1710. In some embodiments, the actuator 1710 comprises a linear actuator.

FIGS. 17, 18A, and 18B illustrate the actuator 1710 includes a motor 1716 in accordance with some embodiments. In some embodiments, the motor 1716 is DC-powered. In some embodiments, the motor 1716 is AC-powered.

In some embodiments, the actuator 1710 includes a hybrid stepper motor/linear actuator that includes an extendible piston 1718 (e.g., a lead screw, a rod, a shaft, etc.) as a rotor, which translates motor torque into linear thrust. The stepper motor linear actuator provides good force and speed capabilities with high positioning accuracy. FIG. 18A illustrates in some embodiments, the piston 1718 is in a fully retracted position when the device 1700 (e.g., the actuator 1710) is not in use. In some embodiments, the piston 1718 is at least partially retracted when the device 1700 (e.g., the actuator 1710) is not in use. FIGS. 17 and 18B illustrate in some embodiments, during the operation of the actuator 1710, the piston 1718 translates torque from the motor 1716 into a linear motion (e.g., a translational motion, a forward and/or backward motion, etc.) with direction illustrated by arrow 1720. In some embodiments, the piston 1718 executes a translational motion that is substantially parallel to a length L of the device 1700. FIG. 18B also illustrates in some embodiments, during operation of the actuator 1710, a portion of the piston 1718 extends (e.g., protrudes) from the main body of the actuator 1710. In some embodiments, the piston 1718 has a stroke ranging not exceeding 100 mm (e.g., the piston 1718 has a maximum extension of 100 mm from the main body of the actuator 1710). In some embodiments, the piston 1718 has a stoke ranging from 5 mm to 100 mm. In some embodiments, the actuator 1716 is configured to retract at least a portion of the piston 1718 into the main body of the actuator 1716 after device operation.

With continued reference to FIG. 17, in some embodiments, the device 1700 includes an air pump 1712. In some embodiments, the air pump 1712 includes a motor 1722. In some embodiments, the motor 1722 is DC-powered. In some embodiments, the motor 1722 is AC-powered.

FIG. 17 illustrates in some embodiments, the device 1700 (e.g., the upper portion 1704 of the housing) includes a compartment 1728 (e.g., a region) for placement of a liquid reservoir 1714 (e.g., a capsule). For example, a user can separate the upper portion 1704 of the housing from the lower portion 1706 (e.g., via reference numerals 1708), and place the liquid reservoir 1714 at the upper portion 1704. In some embodiments, as illustrated in FIGS. 19A and 19B, the upper portion 1704 of the housing includes alignment marks 1730 that guide a user to place the liquid reservoir 1714, so that the liquid reservoir 1714 aligns with the piston 1718 during device operation. FIG. 19A illustrates insertion (e.g., placement) of the liquid reservoir 1714 into the upper portion 1704 via the alignment marks 1730. FIG. 19B illustrates positioning of the liquid reservoir 1714 in the upper portion 1704.

In some embodiments, the liquid reservoir 1714 contains a fluid (e.g., liquid). For example, in some embodiments, the fluid can comprise an ophthalmic solution, a nasal solution, an ear solution, or a fluid-based vaccine. In some embodiments, the device 1700 is configured to administer the fluid through a person's eye. In some embodiments, the device 1700 is configured to administer the fluid through a person's nose. In some embodiments, the device 1700 is configured to administer the fluid through a person's ear.

In some embodiments, the fluid in the liquid reservoir 1714 has a volume ranging from 100 μl to 3000 μl. In some embodiments, the liquid reservoir is shaped like a capsule. For example, the liquid reservoir 1714 can include a circular (e.g., cylindrical) shape with a diameter ranging from 5 mm to 20 mm. In some embodiments, the fluid is fully enclosed (e.g., fully sealed) in the liquid reservoir 1714 until it is administered to a person, as described in further detail in FIG. 21.

Referring again to FIG. 17, in some embodiments, the device 1700 includes a controller 1732 that electrically (and communicatively) couples the actuator 1710 and the air pump 1712 via wired connections 1734. In some embodiments, the controller 1732 is implemented by one or more processors and memory (or another non-transitory computer-readable medium) storing instructions, the instructions, when executed by the one or more processors, cause the processors to perform operations disclosed herein.

In some embodiments, the device 1700 includes a power source (e.g., a battery) and a switch configured to control (e.g., activate or deactivate) the power source.

In some embodiments, the device 1700 includes a charging port. For example, the charging port can comprise a micro USB port, a magnetic connector, or a wireless charger. In some embodiments, the charging port is part of a power unit of the device 1700. The power unit may also include a battery (e.g., a rechargeable battery), and the charging port connects the device to a power source (e.g., via a cable) to recharge the battery.

FIG. 17 illustrates in some embodiments, the device 1700 includes an opening 1726. In some embodiments, the device 1700 includes a nozzle 1724 near (e.g., adjacent to) the opening 1726. FIGS. 20A and 20B illustrate exemplary designs of the nozzle 1724 according to some embodiments. FIG. 20B shows that in some embodiments, the nozzle 1724 is protruded from the device housing. In some embodiments, the length of the nozzle (e.g., the length of protrusion 1725) ranges from 5 mm to 25 mm. In some embodiments, the position of the opening 1726 is designed to match the tip of the nozzle 1726. For example, FIG. 20B illustrates the top portion of the housing includes a tip 1740 having a length that matches a length of the nozzle 1724, in accordance with some embodiments.

FIG. 21 illustrates operation of a device 1700 according to some embodiments. In some embodiments, during device operation, the controller 1732 sends an electrical signal to the actuator 1710, which drives the piston 1718 to execute a translational movement (e.g., extend) in a direction indicated by arrow 1736. The controller 1732 sends a signal to activate the air pump 1712, which drives air to flow from pump outlets 1737 in a direction indicated by the dashed arrows 1738. The air exits via the opening 1726. In some embodiments, the air pump 1712 has air flow rate ranging from 1 to 4 liters per minute.

FIG. 21 illustrates in some embodiments, the movement of the piston 1718 causes the piston to exert (e.g., apply) a force (e.g., a push force) on the liquid reservoir 1714 (e.g., at a bottom of the liquid reservoir 1714). In some embodiments, the force causes the liquid reservoir 1714 to move toward the top of the device 1700. In some embodiments, the force exerted by the piston 1718 on the liquid reservoir 1714 causes the fluid to be expelled (e.g., ejected) from the liquid reservoir 1714 (e.g., through the nozzle 1724). In some embodiments, the force exerted by the piston 1718 on the liquid reservoir 1714 causes a portion of the liquid reservoir 114 to break and causes fluid to be expelled (e.g., ejected) from the liquid reservoir 1714. In some embodiments, as the fluid is expelled from the liquid reservoir 1714, the fluid encounters the airflow exiting via the opening 1726. In some embodiments, the interaction between the fluid and the air flow causes the fluid to be atomized as it exits the nozzle 1724 (e.g., opening 1726). In some embodiments, the atomization of the fluid produces (e.g., generates) a mist of the fluid. In some embodiments, the mist includes a droplet size not exceeding 100 μm.

It should be apparent to one of ordinary skill in the art that the atomization process described with respect to FIG. 21 also applies in the case where the device 1700 includes a nozzle 1724 that is protruded from the device housing. For example, in some embodiments, by matching a position of the opening 1726 to a position of the nozzle 1724 (see, e.g., FIG. 20B) (e.g., the opening is adjacent to the nozzle, at a same height as the nozzle, etc.), air exiting via the opening 1726 can interact with fluid that is expelled from the liquid reservoir 1714, thereby atomizing the fluid.

Figure 22B:
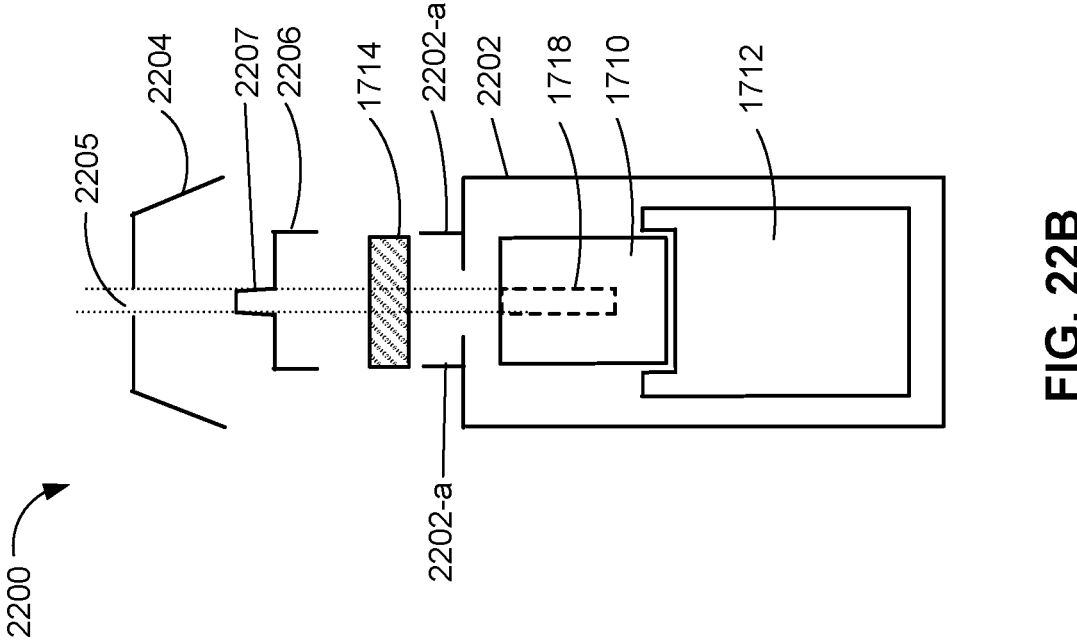
FIGS. 22A and 22B illustrate a device that can be used to deliver solutions and/or fluid-based vaccines, according to some embodiments.
Figure 22A:
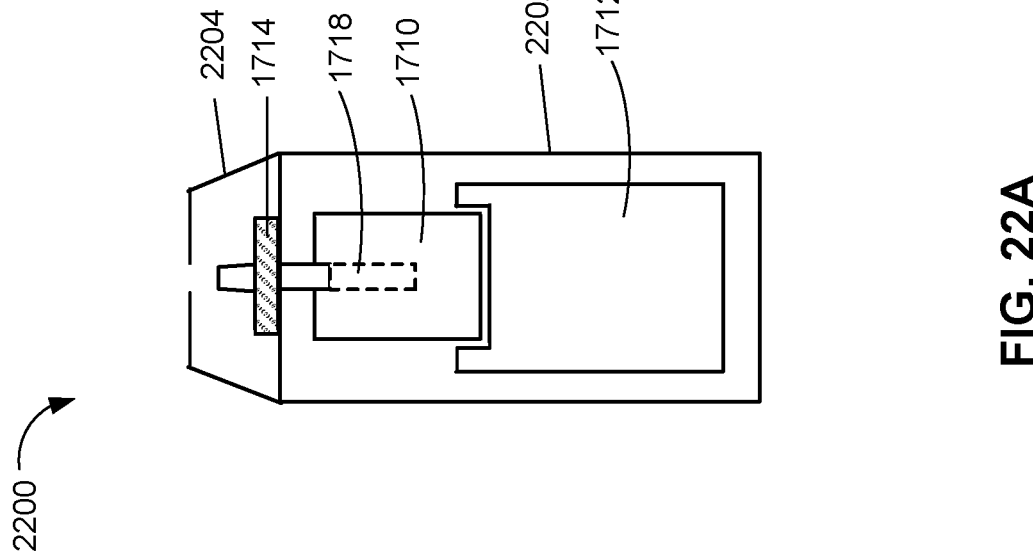

FIGS. 22A and 22B illustrate a device 2200 that can be used to deliver ophthalmic fluids, nasal sprays, ear solutions, and/or fluid-based vaccines, according to some embodiments.

In some embodiments, the device 2200 includes an actuator 1710 (e.g., linear actuator) with an extendible piston 1718, and an air pump 1712. These components have been discussed with respect to FIGS. 17 to 21 and will not be repeated for the sake of brevity.

In some embodiments, the device 2200 includes a housing 2202 (e.g., an outer case, a casing, etc.). In some embodiments, the housing 2202 includes alignment guides 2202-*a* (e.g., alignment marks) that can be used to guide a user on how to place a liquid reservoir 1714 on the device 2200 so that the liquid reservoir 1714 aligns with the piston 1718 during device operation.

FIG. 22B illustrates how the various components of the device 2200 are positioned with respect to one another, in accordance with some embodiments.

In some embodiments, the device 2200 includes a removable (e.g., detachable) spray head case 2204. The spray head case includes an opening 2205. In some embodiments, the device 2200 includes a removable (e.g., detachable) spray head 2206 with a nozzle 2207, which is placed over a liquid reservoir 1714. In some embodiments, the combination of the spray head 2206 and the liquid reservoir form a single component In an exemplary usage scenario, a user removes the spray head case 2204, removes the spray head 2206, and inserts the liquid reservoir 1714 (e.g., an enclosed capsule filled with an ophthalmic fluid, a fluid for the nose, a vaccine, etc.). The user positions the spray head 2206 over the reservoir, and positions (e.g., connects) the spray head case 2204 with the housing 2202. The user activates a switch that is positioned on the device 2200. In some embodiments, user activation of the switch causes an electrical signal to be sent the controller 1732. In some embodiments, the controller 1732 sends a signal to activate the air pump 1712. In some embodiments, the controller 1732 sends an electrical signal to the actuator 1710, which drives the piston 1718. The piston 1718 executes a translational movement which pushes the liquid reservoir 1714 and expels the fluid from the liquid reservoir 1714 through the nozzle 1724 into a surrounding of the device. The fluid is atomized at the opening 2205 when the fluid encounters the air.

FIGS. 23A to 23D illustrate air flow in the device 2200 during device operation, in accordance with some embodiments. In each of these figures, the arrows 2208 represent a direction of air flow (e.g., from the pump 1712), and the arrow 2210 represents a direction of fluid flow.

Figures 23A, 23B, 23C, 23D:
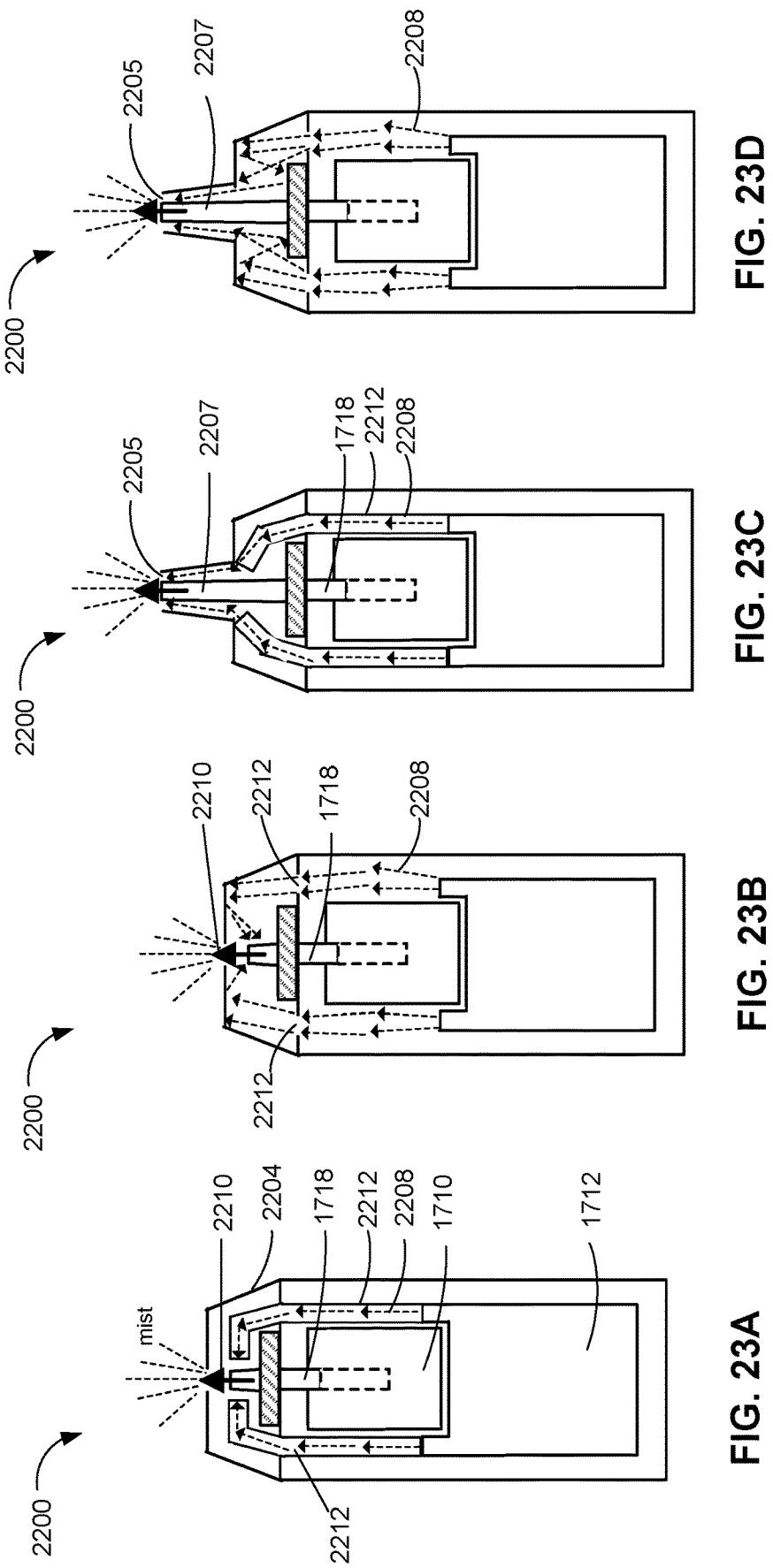
FIGS. 23A to 23D illustrate air flow in a device during device operation, in accordance with some embodiments.

FIG. 23A illustrates in some embodiments, the device 2200 includes hollow channels 2212 for air flow. In some embodiments, the hollow channels 2212 are formed through molding as part of the design of the device 2200. FIG. 23C illustrates an air flow path that also utilizes the hollow channels 2212 that is described in FIG. 23A, for a device that includes a longer nozzle 2207.

FIG. 23B illustrates in some embodiments, the device 2200 includes one or more holes 2212 (e.g., complementary holes at the housing and the spray head case 2204) that facilitate air flow from the air pump 1712 to the opening 2210. FIG. 23D illustrates an air flow path that utilizes holes 2212 as described in FIG. 23B.

FIGS. 23C and 23D also illustrate in some embodiments, when the position of the opening 2205 matches (e.g., is located next to, adjacent to) the position of the opening of the nozzle 2207, effective atomization of the fluid can be achieved.

As shown above, during operation of the device 1700 or the device 2200, the liquid path is contained within the liquid reservoir 1714 and the nozzle, and does not contact other parts of the device. Therefore, the disclosed device 1700 and the disclosed device 2200 can be used with minimal contamination. Furthermore, because components such as the liquid reservoir 1714, the spray head case 2204, and the spray head 2206 with nozzle 2207 are easily replaceable and can be disposed as needed, user safety is improved, and the risk of contamination is reduced.

FIG. 24 illustrates a flowchart for an exemplary method 2400 of administering a fluid, in accordance with some embodiments. In some embodiments, the method 2400 uses a device (e.g., device 1700 or device 2200). The device includes an actuator (e.g., actuator 1710) having an extendible piston (e.g., piston 1718) and an air pump (e.g., air pump 1718). In some embodiments, the method 2400 includes operating (2402) the actuator such that the piston extends towards a compartment of the device and exerts a force on a liquid reservoir positioned in the compartment such that the force causes the fluid to be expelled from the liquid reservoir, at a first end of the device. In some embodiments, the method includes operating (2404) the air pump to atomize the fluid at the first end as it is expelled from the liquid reservoir.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

What is claimed is:

1. A device for administering fluid compositions, comprising:
   a housing having a first end and a second end opposite to the first end, the first end including an opening;
   a compartment proximate to the first end, the compartment capable of holding a liquid reservoir that is at least partially filled with a fluid;
   an air pump positioned within the housing, at the second end; and
   an actuator positioned within the housing, between the compartment and the air pump, the actuator including an extendible piston that is configured to execute a translational movement.

2. The device of claim 1, wherein:
   the liquid reservoir is fully sealed; and
   the device further comprises a controller storing instructions that, when executed by the controller, cause the controller to:

operate the actuator such that the piston executes a translational movement towards the liquid reservoir and exerts a force on the liquid reservoir, wherein the force causes the fluid to be expelled from the liquid reservoir at the first end; and operate the air pump to atomize the fluid at the first end as it is expelled from the liquid reservoir.

3. The device of claim 2, wherein the controller further includes instructions that, when executed by the controller, cause the controller to:

operate the air pump via a motor at an air flow rate of 1 to 4 liters per minute.

4. The device of claim 2, wherein:

atomizing the fluid includes generating a mist of the fluid, the mist having a droplet size not exceeding 100 μm.

5. The device of claim 1, wherein the fluid has a volume ranging from 300 μl to 1000 μl.

6. The device of claim 1, wherein the liquid reservoir has a diameter ranging from 5 mm to 15 mm.

7. The device of claim 1, wherein the air pump is operable via a motor.

8. The device of claim 1, wherein the actuator is operable via a motor.

9. The device of claim 1, wherein the piston includes a stroke not exceeding 100 mm.

10. The device of claim 1, wherein the actuator comprises a linear actuator having a motor that is configured to convert rotational motion into a translational motion of the piston.

11. The device of claim 1, wherein the compartment is positioned within the housing at the first end.

12. The device of claim 1, further comprising:

a spray head positioned at the first end, wherein the compartment is located in the spray head.

13. The device of claim 12, wherein the spray head includes a nozzle.

14. The device of claim 13, wherein the nozzle includes a length having a range of 5-10 mm.

15. The device of claim 13, wherein the nozzle includes a length having a range of 5-8 mm.

16. The device of claim 1, further comprising:

a power source; and a switch configured to control the power source.

17. The device of claim 1, wherein the fluid is one of:

an ophthalmic solution;

a nasal solution; or a vaccine.

18. The device of claim 1, wherein the device is configured to administer the fluid through a person's eye.

19. The device of claim 1, wherein the device is configured to administer the fluid through a person's nose.

* * * * *